US011808675B2

(12) United States Patent
Van de Bittner et al.

(10) Patent No.: US 11,808,675 B2
(45) Date of Patent: Nov. 7, 2023

(54) ROOM TEMPERATURE METHODS FOR PREPARING BIOLOGICAL ANALYTES

(71) Applicant: Agilent Technologies, Inc., Santa Clara, CA (US)

(72) Inventors: Genevieve Van de Bittner, Campbell, CA (US); James Alexander Apffel, Mountain View, CA (US); Steven M. Fischer, Hayward, CA (US); Christine A. Miller, Campbell, CA (US); Kristin Briana Bernick, San Jose, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 581 days.

(21) Appl. No.: 16/874,499

(22) Filed: May 14, 2020

(65) Prior Publication Data

US 2020/0393342 A1 Dec. 17, 2020

Related U.S. Application Data

(60) Provisional application No. 62/861,115, filed on Jun. 13, 2019.

(51) Int. Cl.
```
G01N 1/28      (2006.01)
C12N 1/06      (2006.01)
B01D 15/00     (2006.01)
C12N 15/10     (2006.01)
B01D 11/02     (2006.01)
C07K 1/14      (2006.01)
```

(52) U.S. Cl.
CPC ............ *G01N 1/28* (2013.01); *B01D 11/0288* (2013.01); *B01D 15/00* (2013.01); *C07K 1/145* (2013.01); *C12N 1/06* (2013.01); *C12N 15/1006* (2013.01)

(58) Field of Classification Search
CPC .......... G01N 1/28; B01D 11/02; B01D 15/00; C07K 1/145; C12N 1/06
See application file for complete search history.

(56) References Cited

U.S. PATENT DOCUMENTS

| | | | |
|---|---|---|---|
| 6,150,172 A * | 11/2000 | Schmerr | C07K 14/47 435/68.1 |
| 6,534,996 B1 | 3/2003 | Amrany et al. | |
| 6,924,478 B1 | 8/2005 | Zubarev et al. | |
| 7,145,133 B2 | 12/2006 | Thomson | |
| 7,229,834 B2 | 6/2007 | Chace | |
| 7,507,953 B2 | 3/2009 | Makarov et al. | |
| 7,531,793 B2 | 5/2009 | Satoh et al. | |
| 10,012,574 B2 | 7/2018 | Apffel, Jr. | |
| 2015/0045232 A1* | 2/2015 | Han | C12Q 1/6806 435/7.1 |
| 2015/0369711 A1 | 12/2015 | Smart et al. | |
| 2018/0080858 A1 | 3/2018 | Richter et al. | |
| 2019/0389815 A1* | 12/2019 | Eckhardt | A61P 9/04 |
| 2020/0393342 A1* | 12/2020 | Van de Bittner | B01D 15/00 |

FOREIGN PATENT DOCUMENTS

| | | | |
|---|---|---|---|
| EP | 2317323 A1 * | 4/2011 | |
| WO | WO 2006/113915 | * 10/2006 | |

OTHER PUBLICATIONS

Kim et al., Separation of lipid classes by solid phase extraction. J of Lipid Research31:2285-2289 (Year: 1990).*
Vaghela et al.,A rapid method for extraction of total lipids from whey protein concentrates and separation of lipid classes with solid phase extraction. JAOCS 72(10) : 1117 (Year: 1995).*
Ruiz-Gutierrez et al.,Update on solid-phase extraction for the analysis of lipid classes and related compounds. J. of Chromatograhy A 885:321-341 (Year: 2000).*
Gast et al., Fluoroalcohol-induced structural changes of proteins: some aspects of cosolvent-protein interactions. Eur. Biophys. J 30 : 273-283 (Year: 2001).*
Sirangelo et al., Hexafluoroisopropanol and acid destabilized forms of apomyoglobin exhibit structural differences. Biochemistry 42:312-319 (Year: 2003).*
Chertov et al., Organic solvent extraction of proteins and peptides from serum as an effective sample preparation for detection and identification of biomarkers by mass spectrometry. Proteomics 4: 1195-1203 (Year: 2004).*
Wang et al.,Development and evaluation of a micro- and nanoscale proteomic sample preparation method. J. of Proteome Research 4:2397-2409 (Year: 2005).*
Lin et al.,Evaluation of metabolite extraction strategies from tissue samples using NMR metabolomics. Metabolomics 3(1) :55 (Year: 2007).*
Wenger et al., An automated microscale chromatographic purification of virus-like particles as a strategy for process development. Biotechnol. Appl. Biochem.47:131-139 (Year: 2007).*
Gross et al., Tissue fractionation by hydrostatic pressure cycling technology: the unified sample preparation technique for systems biology studies. J of Biomolecular Techniques 19: 189-199 (Year: 2008).*
Ewald et al., High-throughput quantitative metabolomics: workflow for cultivation, quenching, and analysis of yeast in a multiwell format. Analytical Chemistry 81:3623-3629 (Year: 2009).*
Dohi et al., Fluoroalcohols: versatile solvents in hypervalent iodine chemistry and syntheses of diaryliodonium(III) salts. Tetrahedron 66:5775-5785 (Year: 2010).*
Camper et al., Fully automated protein purification. Analytical Biochemistry 393:176-181 (Year: 2009).*

(Continued)

*Primary Examiner* — Ethan C Whisenant
(74) *Attorney, Agent, or Firm* — Mannava & Kang, P.C.

(57) ABSTRACT

Reagents and methods for extracting and stabilizing metabolites at room temperature and methods in which metabolites and one or more of proteins, lipids and nucleic acids are extracted from a single sample in a unified workflow.

22 Claims, 29 Drawing Sheets

(56) References Cited

OTHER PUBLICATIONS

Freeman et al., Pressure-assisted lysis of mammalian cell cultures prior to proteomic analysis. A Chapter. in Sample Preparation in Biological Mass Spectrometry pp. 77-90. Abstract Only (Year: 2011).*
Kiefer et al., Nanoscale ion-pair reversed-phase HPLC-MS for sensitive metabolome analysis. Analytical Chemistry 83 : 850-855 (Year: 2011).*
Zhang et al.,Modern analytical techniques in metabolomics analysis. Analyst 137: 293-300 (Year: 2012).*
Reis et al., A comparison of five lipid extraction solvent systems for lipidomic studies of human LDL[S]. J. of Lipid Research 54:1812 (Year: 2013).*
Sapcariu et al., Simultaneous extraction of proteins and metabolites from cells in culture. MethodsX 1:74-80 (Year: 2014).*
Martano et al., Fast sampling method for mammalian cell metabolic analyses using liquid chromatography—mass spectrometry. Nature Prptocols 10(1) :1-11 (Year: 2015).*
Koolivand et al., Fluoroalcohol-induced coacervates for selective enrichment and extraction of hydrophobic proteins. J of Chromatography B 1083: 180-188 (Year: 2018).*
Ulmer et al., Optimization of Folch, Bligh-Dyer, and Matyash sample-to-extraction solvent ratios for human plasma-based lipidomics studies. Analytica Chimica Acta 1037 :351-357 (Year: 2018).*
Koolivand et al., Coacervation of lipid bilayer in natural cell membranes for extraction, fractionation, and enrichment of proteins in proteomics studies.J. of Proteome Research 18:1595-1606 (Year: 2019).*
Wang, et al., "Development and Evaluation of a Micro- and Nanoscale Proteomic Sample Preparation Method" Journal of Proteome Research, 2005, pp. 2397-2403, vol. 4.
Meza, et al., "Improved Tryptic Digestion of Proteins Using 2,2,2,-Trifluoreothanole (TFE)", 1. The 2004 ABRF meeting, Feb. 28, 2004.
Agrawal, et al. "Towards a Microfluidic nanoESI-MS Platform for Sample Preparation and Analysis of Single Cells", Pacific Northwest National Labaratory, The 2010 ASMS meeting. May 1, 2010.
Weckwerth, W. et al. "Process for the integrated extraction, identification and quantification of metabolites, proteins and RNA to reveal their co-regulation in biochemical networks", Proteomics, (2004) pp. 78-83, vol. 4, DOI 10.1002/pmic.200200500.
Nakayasu, E. S. et al., "MPLEx: a Robust and Universal Protocol for Single-Sample Integrative Proteomic, Metabolomic. and Lipidomic Analyses", mSystems, (2016), pp. 00043-16, vol. 1, doi:10.1128/mSystems.
Burnum-Johnson, K. E. et al., "MPLEx: a method for simultaneous pathogen inactivation and extraction of samples for multi-omics profiling", Analyst, Jan. 26, 2017, pp. 442-448, Analyst 142,442-448, vol. 142, No. 3, doi:10.1039/c6an02486f.
Nicora D. et al. "The MPLEx Protocol for Multi-omic Analyses of Soil Samples", Journal of Visualized Experiments, May 30, 2018, pp. 1-7, vol. 135, doi:10.3791/57343.
Valledor, L. et al., "A universal protocol for the combined isolation of metabolites, DNA, long RNAs, small RNAs, and proteins from plants and microorganisms", The Plant Journal, (2014), pp. 173-180, vol. 79, doi: 10.1111/tpj.12546.
Roume, H. et al., "A biomolecular isolation framework for eco-systems biology", The ISME Journal, (2103), pp. 110-121, doi: 10.1038/ismej.2012.72.
Sapcariu, S.C. et al., "Simultaneous extraction of proteins and metabolites from cells in culture", MethodsX, (2014), pp. 74-80, vol. 1, doi: 10.1016/j.mex.2014.07.002.
Chen, S. et al., Simultaneous extraction of metabolome and lipidome with methyl tert-butyl ether from a single small tissue sample for ultra-high performance liquid chromatography/mass spectrometry, Journal of Chromatography A, (2013), pp. 9-16, vol. 1298, doi:10. 1016/j.chroma.2013.05.019.

Tambellini, N. et al., "Evaluation of extraction protocols for simultaneous polar and non-polar yeast metabolite analysis using multivariate projection methods", Metabolites, (2013), pp. 592-605, vol. 3, doi:10.3390/metabo3030592.
Lee, D., et al., "Comparative evaluation of extraction methods for simultaneous mass-spectrometric analysis of complex lipids and primary metabolites from human blood plasma", AnalBioanal Chem, (2014), pp. 7275-7286, vol. 406, doi: 10.1007/s00216-014-8124-x.
Patterson, R. et al, R. E., "Comparison of blood plasma sample preparation methods for combined LC-MS lipidomics and metabolomics", J Chromatogr B Analyt Technol Biomed Life Sci, Oct. 1, 2015, pp. 260-266, vol. 1002, doi:10.1016/j.jchromb.2015. 08.018.
Juppner, et al., "Dynamics of lipids and metabolites during the cell cycle of Chlamydomonas reinhardtii", The Plant Journal, (2017), pp. 331-343, vol. 92, doi:10.1111/tpj.13642.
Astarita, G. et al, "Unbiased Lipidomics and Metabolomics of Human Brain Samples", Methods Mol Biol, (2018), pp. 255-269, vol. 1750, doi:10.1007/978-1-4939-7704-8_17.
Sostare, J. et al. "Comparison of modified Matyash method to conventional solvent systems for polarmetabolite and lipid extractions", Analytica Chimica Acta, (2018), pp. 301-315, vol. 1037, doi:10.1016/j.aca.2018.03.019.
Ulmer, C. et al., "Optimization of Folch, Bligh-Dyer, and Matyash sample-to-extraction solvent ratios for human plasma-based lipidomics studies", Analytica Chimica Acta, (2018), pp. 351-357, vol. 1037, doi:10.1016{j.aca.2018.08.004.
Li, Y. et al. "A novel approach to the simultaneous extraction and non-targeted analysis of the small molecules metabolome and lipidome using 96-well solid phase extraction plates with column-switching technology", Journal of Chromatography A, (2015), pp. 277-281, vol. 1409, doi:10.1016/j.chroma .2015.07.048.
Salem, M., et al., "Protocol: a fast, comprehensive and reproducible one-step extraction method for the rapid preparation of polar and semi-polar metabolites, lipids, proteins, starch and cell wall polymers from a single sample", Plant Methods, pp. 1-15, vol. 12, No. 25, doi:10.1186/s13007-016-0146-2, (2016).
Bylda, C. et al., "Recent advances in sample preparation techniques to overcome difficulties encountered during quantitative analysis of small molecules from biofluids using LC-MS/MS", Analyst, (2014), pp. 2265-2276, vol. 139, DOI:10.1039/C4AN00094C.
Salem, M. et al., "A Simple Fractionated Extraction Method for the Comprehensive Analysis of Metabolites, Lipids, and Proteins from a Single Sample" Journal of Visualized Experiments, (2107), pp. 1-10, vol. 124, doi:10.3791/55802.
Lu, W. et al., Metabolite Measurement: Pitfalls to Avoid and Practices to Follow, Annu. Rev. Biochem, Jun. 20, 2017, pp. 277-304, vol. 86.
Kapoore et al., "Influence of washing and quenching in profiling the metabolome of adherent mammalian cells: a case study with the metastatic breast cancer cell line MDA-MB-231", Analyst, (2017), pp. 2038-2049, vol. 142.
Martano, G. et al. "Fast sampling method for mammalian cell metabolic analyses using liquid chromatography—mass spectrometry" Nature Protocols, (2015), pp. 1-11, vol. 10, No. 1.
Sellick, C., et al. "Effective quenching processes for physiologically valid metabolite profiling of suspension cultured mammalian cells", Anal. Chem., (2009), pp. 174-183, vol. 81.
Dietmair S. et al. "Towards quantitative metabolomics of mammalian cells: development of a metabolite extraction protocol", Anal. Biochemistry (2010), pp. 55-164, vol. 404.
Kronthaler, J. et al. "Optimizing high-throughput metabolomic biomarker screening: a study of quenching solutions to freeze intracellular metabolism in CHO cells", OMICS: A Journal of Integrative Biology, Nov. 3, 2012, pp. 90-97, vol. 16, No. 3.
Bordag, N. et al. "Fast filtration of bacterial or mammalian suspension cell cultures for optimal metabolomics results", PLOS ONE, Jul. 20, 2016, pp. 1-16.
Leon, Z. et al. "Mammalian cell metabolomics: experimental design and sample preparation", Electrophoresis, (2013), pp. 1-29, www.electrophoresis-journal.com.

(56) References Cited

OTHER PUBLICATIONS

Lorenz M. et al., "Reducing time and increasing sensitivity in sample preparation for adherent mammalian cell metabolomics", Analytical Chemistry, (2011), pp. 3406-3414, vol. 83.

Pannkuk, E. L. et al., "A Lipidomic and Metabolomic Serum Signature from Nonhuman Primates Exposed to Ionizing Radiation", Metabolomics, May 2016, pp. 1-18, vol. 12, No. 5, doi:10.1007/s11306-016-1010-0.

Folch J. et al., "A Simple Method for the Isolation and Purification ot Total Lipides from Animal Tissues", J Biol Chem, (1956), pp. 497-509.

Bligh E. et al., "A Rapid Method of Total Lipid Extraction and Purification", Canadian Journal of Biochemistry and Physiology, (1959), pp. 911-917, vol. 37, No. 8, doi:10.1139/o59-099.

Matyash, V. et al., "Lipid extraction by methyl-tert-butyl ether for high-throughput lipidomics", ASBMB, Journal of Lipid Research, (2008), pp. 1137-1146, vol. 40.

Alshehry Z. et al., "An Efficient Single Phase Method for the Extration of Plasma Lipids", Metabolites, (2015), pp. 389-403, vol. 5., doi:10.3390/metabo5020389.

Koelmel J. et al., Improving Coverage of the Plasma Lipidome Using Iterative MS/MS Data Acquistion Combined with Lipid Annotator Software and 6546 LC/Q-TOF, Agilent, (2019), pp. 1-10.

Koelmel J. et al., "Lipid Annotator: Towards Accurate Annotation in Non-Targeted Liquid Chromatography High-Resolution Tandem Mass Spectrometry (LC-HRMS/MS) Lipidomics Using a Rapid and User-Friendly Softward", Metabolites, (2020), pp. 1-21, vol. 10, No. 101.

\* cited by examiner

ROOM TEMPERATURE METHODS FOR PREPARING BIOLOGICAL ANALYTES

CROSS-REFERENCE TO RELATED APPLICATIONS

This patent application claims the benefit of priority to U.S. Provisional Patent application 62/861,115 filed Jun. 13, 2019, the entire disclosure of which is herein incorporated by reference.

TECHNICAL FIELD

The present disclosure relates to the field of metabolomics, including methods, reagents, compositions, kits and systems for obtaining metabolites, including polar metabolites and lipids from a biological sample. The present disclosure also relates to a unified workflow method in which metabolites, including polar metabolites, and one or more of lipids, proteins, peptides, and/or nucleic acids can be obtained from a single sample. These methods, reagents, compositions, kits and systems may find applications in many fields, including in basic biological research, pharma and biopharma, clinical diagnostics, patient treatment, synthetic biology, environmental protection, research and drug development, food testing and agriculture, and forensic toxicology.

BACKGROUND

A cornerstone of sample preparation methods for metabolomics is a step that provides near-instantaneous quenching of metabolism to ensure the metabolites measured from the sample accurately reflect the levels of metabolites that were present in the biological sample at the time of harvesting.

Most current methods used for metabolism quenching utilize cold or hot temperatures to freeze enzyme activity and the concomitant interconversion of metabolites. Often, temperatures of 0.5° C. to −80° C. (cold) or about 80° C. (hot) are used (21-28). Methods that use liquid nitrogen (−196° C.) to snap-freeze cell culture samples immediately following cell culture media removal (with or without a wash step) have also been described (29). To complete methods such as these expeditiously, samples are often handled one-at-a-time to ensure the time between removing the sample from its native conditions (e.g. removing a cell culture plate from an incubator) and the quenching step is minimized to minimize metabolite turnover. This complicates an already time-consuming sample preparation process and would be greatly improved via automation.

Automation is often a difficult goal to achieve when using cold temperatures, as they cause condensation to collect on robotics instruments and potentially directly in the quenching solutions, thus modifying their composition. Automation is equally difficult to achieve when using hot temperatures, as high temperatures lead to increased evaporation rates, which can result in evaporation of the quenching solution. This, in turn, can leave an automated system with insufficient volume of the quenching solution, can alter the composition of the quenching solution, and can lead to deposition of quenching solution on robotic components, which may cause degradation of the robotic system. Sample preparation methods that could accomplish metabolism quenching at room temperature would make automation of these sample preparation methods easier and would make it easier and safer to conduct the sample preparation methods manually as well.

There are extremely limited examples of metabolism quenching reagents that act at room temperature to prevent the turnover of metabolites. One example technology is the use of ionic liquids to lyse cells or other biological samples and quench metabolism during preparation of metabolomics samples, including as described in US Patent Publications U.S. Pat. No. 10,012,574 and US 2015/0369711, incorporated herein by reference. Although these methods work at room temperature, the ionic liquids used in these methods are not mass spectrometry compatible, and therefore need to be removed prior to down-stream mass spectrometry analysis. The removal of the ionic liquids adds potentially expensive steps to the sample preparation method, making the method more complex and increasing the probability of sample loss.

Attempts have been made to develop a microfluidic nano ESI-MS platform for sample preparation and analysis of single cells (30).

There are also previous examples of methods for isolating multiomic components of single samples. One of the earliest examples of isolating and quantifying metabolites, proteins and RNA from a single biological sample was described by Weckwerth et al (1). In this protocol, plant leaves were harvested and frozen in liquid nitrogen, the leaves were homogenized in liquid nitrogen, and two milliliters of a single phase solvent mixture of methanol/chloroform/water 2.5:1:1 v/v/v kept at −20° C. was added to the tissue and thoroughly mixed at 4° C. for 30 min to precipitate proteins and DNA/RNA and to disassociate metabolites from membrane and cell wall components. The pellet was extracted again with methanol:chloroform (1:1), and the organic solvent extracts were combined and the chloroform was separated from the aqueous water:methanol phase, creating a biphasic solution with separated polar metabolites and lipids (i.e. liquid-liquid extraction, LLE). The proteins were obtained from the pellet using a phenol extraction, overnight acetone precipitation at −20° C., and chloroform precipitation. Thus, this method requires an overnight cold temperature protein precipitation. There is also a need to separate the biphasic buffer and phenol solution created at this step, which is again a difficult step to automate. The Weckwerth method then precipitates RNA using acetic acid and ethanol. Centrifugation is required throughout this protocol, which is another difficult to automate process.

Nakayasu et al. have developed the MPLEx methodology (2-4). In the MPLEx method, cell pellets are suspended in water, and a −20° C. chloroform methanol solution is added. The samples are mixed and the organic and aqueous layers are separated by centrifugation. The aqueous layer is collected for metabolomics analysis and the organic layer is collected for lipidomics analysis. The interphases, which contain the proteins, are collected and further processed for proteomics analysis. The MPLEx method is difficult to automate due to the centrifugation step and the need to carefully separate the organic, aqueous and interphase layers to obtain the lipid, metabolite and protein portions of the sample.

Valledor et al. have described a method for combined isolation of metabolites, DNA, long RNAs, small RNAs, and proteins from plants and microorganisms, which treats pellets formed from metabolite extraction with a chaotropic salt and detergents, passes the samples through a series of silica columns to remove DNA. large RNA, and small RNA, and purifies the proteins using a phenol purification method (5).

Roume et al have also described a method for isolating high-quality genomic DNA, large and small RNA, proteins, and polar and non-polar metabolites from single microbial samples (6). In this method, metabolites are first extracted with organic and aqueous solvents and then the nucleic acids and proteins are separated using chromatographic spin columns. The extraction of metabolites for this method results in a three-phase sample, containing an organic layer (non-polar metabolites), an aqueous layer (polar metabolites) and an interphase layer (genomic DNA, large and small RNA, proteins and non-lysed cells). Additionally, this method freezes cells using liquid nitrogen to quench metabolism, and the handling of liquid nitrogen is also prohibitive for automation.

Sapcariu et al have described a method for the simultaneous extraction of proteins and metabolites from cells (7). In this method, a three-phase methanol-water-chloroform extraction is completed. As with some of the other methods described above, this results in a three-phase solution that needs to be carefully separated to obtain the metabolomic, lipidomic, and protein fractions of the sample. This separation process is difficult to automate.

In the field of lipidomics, several liquid-liquid extraction (LLE) methods have been described in which lipids have been recovered from the organic phase while polar metabolites have been recovered from the aqueous phase (8-16). Typically, in these procedures, the protein fractions are precipitated by the organic solvent and are discarded. Beyond this, the procedures suffer from the challenges of LLE. Specifically, LLE procedures are time-consuming to complete manually due to the need to carefully separate liquid layers. The separation of liquid layers also makes LLE methods difficult to automate, since the division between the liquid layers must be sensed by the automation instrument.

Li et al. (17) reported on the use of solid phase extraction (SPE) for separation of lipids from metabolites. This protocol utilizes Waters Ostro SPE Plates which are based on C18 material and retain lipids on the basis of hydrophobicity. This approach suffers from a lack of specificity for lipid classes. Furthermore, no attempt was made or suggested by Li to recover the proteins.

In two publications (18-19) from Salem et al., a methyl tert-butyl ether (MTBE) based LLE procedure was used to recover polar metabolites, lipids and proteins. In this application, in the LLE procedure, water is the upper layer which isolates polar metabolites, MTBE is the lower layer of the two-phase system which concentrates lipids, and the protein precipitate can be recovered as a pellet. However, this approach suffers from the limitations of LLE mentioned above.

Bylda et al have published a review of some of the topics involved in sample preparation (20).

As discussed above, in the realm of analytical bioanalysis, for each of the major omics (transcriptomics, proteomics, metabolomics, lipidomics) there exists a rich literature and wealth of well-developed methodologies for sample preparation, optimized to isolate the class of molecules of interest while discarding the majority of other "interfering" compounds. However, from a systems biology perspective, it is often important to measure more than one of these types of molecules from the same biological sample. While different methods for isolating different biomolecules (DNA, RNA, proteins, metabolites, lipids) from a single biological sample can be found in the art, these methods tend to be difficult to automate because the methods require cold temperature for quenching metabolism (particularly for metabolite and lipid preparations), they utilize liquid-liquid extractions that form multiphasic solutions that are not easily separated by robotic pipetting, and/or they utilize centrifugation steps that are cumbersome to automate.

Accordingly, there still exists a need in the field for methods, particularly for automated methods, that can be performed at room temperature for extracting metabolites from a biological sample with near-instantaneous quenching of metabolism and inhibition of enzymatic reactions to ensure the metabolites, polar metabolites and/or lipids measured from the biological sample reflect accurately the levels that were present in the biological sample at the time of harvesting. Furthermore, there is a need in the field for cell lysis and metaboliSID quenching solutions that do not interfere with detection of metabolites by a mass spectrometry analysis. There also exists a need for methods by which metabolites, including polar metabolites, are separated from lipids, which may interfere with a mass spectrometry analysis, using methods that are easily automated.

There is also a need in the field for a unified workflow in which in addition to (or instead of) metabolites, one or more of lipids, proteins and/or nucleic acids can be also obtained from a single sample.

SUMMARY

In one aspect, this disclosure provides methods for extracting metabolites from a biological sample, the methods comprising:
contacting at room temperature the biological sample with a metabolism-quenching solution comprising a fluoroalcohol,
inhibiting one or more metabolic reactions in the biological sample with the fluoroalcohol;
extracting a mixture from the biological sample with the metabolism-quenching solution comprising the fluoroalcohol, the mixture comprising metabolites, lipids and proteins;
separating the metabolites from the mixture; and
collecting the metabolites.
The method of claim 1, wherein the metabolism-quenching solution comprises 10-100% of the fluoroalcohol by volume.
The mixture may further comprise nucleic acids.
In any of these methods, the biological sample may comprise cells, and the cells are lysed by the fluoroalcohol. In some embodiments, the biological sample may comprise one or more of the following: cells, a tissue sample, blood, plasma, serum, mucus, lymphatic fluid, synovial fluid, cerebrospinal fluid, saliva, bronchiolar lavage, gastric lavage, amniotic fluid, urine, vaginal fluid, semen or feces.

The present methods may further comprise passing the mixture comprising metabolites and lipids through a solid-phase extraction matrix which binds the lipids; and collecting the metabolites in a flow through solution. In some of the methods, in addition to metabolites, lipids may be eluted and collected and/or proteins may be also collected by precipitation.

Any of the methods in this disclosure may further comprise one or more of the following steps: 1) evaporating a solvent and/or metabolite-quenching solution in order to dry and/or to concentrate the mixture comprising metabolites and then re-dissolving the mixture in a different solvent (change of solvent) and/or re-dissolving a sample in a smaller volume of the same or different solvent (sample concentration); 2) changing a solvent, e.g. by drying a sample and re-dissolving it in a different solvent, or modifying a solvent composition, e.g. by diluting the solvent, as may be needed at any step of a workflow; 3) diluting a sample, e.g. in order to increase a loading volume and/or to change a loading buffer when binding lipids to a solid-phase extraction matrix (column); and/or 4) washing a column and collecting and combining a wash with a flow-through in order to increase recovery of metabolites.

In some embodiments, the methods may comprise one or more of the following: washing the solid-phase extraction matrix with a wash solution which contains a water-containing solvent mixture and combining the wash solution with the flow through solution; and/or eluting and collecting lipids; and/or drying the collected metabolites and/or drying the eluted lipids. The wash solution contains one or more of the following: 2:1:1 water:ethanol:acetonitrile or 2:1:1 water:ethanol:methanol.

Some of the methods or at least some of steps may be performed at a temperature in the range from 10° C. to 30° C. and preferably in the range from 19° C. to 23° C.

In any of the present methods, the quenching, extraction and separation can be performed at room temperature.

In some embodiments, multiple fluoroalcohols can be used together. In addition to a fluoroalcohol, the metabolism-quenching solution may comprise one or more of the following: water, a water-miscible solvent, a detergent, an acid, a base, a salt, or any combination thereof and in particular, the metabolism-quenching solution may comprise one or more of the following: water, acetonitrile, ethanol, methanol, isopropanol, acetic acid, formic acid, medronic acid, phosphate buffered saline, and/or ammonium bicarbonate. However, in some other embodiments, the metabolism-quenching solution may consist of a fluoroalcohol or a mixture of several fluoroalcohols.

Any of the present methods may comprise one or more of the following: filtration, protein precipitation, size-exclusion and/or affinity chromatography. The methods may comprise filtering the mixture through a PVDF (polyvinylidene), nylon, PTFE (polytetrafluoroethylene), PC (polycarbonate), PP (polypropylene), PES (polyether sulfone), PVC (polyvinyl chloride), CA (cellulose acetate), CMF (coated cellulose acetate), HDPE (high density polyethylene), regenerated cellulose or glass fiber filter or a stacked combination of filter types. The methods may comprise contacting the mixture with an organic solvent and precipitating protein/peptide material from the mixture.

Preferred fluoroalcohols in the present methods include one or more of the following: 2,2,2-trifluoroethanol (TFE), 2,2-difluoroethanol, 2-fluoroethanol, hexafluoro-2-propanol, nonafluoro-tert-butyl alcohol, 1,1,2,2,2-pentafluoroethanol and/or 2,2,3,3,3-pentafluoro-1-propanol.

The present methods may be performed with the metabolism-quenching solutions comprising 10-100% of the fluoroalcohol by volume. In some preferred embodiments, the metabolism-quenching solution may comprise 2,2,2-trifluoroethanol. In some preferred embodiments, the metabolism-quenching solution may comprise from 45 v/v % to 55 v/v % of 2,2,2-trifluoroethanol.

In any of the present methods, separating the metabolites may comprise one or more of the following:
(a) filtering the mixture comprising the metabolites and collecting the flow through comprising the metabolites, the proteins and the lipids;
(b) precipitating the proteins from the mixture directly or from the flow through of (a), thereby obtaining a solution comprising the metabolites and the lipids;
(c) passing the solution of (b) through a solid-phase extraction matrix which binds the lipids; and
(d) collecting the metabolites in a flow through solution.

In some of the methods, in addition to metabolites, lipids may be eluted from the solid-phase extraction matrix and collected. In some of the methods, protein precipitates may be collected and analyzed.

In another aspect, the present disclosure provides a unified workflow method for extracting metabolites and one or more of proteins, lipids or nucleic acids from a single biological sample, the method comprising:
  contacting, preferably at room temperature, the biological sample with a metabolism-quenching solution which comprises a fluoroalcohol and thereby obtaining a mixture comprising metabolites, proteins, lipids and nucleic acids;
  optionally, drying the mixture and re-dissolving the mixture in a smaller volume of the metabolism-quenching solution;
  optionally, filtering the mixture comprising the metabolites, the proteins, the lipids and the nucleic acids through a filter and collecting the flow through comprising the metabolites, the proteins and the lipids;
  optionally, precipitating the proteins and thereby obtaining a solution comprising the metabolites and the lipids;
  optionally, separating the protein precipitates from the solution;
  optionally, diluting the solution with a solvent, buffer and/or water;
  passing the diluted solution comprising the metabolites and the lipids through a solid-phase extraction matrix that binds the lipids;
  collecting the metabolites in a flow-through solution;
  optionally, washing the solid-phase extraction matrix with a wash buffer and optionally, combining the wash buffer with the flow-through solution and thereby obtaining a solution comprising metabolites; and
  eluting the lipids from the solid-phase extraction matrix and thereby obtaining a solution comprising lipids;
  optionally, drying the solution comprising metabolites and/or the solution comprising lipids and re-solubilizing.

The unified workflow methods may comprise filtering the mixture through a glass fiber filter and eluting the nucleic acids from the filter. Any of the unified workflow methods may comprise precipitating the proteins with an organic solvent and collecting the precipitate on a filter or by centrifugation. In some embodiments, the protein precipitate may be re-dissolved in trifluoroethanol or heptafluoroisopropanol. In some embodiments, the protein precipitate may be re-dissolved with 5-7% SDS or 6M urea in 50 mM triethylammonium bicarbonate (TEAB). In some embodiments, FASP (Filter Aided Sample Prep), PASP (Positive Pressure Aided Sample Prep), and S-TRAP™ proteomics preparations may be used.

In some embodiments of the unified workflow method, prior to loading onto the solid-phase extraction matrix, the solution comprising the metabolites and the lipids, with or without the protein precipitate, is diluted with water and/or a water-miscible solvent, wherein the water-miscible solvent comprises one or more of the following: acetonitrile, ethanol, methanol, isopropanol, formic acid, acetic acid and any mixtures thereof. The lipids may be eluted from the solid-phase extraction matrix with non-polar, non-aqueous solvents or mixtures comprising one or more of MTBE, butanol, methanol, ethanol, dichloromethane, chloroform, or isopropanol.

In the unified workflow methods, the biological sample comprises one or more of the following: cells, a tissue sample, blood, plasma, serum, mucus, lymphatic fluid, synovial fluid, cerebrospinal fluid, saliva, bronchiolar lavage, gastric lavage, amniotic fluid, urine, vaginal fluid, semen or feces.

The unified workflow methods may comprise filtering the mixture through a PVDF (polyvinylidene), nylon, PTFE (polytetrafluoroethylene), PC (polycarbonate), PP (polypropylene), PES (polyether sulfone), PVC (polyvinyl chloride) CA (cellulose acetate), CMF (coated cellulose acetate), HDPE (high density polyethylene), regenerated cellulose or glass fiber filter or a stacked combination of filter types. The unified workflow methods may be performed with the fluoroalcohol in an amount from 10 v/v % to 100 v/v %, based on the total volume of the metabolism-quenching solution and the fluoroalcohol is one or more of the following: 2,2,2-trifluoroethanol, 2,2-difluoroethanol, 2-fluoroethanol, hexafluoro-2-propanol, nonafluoro-tert-butyl alcohol, 1,1,2,2,2-pentafluoroethanol and/or 2,2,3,3,3-pentafluoro-1-propanol. In some preferred embodiments, the metabolism-quenching solution comprises from 45 v/v % to 55 v/v % of: 2,2,2-trifluoroethanol. The metabolism-quenching solution may further comprise one or more of the following: water, a water-miscible solvent, a detergent, an acid, a base, a salt, or any combination thereof. Some of the metabolism-quenching solutions for the unified workflow methods may comprise one or more of the following: acetonitrile, ethanol, methanol, isopropanol, acetic acid, formic acid, medronic acid, phosphate buffered saline, and/or ammonium bicarbonate.

The unified workflow methods can be performed at a temperature in the range from 10° C. to 30° C., and preferably in the range from 19° C. to 23° C. In some further embodiments, all steps of the unified workflow are performed at room temperature.

In some embodiments, a unified workflow method may be performed with a biological sample which comprises suspension cells or adherent cells. The method may comprise:
(a) lysing and quenching the cells with a first metabolism-quenching solution which comprises from 10 v/v % to 100 v/v % of a fluoroalcohol and thereby obtaining a mixture comprising metabolites, proteins and lipids;
(b) precipitating the proteins from the mixture with an organic solvent, and thereby obtaining a solution comprising the metabolites and the lipids and a protein precipitate;
(c) diluting the solution of step (b) with water and/or a water-miscible solvent, wherein the water-miscible solvent comprises one or more of the following: acetonitrile, ethanol, methanol, isopropanol, formic acid, acetic acid or any mixtures thereof;
(d) passing the solution comprising the metabolites and the lipids from (c) through a solid-phase extraction matrix which binds lipids;
(e) collecting the metabolites in a flow-through solution;
(f) washing the solid-phase extraction matrix with a wash solution which contains a water-containing solvent mixture and combining the wash solution with the flow through solution of step (e); and
(g) eluting the lipids from the solid-phase extraction matrix.

In some embodiments, this method may further comprise one or more of the following additional steps:
(h) drying the mixture and re-dissolving the mixture in a second metabolism-quenching solution which comprises from 10 v/v % to 100 v/v % a fluoroalcohol, wherein the first metabolism-quenching solution may be the same or different from the second metabolism-quenching solution;
(j) drying the lipids eluted from the solid-phase extraction matrix and/or drying the metabolites collected in steps (e) and/ or (f);
(k) resolubilizing the dried lipids and/or the dried metabolites; and/or
(l) separating the protein precipitate from the solution of step (b) or from the diluted solution of step (c) via centrifugation and/or by filtration.

In some embodiments, this method may be further characterized by one or more of the following features: 1) the protein precipitate is collected; 2) the lipids are eluted from the solid-phase extraction matrix with non-polar, non-aqueous solvents or mixtures comprising one or more of MTBE (methyl tertiary-butyl ether), butanol, methanol, ethanol, dichloromethane, chloroform, or isopropanol; 3) the metabolism-quenching solution further comprises one or more of the following: water, a water-miscible solvent, a detergent, an acid, a base, a salt, or any combination thereof; and/or 4) the metabolism-quenching solution further comprises one or more of the following: acetonitrile, ethanol, methanol, isopropanol, acetic acid, formic acid, medronic acid, phosphate buffered saline, and/or ammonium bicarbonate.

In any of the present methods according to this disclosure, one or more steps may be automated or semi-automated on a liquid-handling platform.

In further aspects, the present disclosure provides kits for performing one or more methods described in this disclosure. The kit may comprise a metabolism-quenching solution comprising, consisting essentially of or consisting of a fluoroalcohol and one or more of the following: a) a well plate with a solid sorbent for capturing lipids in one or more formats: a 96-well plate, a 48-well plate, a 24-well plate, a 12-well plate, a 6-well plate, a 384-well plate and/or a 1536-well plate; and/or b) a carrier with the solid sorbent for capturing lipids. At least some of the kits may further comprise: a well plate for culturing cells, filtering media and/or washing cells in one or more formats: a 96-well plate, a 48-well plate, a 24-well plate, a 12-well plate, a 6-well plate, a 384-well plate and/or a 1536-well plate; wherein the well plate for culturing cells is the same as the well plate for filtering cells or the well plate for culturing cells is different from the well plate for filtering cells. Any of the kits may further comprise a solution for protein precipitation and/or a sorbent-wash buffer, and one or more of elution buffers. Some preferred embodiments of the kit comprise the metabolism-quenching solution comprising the fluoroalcohol in an amount from 10 v/v % to 100 v/v %, based on the total volume of the metabolite-quenching solution and the fluoroalcohol is one or more of the following: 2,2,2-trifluoroethanol, 2,2-difluoroethanol, 2-fluoroethanol, hexafluoro-2-propanol, nonafluoro-tert-butyl alcohol, 1,1,2,2,2-pentafluoroethanol and/or 2,2,3,3,3-pentafluoro-1-propanol. At least some of the kits may also include a PVDF (polyvinylidene), nylon, PTFE (polytetrafluoroethylene), PC (polycarbonate), PP (polypropylene), PES (polyether sulfone), PVC (polyvinyl chloride) CA (cellulose acetate), CMF (coated cellulose acetate), HDPE (high density polyethylene), regenerated cellulose and/or glass fiber filter, and/or a stacked combination of filter types. Any of the kits may further include one or more solutions for protein precipitation and/or a sorbent-wash buffer and a lipid-elution buffer which may comprise one or more of MTBE, butanol, methanol, ethanol, dichloromethane, chloroform, or isopropanol.

BRIEF DESCRIPTION OF THE DRAWINGS

FIGS. 2A and 2D are images of non-lysed cells in PBS; FIGS. 2B and 2E are images of cells lysed and quenched with a solution comprising 50% 2,2,2-trifluoroethanol (TFE); FIG. 2C is an image of cells lysed and quenched with a solution comprising 50% TFE and 0.2% acetic acid; and FIG. 2F is an image of cells treated with a solution comprising a 2:2:1 MeOH:ACN:H$_2$O mixture and 0.1M formic acid.

In FIG. 10, abbreviations are as follows: FA, fatty acid; PI, glycerophosphoinositol; PG, glycerophosphoglycerols; SM, sphingomyelins; PC, glycerophosphocholines; PE, glycerophosphoethanolamines.

DETAILED DESCRIPTION

Figure 1:
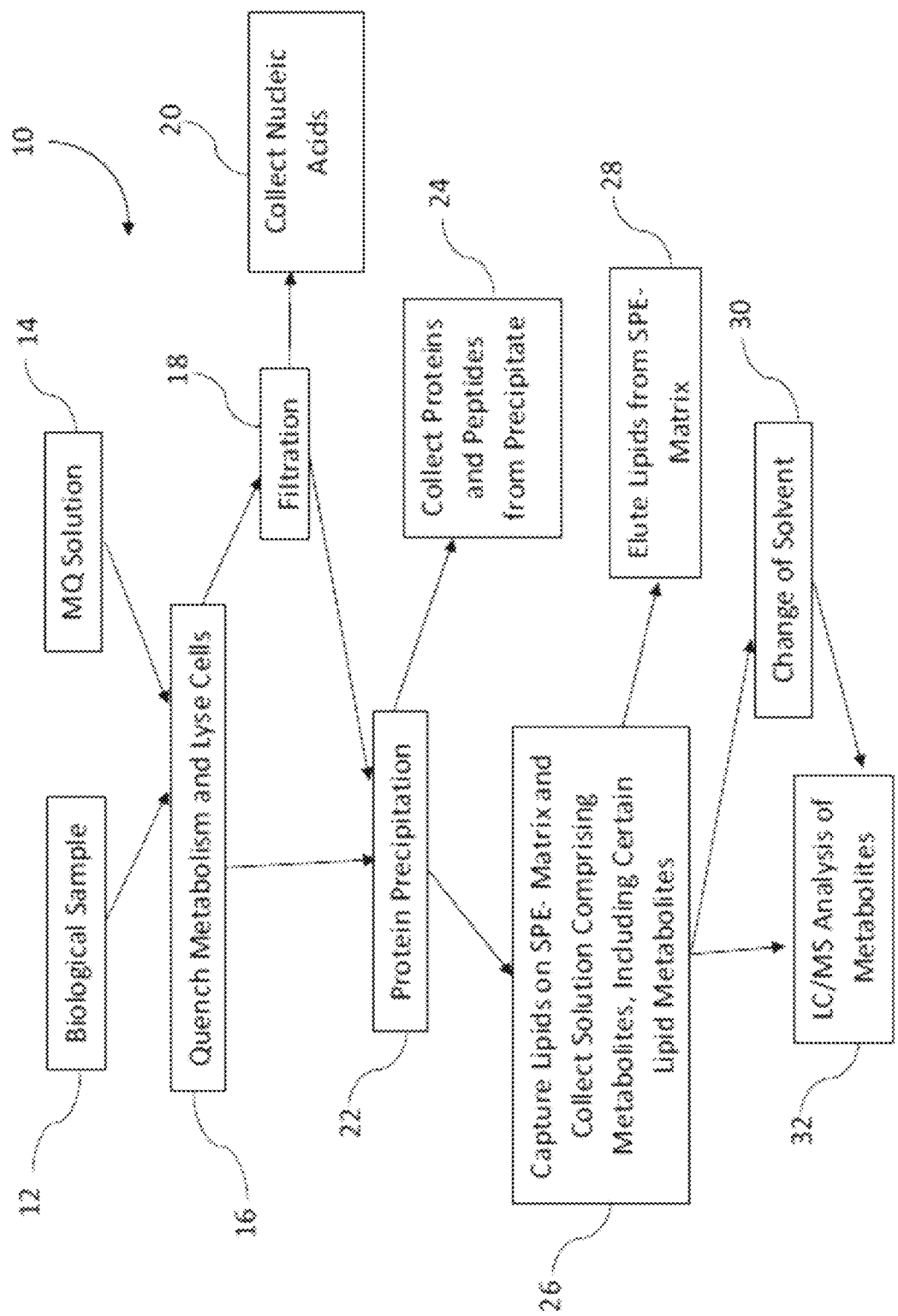
FIG. 1 is a diagram of a unified workflow according to this disclosure.

In one aspect, the present disclosure relates to methods in which metabolites, including polar metabolites and/or lipid metabolites, may be extracted from a biological sample, including biological samples which may comprise cells. In these methods, the biological sample is contacted with a solution comprising a fluoroalcohol at room temperature. The fluoroalcohol inhibits metabolic reactions in the biological sample. If cells are present in the biological sample, the fluoroalcohol also lyses cells. A mixture is extracted from the biological sample with the solution comprising the fluoroalcohol. The mixture comprises polar and lipid metabolites, protected from being a substrate of metabolic reactions, and the mixture further comprises proteins. The metabolites are then separated from the mixture and collected for further analysis.

The mixture may further comprise nucleic acids. In the mixture, metabolic reactions, such as those mediated by enzymes, are quenched (inhibited) with the fluoroalcohol. Accordingly, metabolites, including lipid metabolites, are stabilized. Thus, the metabolites are protected in the mixture. They are blocked from chemical modifications and/or conversions into other compounds at room temperature. The quenching (inhibition) may be partial—the metabolic reactions may be delayed or slowed as compared to a control lysis sample in water or PBS to which no fluoroalcohol or any other metabolism quencher was added. The separation of metabolites from the mixture may be adjusted as needed, depending on metabolites to be analyzed. Some polar metabolites may be separated from lipid metabolites, proteins and/or nucleic acids partially. For example, a polar metabolite fraction may also comprise some lipid metabolites.

In some embodiments of the present methods, any biomolecules such as lipids, proteins, and/or nucleic acids may be also isolated from the same biological sample and analyzed in parallel to polar metabolites or instead of polar metabolites. If information regarding multiple classes of molecules are required in a given study, obtaining that information from a single sample minimizes the amount of sample while improving measurement precision compared to methods that measure different classes of molecules from matched samples of the same type.

Due to the utilization of a room temperature lysis and quenching method, another aspect of the present disclosure is that the present methods for isolating single or multiple cell biomolecules are easy to automate compared to methods that utilize cold or hot temperatures for lysis and quenching.

Due to utilization of a solid phase extraction of polar metabolites and lipid metabolites, another aspect of the present disclosure is that the present methods of isolating cell biomolecules are easy to automate compared to methods that utilize liquid-liquid extraction for cell biomolecule separation.

In this disclosure, the term "metabolites" refer to one or more compounds which are substrates and/or products of a metabolic process (reaction). Metabolites may include substrates and/or products which are produced by metabolic processes (reactions) in a living cell including, but not limited to the reactions of central carbon metabolism, including those involved in glycolysis, tricarboxylic acid cycle (i.e., TCA cycle, Krebs cycle), reductive pentose phosphate cycle (i.e., Calvin cycle), glycogen metabolism, pentose phosphate pathway, among other metabolic processes. Accordingly, metabolites may include, but are not limited to, glucose, glucose-6-phosphate, fructose-6-phosphate, fructose-1,6-phosphate, glyceraldehyde 3-phosphate, dihydroxyacetone phosphate, 1,3-bisphosphoglycerate, 3-phosphoglycerate, 2-phosphoglycerate, phosphoenolpyruvate, pyruvate, acetyl CoA, citrate, cis-aconitate, d-isocitrate, α-ketoglutarate, succinyl CoA, succinate, fumarate, malate, oxaloacetate, ribulose 1,5-bisphosphate, 3-phosphoglycerate, 1,3-bisphosphoglycerate, glyceraldehyde 3-phosphate, ribulose-5-phosphate, ethanol, acetylaldehyde, pyruvic acid, 6-phosphogluconolactone, 6-phosphogluconate, ribose-5-phosphate, xylulose-5-phosphate, sedoheptulose 7-phosphate, erythrose 4-phosphate, among other metabolites.

Metabolites include compounds with various chemical structures from various chemical classes, including, but not limited to, organic acids, sugars, sugar phosphates, amino acids, nucleobases, nucleotides, drug metabolites, steroids, fatty acids and triglycerides. Some of metabolites are lipids or lipophilic compounds, including lipids that have been modified with one or more polar groups during various metabolic reactions. These metabolites may be referred in this disclosure as lipid, polar lipid, or lipid-like metabolites.

Metabolites may include drug compounds and drug metabolites or food compounds and food metabolites. Thus, metabolites in this disclosure include both metabolites naturally produced by a cell and/or an organism and/or xenobiotics.

A xenobiotic is a chemical compound, e.g., an antibiotic, an inactivated steroid, or any drug metabolite, which is present in a biological sample, e.g. urea or blood, but which is not naturally produced or not expected to be present within this biological sample, or not expected to be presented in the amount at which it is present in the biological sample.

The term "metabolic reaction" means any chemical reaction involved in catabolism and/or anabolism. These are any chemical reactions which occur in a living cell.

The term "metabolism" is the sum of all metabolic reactions.

The term "biological sample" refers to a whole organism or a subset of its tissues, cells and/or components (e.g. tissue cell culture, body fluids, including but not limited to blood, plasma, serum, mucus, lymphatic fluid, synovial fluid, cerebrospinal fluid, saliva, bronchiolar lavage, gastric lavage, amniotic fluid, amniotic cord blood, urine, vaginal fluid, semen and feces). A "biological sample" can also refer to intact cells, a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In certain embodiments, the biologic sample has been removed from an animal, plant, and/or fungus.

Biological samples of the present disclosure may comprise cells. The term "cells" is used in its conventional sense to refer to the basic structural unit of a living eukaryotic or prokaryotic organism. In certain embodiments, cells include prokaryotic cells, such as bacteria or archaea. Cells may include eukaryotic cells. Cells may include plant cells or fungal cells. Cells may include, but are not limited to, tissue culture cell lines, bacterial cells, recombinant cells which are cells which have been modified in laboratory by for example, gene editing or by any other means known to a person of skill, yeast cells and/or primary cells which may be obtained from an animal, a human, a plant and/or fungus. Biological sample may comprise fugal cells, cells of the domain archaea, cells comprising a larger biological sample (e.g. cells from a biopsy or tissue sample).

In some of the present methods, a solution comprising a fluoroalcohol is used to lyse a biological sample which comprises cells. By "lyse" cells, it is meant that the cell membranes are at least partially permeabilized such that that at least some of the cell content, including at least some of the metabolites, can leak out from the cell. In some instances, the cell membranes may be ruptured or broken open. In some embodiments, a cell lysis may further include a lysis of cellular organelles, for example the nucleus, mitochondria, ribosomes, chloroplasts, lysosomes, vacuoles, Golgi apparatus, such that the contents of the cellular organelles are also released into the surrounding medium.

The terms "lipids," "proteins," "peptides," "nucleic acids," "DNA," and "RNA" are used in their general meaning as is known to a person of skill.

The term "biological analyte" means any substance that can be analyzed by an analytical procedure, including but not limited to metabolites, lipids, proteins, nucleic acids, amino acids, nucleotides, peptides and/or or any other chemical compounds that are obtained from the biological sample.

In the present disclosure, the term "fluoroalcohol" means an organofluorine compound which comprises a hydroxyl group (—OH) and one or more of fluorine-carbon bonds. Preferably, the fluoroalcohol is an organofluorine compound which comprises a hydroxyl group (—OH) and one or more of fluoroalkyl groups, flouroalkenyl groups and/or fluoroalkynyl groups. Suitable fluoroalcohols include those with terminal and/or internal fluoroalkyl groups, flouroalkenyl groups and/or fluoroalkynyl groups.

Suitable fluoroalcohols may comprise one, two or three fluorine atoms linked to a carbon of an alkyl, an alkenyl or alkynyl as shown by the following formulas (I), (II) and (III):

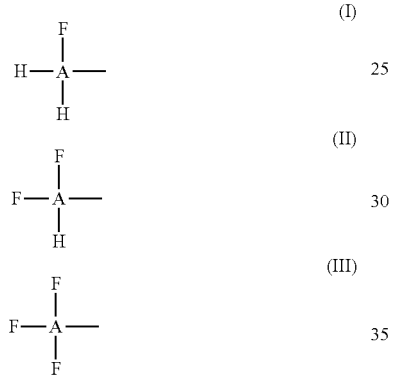

Wherein A is an alkyl, alkenyl or alkynyl;
H is hydrogen, and
F is fluorine.

The "alkyl" in the formulas (I), (II) and (III) may be any of the following: a saturated branched or straight-chain monovalent hydrocarbon radical. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms. Suitable alkyls include fluoroalkyls which contain fluorine atom(s) attached to one or more of internal carbon atoms of an alkyl. Suitable fluoroalkyls include perfluoroalkyls.

The "alkenyl" in the formulas (I), (II) and (III) may be any of the following: an unsaturated branched or straight-chain hydrocarbon radical having at least one carbon-carbon double bond. The group may be in either the cis or trans conformation relative to the double bond(s). Typical alkenyl groups include, but are not limited to, ethenyl; propenyls and butenyls. In some embodiments, an alkenyl group comprises from 1 to 20 carbon atoms. In other embodiments, an alkenyl group comprises from 1 to 10 carbon atoms. In still other embodiments, an alkenyl group comprises from 1 to 6 carbon atoms, such as from 1 to 4 carbon atoms. Suitable alkenyls include fluoroalkenyls which contain fluorine atom(s) attached to one or more of internal carbon atoms of an alkenyl. Suitable fluoroalkenyls include perfluoroalkenyls.

The "alkynyl" in the formulas (I), (II) and (III) may be any of the following: an unsaturated branched, straight-chain hydrocarbon radical having at least one carbon-carbon triple bond. Typical alkynyl groups include, but are not limited to, ethynyl; propynyls and butynyls. In some embodiments, an alkynyl group comprises from 1 to 20 carbon atoms. In other embodiments, an alkynyl group comprises from 1 to 10 carbon atoms. In still other embodiments, an alkynyl group comprises from 1 to 6 carbon atoms, such as from 1 to 4 carbon atoms. Suitable alkynyls include fluoroalkynyls which contain fluorine atom(s) attached to one or more of internal carbon atoms of an alkynyl. Suitable fluoroalkynyls include perfluoroalkynyls.

At least some of the alkyls, alkenyls and/or alkynyls in the formulas (I), (II) or (III) may further comprise one or more additional fluorine atoms located on one or more internal carbon atoms of the alkyl, alkenyl or alkenyl. Examples of such fluoroalcohols include, but are not limited to, 1H,1H, 2H,2H-perfluoro-1-octanol $(CF_3(CF_2)_5CH_2CH_2OH)$ and pentafluoroethanol $(CF_3CF_2OH)$ which can be referred in this disclosure as 1,1,2,2,2-pentafluoroethanol.

The preferred fluoroalcohols of this disclosure include the fluoroalkyl shown in formula (IV):

Wherein each of the R1, R2 and R3 independently is hydrogen, fluorine, an alkyl, a fluoroalkyl, an alkenyl, a fluoroalkenyl, an alkynyl, a fluoroalkynyl or a group defined by the formula (V) as shown below with the proviso that at least one of R1, R2 and R3 is fluorine, a fluoroalkyl, a fluoroalkenyl, a fluoroalkynyl or the group of the formula (V).

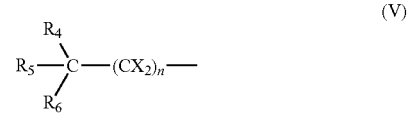

Wherein n is an integer from 0 to 10, and preferably, from 0 to 6, and more preferably from 0 to 4; and Wherein $R_4$, $R_5$, $R_6$, X are independently fluorine or hydrogen with the proviso that at least one of the $R_4$, $R_5$, $R_6$ or X is fluorine. Preferably, each of the $R_4$, $R_5$ and R6 is fluorine.

The preferred fluoroalcohols according to this disclosure include 2,2,2-trifluoroethanol which may be also referred in this disclosure interchangeably, as trifluoroethanol, 2,2,2-trifluoroethan-1-ol or TFE. The preferred fluoroalcohols according to this disclosure further include 2,2-difluoroethanol, 2-fluoroethanol, hexafluoro-2-propanol, nonafluoro-tert-butyl alcohol and 2,2,3,3,3-pentafluoro-1-propanol. In some embodiments, 2,2,2-trifluoroethanol (TFE) is the most preferred fluoroalcohol.

2,2,2-trifluoroethanol (also referred to in this disclosure as trifluoroethanol, 2,2,2-trifluoroethan-1-ol or TFE) has the following formula (VI)

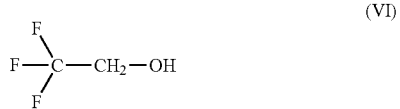

(VI)

Hexafluoro-2-propanol has the following formula (VII)

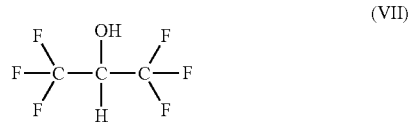

(VII)

Nonafluoro-tert-butyl alcohol has the following formula (VIII)

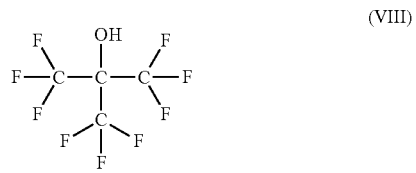

(VIII)

In some embodiments, the present methods can be performed with solutions comprising a cyclic fluoroalcohol. One example of cyclic fluoroalcohols is pentafluorophenol as shown in the formula (IX):

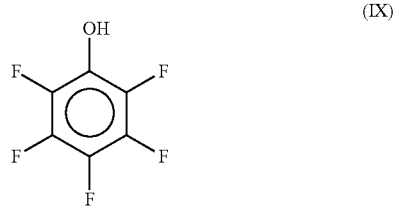

(IX)

In one aspect, the present disclosure provides metabolism-quenching solutions which comprise one or more fluoroalcohols according to this disclosure in an amount from 10 v/v % to 100 v/v %, e.g. if the total volume of the solution is 100 ml, this solution comprises from 10 ml to 100 ml of the fluoroalcohols. In this disclosure, "v/v" means volume per volume. However, if a a fluoroalcohol is solid, then its amount in the metabolism-quenching solution can be measured by weight, e.g. a 10 w/v % solution can be made by dissolving 10 g of the solid fluoroalcohol and adjusting the total volume of the solution to 100 ml. The metabolism-quenching solutions of this disclosure may be made in water and/or they may comprise a water-miscible solvent or a fluoroalcohol-miscible solvent.

The metabolism-quenching solutions of this disclosure quench at least partially (inhibit, delay, or slow down at least partially) at least some of chemical reactions in which a metabolite may be a substrate or product. The metabolism-quenching solutions of this disclosure inhibit at least partially an enzymatic activity of at least some of the enzymes. In addition to quenching enzymes, the metabolism-quenching solutions of this disclosure may stabilize metabolites in mixtures from a biological sample by other means.

The metabolism-quenching solutions may also stabilize lipids and other biomolecules. The metabolism-quenching solutions may further lyse cells if cells are present in a biological sample. The metabolism-quenching solutions of this disclosure may be also referred to as the quenching solutions or as the lysis and quenching solutions. The metabolism-quenching solutions of this disclosure block, suppress and/or otherwise inhibit and/or denature enzymes. The metabolism-quenching solutions inhibit metabolic reactions, including enzymatic reactions.

In some of the metabolism-quenching solutions and methods, the fluoroalcohol is in an amount from 25 v/v % to 75 v/v % of the solution total. In some of the solutions and methods, the fluoroalcohol is in an amount from 45 v/v % to 55 v/v % from the solution total.

The metabolism-quenching solution comprising the fluoroalcohol may further comprise water, water-miscible solvent(s), e.g. acetonitrile (which may be abbreviated in this disclosure as "ACN"), and/or other additives. The additives may include, but are not limited to detergents, acids, bases and/or salts. Examples of acids include, but are not limited to, acetic acid, formic acid and medronic acid. Examples of salts include, but are not limited to, phosphate buffered saline, and ammonium bicarbonate. Water and/or water-miscible solvent(s) can be used in an amount from 0 v/v % to 90 v/v % from the solution total. Additives can be used in any amounts suitable for a particular application, for example from 0.1 v/v % to 20 v/v %, based on the total volume of the solution.

Some of the additives may be used for adjusting and keeping pH of the solution at a predetermined value. In some embodiments, a pH of the solution is in the range from 3.0 to 8.0. Some of the solutions may comprise formic and/or acetic acid and these solutions are acidic. In further embodiments, the metabolism-quenching solution comprising one or more fluoroalcohol according to this disclosure may be prepared in water and its pH may be slightly acidic with no further pH adjustment needed.

The present solutions can be used in combination with other solutions typically used for lysing cells and/or for quenching metabolism, however, one of the technical advantages of the present metabolism-quenching solution is that it is sufficiently efficient in permeabilizing cells and preserving metabolites without the need for additional solutions being added. Thus, there is no need in the present methods to sonicate or electroporate cells in order to release metabolites from the cells.

Preferred metabolism-quenching solutions according to this disclosure may comprise TFE, 2,2-difluoroethanol, 2-fluoroethanol, hexafluoro-2-propanol, nonafluoro-tert-butyl alcohol, 1,1,2,2,2-pentafluoroethanol and/or 2,2,3,3,3-pentafluoro-1-propanol. In some embodiments, the preferred solutions comprise 2,2,2-trifluoroethanol (TFE). Any of the solutions according to this disclosure may be referred in this disclosure as the metabolism-quenching solution or simply as the quenching solution.

While the present methods with the metabolism-quenching solution comprising one or more of the fluoroalcohols of this disclosure can be conducted at a broad variety of temperatures, e.g. any temperature from the freezing temperature of the solution and up to the boiling point of the solution, one of the technical advantages of the present methods is that the methods can be conducted at room temperature. Accordingly, the present metabolism-quenching solutions and methods are well suited for automatization and they are compatible with robotic liquid handlers.

In the present disclosure, the term "room temperature" means a temperature in the range from 1° C. to 30 C, e.g. from 10° C. to 29° C., from 10° C. to 28° C., from 10° C. to 27° C., from 10° C. to 26° C., 10° C. to 25° C., from 10° C. to 24° C., from 10° C. to 23° C., from 10° C. to 22° C., from 10° C. to 21° C., from 10° C. to 20° C., from 10° C. to 19° C., from 10° C. to 18° C., from 10° C. to 17° C., from 10° C. to 16° C., from 10° C. to 15° C., from 10° C. to 14° C., or from 10° C. to 13° C. The room temperature may be a temperature in the range from 15° C. to 25° C., e.g. from 14° C. to 25° C., from 15° C. to 25° C., from 16° C. to 25° C., from 17° C. to 25° C., from 18° C., to 25° C., from 19° C. to 25° C., from 20° C. to 25° C., from 1° C. to 10° C., or from 1° C. to 6° C.

Preferably, the room temperature is a temperature in the range from 15° C. to 30° C., and more preferably in the range from 15° C. to 25° C. and most preferably in the range from 19° C. to 23° C.

In the present methods for extracting metabolites from a biological sample, the biological sample is contacted with the metabolism-quenching solution at room temperature. Typically, the metabolism-quenching solution is used in excess to the biological sample. The duration of the incubation may vary from simply adding the solution to the biological sample, to mixing and incubating the mixture for a period of time. Typically, the volume of the metabolism-quenching solution depends on the volume/weight of a biological sample. Typically, from 1 to 5000 volumes of the solution may be used per one volume or weight equivalent of a biological sample. For example, metabolites can be extracted from about 0.5-3 µl of a biological sample with about 10-200 µl of the solution. For some cell samples, metabolites can be extracted from about 0.5-3 µl of a biological sample with about 1 mL of the metabolism-quenching solution, and the solvent of the resulting metabolite solution can be evaporated and replaced with about 10-200 µl of the metabolism-quenching solution to concentrate the sample.

The ratios between the solution and the biological sample may be adjusted as needed and will depend on many factors, including, but not limited to, the source of the biological sample and other variables, including a concentration and source of the fluoroalcohol in the solution and other additives if present.

The incubation/extraction of the biological sample with the solution can be conducted in any way typically known to a person of skill, including the incubation can be performed with mixing or without mixing. If mixing is needed, then it can be done by pipetting and/or shaking samples hosted on a platform. In some applications, sonication can be used to help lyse cells. For example, a water bath sonicator or probe sonicator can be used to lyse the cells suspended in the metabolism-quenching solution, so that the fluoroalcohol can reach and quench enzymes even faster and/or more completely.

The incubation/extraction period depends on the sample source and volume and may be adjusted as needed. Typically, the incubation/extraction can be completed within 5 seconds to 60 minutes. However, because the metabolism-quenching solution quenches metabolism and preserves metabolites, the mixture can be kept in the solution for a substantial period of time, e.g. overnight.

After the lysis of the biological sample has been completed, metabolites can be separated from the lysis mixture as the lysis mixture may also comprise one or more of the lipids, proteins, peptides and nucleic acids. By separation of metabolites, it is meant that at least some of the metabolites are separated into a fraction from at least some of the lipids, proteins and/or nucleic acids. However, the resulting separated metabolite fraction may still comprise some of the lipids, proteins, peptides and/or nucleic acids and/or other biomolecules.

This can be accomplished by one or more of the following: filtration, protein precipitation, size-exclusion and/or affinity chromatography on a solid-phase extraction matrix, as discussed in more detail below. One of the technical advantages of the present method is that separation can be performed without centrifugation which makes the present methods compatible with an automated workflow. While some automated systems have a centrifuge, these systems may be more expensive, take up more space and are cumbersome to work with. Furthermore, the mixture in the metabolism-quenching solution is a one-phase mixture this expedites the extraction process as there is no need to process every phase separately and no need to separate distinct liquid phases. The one-phase mixture provides a technical benefit over multi-phase mixtures, since multi-phase mixtures are difficult to separate using automation, since it is difficult to identify and individually separate each individual phase.

In one preferred embodiment, a room temperature fluoroacicohol, e.g. 2,2,2-trifluoroethan-1-ol (TFE), solution in water is added to a biological sample, such as a cell pellet, at room temperature. If the sample is a cell pellet, the metabolism-quenching solution lyses the cells as described in connection with FIGS. 2B and 2E. Metabolism is quenched by the solution at room temperature and remains quenched for at least 4 to 24 hours at room temperature (FIGS. 3, 4, 5A, 5B, 6A, 6B, 6C, 6D, 6E, and 7). Samples can be diluted as may be needed. Prior to analysis of the samples by mass spectrometry, the sample can be filtered, for example using a 1 um or 0.2 um filter or a molecular weight cutoff filter, such as 3 kDa, 10 kDa or 30 kDa. The sample can be passed through a C18 SPE, EMR-lipid SPE, or other SPE column to remove larger cell debris, proteins, and/or lipids.

Figure 13A:
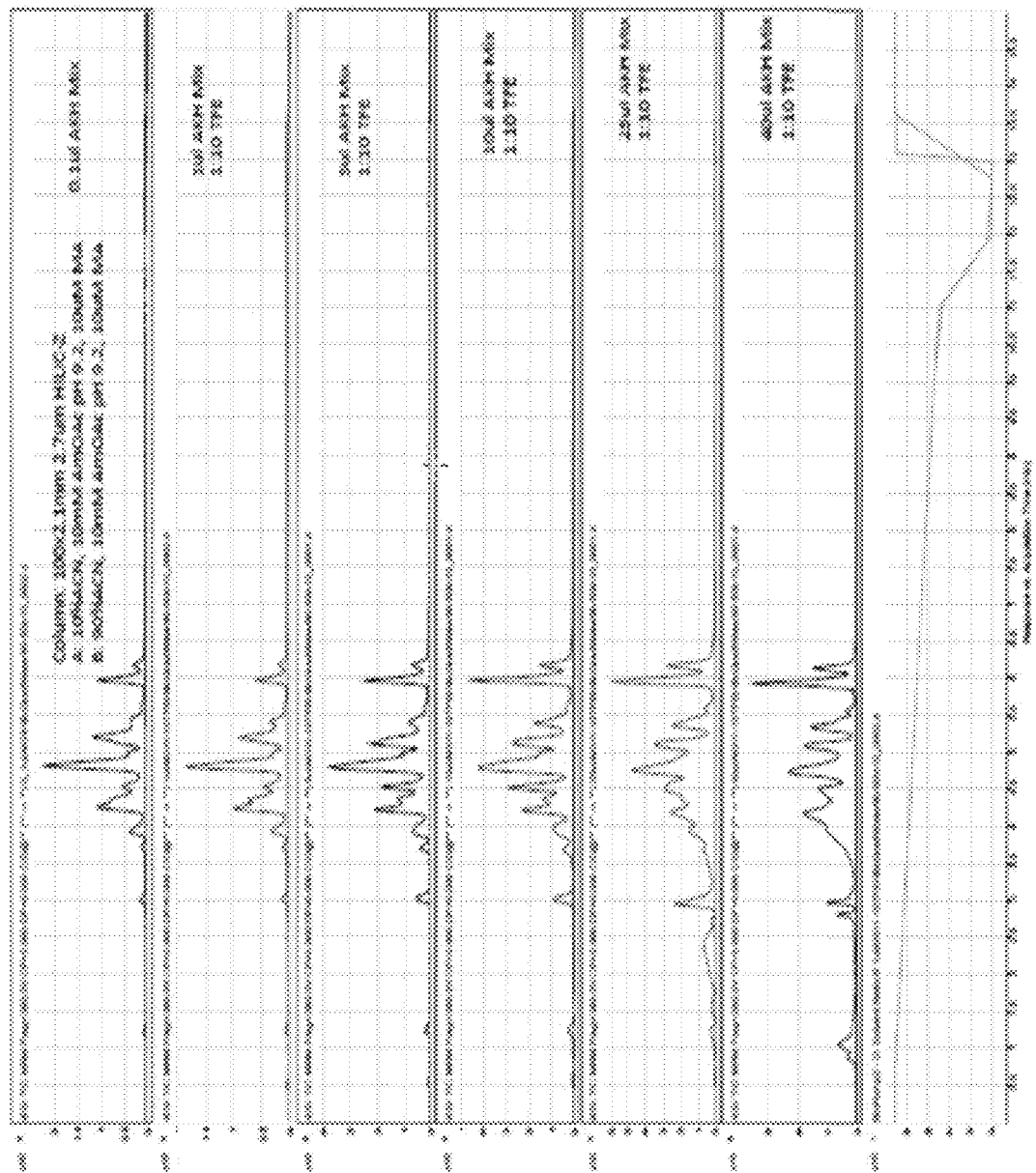
FIG. 13A depicts LC-QQQ MS separation of metabolomic standard mixture by HILIC LC.
Figure 13B:
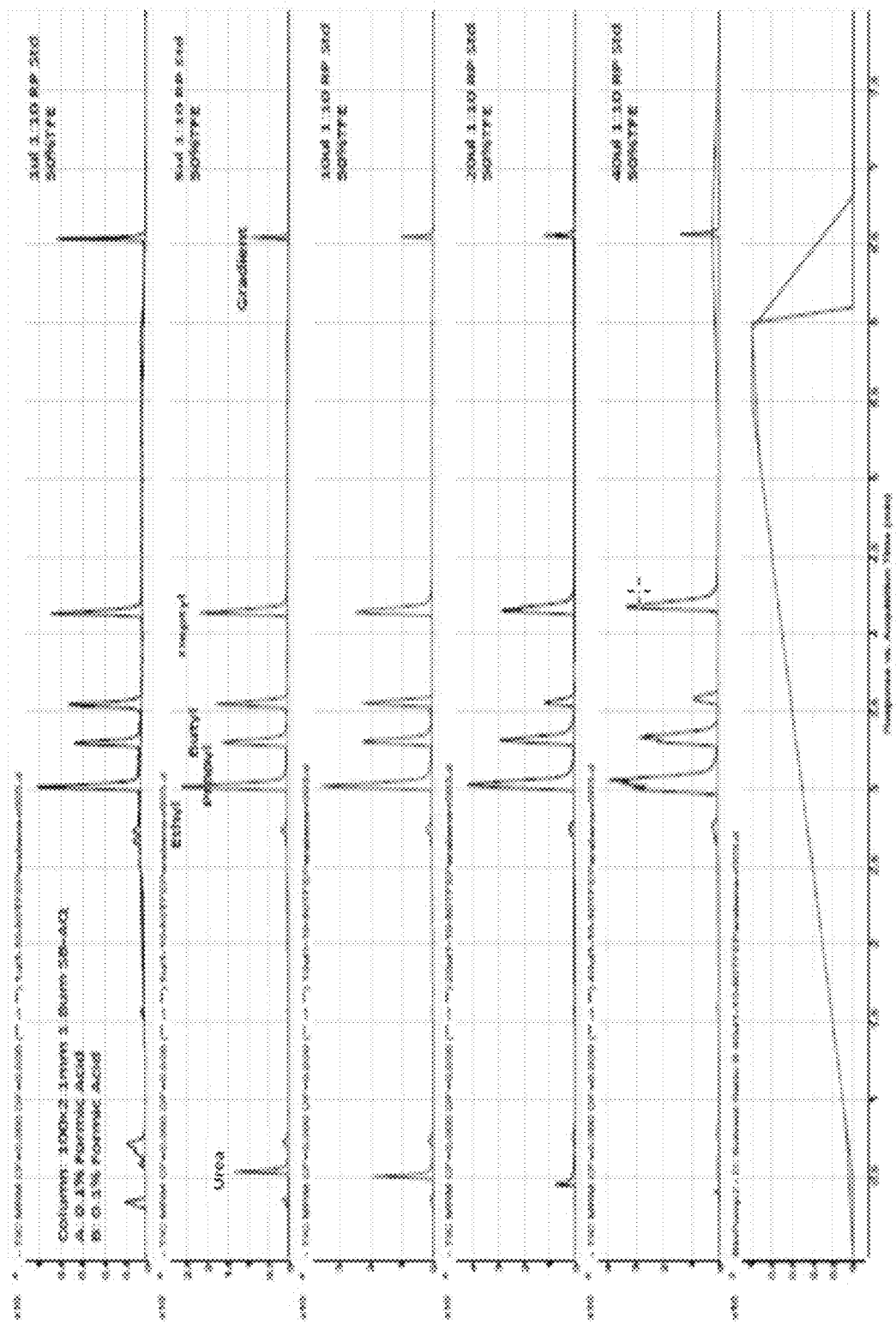
FIG. 13B depicts LC-QQQ MS separation of Reversed Phase Gradient Standard Mixture by Reverse Phase LC.

Furthermore, samples dissolved in specific volumes and percentages of TFE can be introduced directly onto reversed phase or HILIC separations without degradation of resolution. FIG. 13A shows chromatograms of a metabolomics standard following injection of up to 40 µl of the metabolomics standard in 90% TFE without loss of resolution, except due to column overloading. FIG. 13B shows chromatograms of a reverse phase standard mixture following injection of up to 40 µl of the reverse phase standard mixture in 50% TFE without loss of resolution for smaller injection volumes.

Referring to FIG. 1, this is a block diagram for one embodiment of a unified workflow according to this disclosure, generally 10. The unified workflow can be scaled up or down as may be needed. For example, the unified workflow method can be conducted in an microsample format or in a well-plate format or by using Eppendorf test tubes. The method can be performed in a 96-well plate. The unified workflow can be conducted at room temperature in an automated or manual mode. Furthermore, while metabolites, proteins, lipids and nucleic acids can be extracted from one single sample by the present method, in further modifications of the method, only metabolites and one or more of proteins, lipids and nucleic acids can be isolated and analyzed, as may be needed for any particular application. In further embodiments of the method, a user can perform this method and isolate components of the sample that are not metabolites (or polar metabolites), e.g. just the lipids or just proteins and/or DNA, etc.

A biological sample such as for example cells, 12, is contacted at room temperature with the solution comprising one or more of fluoroalcohols according to this disclosure, which may be referred in this disclosure as the metabolism-quenching (MQ) solution, 14. This results in the lysis of the biological sample and quenching of metabolites, and produces a mixture comprising metabolites and one or more of the proteins/peptides, lipids and/or nucleic acids, at block 16. At block 16, the MQ solution also precipitates at least some of the proteins/peptides from the mixture. These protein precipitates may be removed from the mixture by one or more methods by which a solid material is separated from liquid, such as for example, centrifugation and/or filtration. The protein precipitates can be further analyzed.

The metabolites in the mixture are protected from being a substrate for metabolic reactions. By being protected it is meant that at least some enzymes are inactivated at least partially in the mixture and at least some metabolic reactions are inhibited. Accordingly, at least some metabolites are protected (quenched) at least partially for at least a period of time from being a substrate in a metabolic reaction.

The biological sample can be prepared prior to being contacted with the MQ solution. For example, cells can be pelleted (i.e. via centrifugation) and optionally washed and/or resuspended in a suitable buffer. For example, cells can be filtered via a filter plate to remove cell media and optionally washed with a suitable buffer. For example, the cell culture media can be removed from adherent cells, and a wash buffer, such as PBS or isotonic ammonium bicarbonate can be added and removed (fully or partially) from the cells.

Optionally, the mixture from block 16 can be filtered at block 18 or this step can be omitted. Suitable filtration methods may employ a membrane filter, PVDF (polyvinylidene), nylon, PTFE (polytetrafluoroethylene), PC (polycarbonate), PP (polypropylene), PES (polyether sulfone), PVC (polyvinyl chloride), CA (cellulose acetate), CMF (coated cellulose acetate), HDPE (high density polyethylene), regenerated cellulose and/or glass fiber filter or a stacked combination of filter types with appropriate pore size for the sample being used. Other filter types may be used too. In some applications, the mixture is filtered through a glass fiber filter at block 18. Various glass fiber filters typically used for isolation of nucleic acids can be used. For example, borosilicate glass fiber filter can be used with a various pore size. Typically, a pore size can be in the range from 0.5 μm to 3 μm. The pore size can be adjusted in order to optimize the recovery from a particular biological sample. For microsamples, the filtration can be accomplished in filter plates, e.g. in a 96-well plate or 384-well plate. Glass fiber filter plates are commercially available from many different suppliers.

The filtration can be further optimized as needed and may include application of vacuum and/or pressure. The filtration can also include wash steps wherein additional fluoroalcohol solution, or other solution, is used to wash the filter. This may increase the recovery of metabolites or other components of the lysate.

The pore size of the glass fiber filter can be further optimized, depending on whether nucleic acids, such as DNA and/or RNA need to be analyzed. In some embodiments, glass fiber filers are used uncoated. In other embodiments, glass fiber filters may be coated with a binder in order to improve the binding of nucleic acids (NAs) to the filter. Additives or binders may be also used in order to repel the binding of certain metabolites or other cell components.

Nucleic acids such as DNA and/or RNA collected on the glass filter or otherwise at block 18 can be removed and collected at block 20. One method to remove DNA from the glass filter is to add at block 20 a solution with a low (acidic) pH to protonate the DNA and disrupt some of the bonding interactions between the DNA and glass. Another commonly used method is to elute DNA and/or RNA with a low salt buffer. Low salt buffers can be made using high (about 1M) concentrations of EDTA. Purified, deionized water, which has salt ions removed, is another low salt buffer.

Filtration at block 18 may be set up such that while nucleic acids are captured, the other components of the lysed biological sample (proteins, lipids, and metabolites) flow through.

After filtration at block 18 or if filtration is omitted, then directly from block 16, the flow through lysate solution comprising proteins, lipids, and metabolites may be optionally subjected to protein precipitation at block 22. This additional protein precipitation at block 22 may be conducted in some embodiments in order to supplement protein precipitation at block 16.

If protein precipitation is conducted at block 22, the flow through lysate solution from block 16 or from block 18 is contacted with an organic solvent to precipitate protein/peptide material. The solvents used most often for the protein precipitation are 1:1 ethanol:acetonitrile, 1:1 ethanol:methanol, and/or ethanol. However, other solvents and other mixtures of solvents can also be used. In some embodiments, the volume of the protein precipitation solvent is preferred to be two times the volume of the metabolism quenching solution The protein precipitate obtained with the MQ solution at block 16 or at block 22, if this additional protein precipitation is performed, can be collected on a filter, while the solution comprising lipids and metabolites passes through the filter. The protein precipitate can be also collected in conjunction with solid-phase extraction (SPE) of lipids. In these applications, protein precipitates either directly from block 16 or from block 22 are collected at the surface of an SPE-column comprising a matrix which binds lipids. In alternative, protein precipitates can be collected on a filter that is covering the surface of the SPE-column matrix. In alternative, the protein precipitates can be collected by centrifugation and removal of the supernatant solution comprising metabolites and lipids. The protein precipitate collection via centrifugation can be performed with or without the protein precipitation step of block 22. Our current understanding, although with limited evidence, is that the protein precipitation (block 22) enhances the amount of proteins in the precipitate. It has been unexpectedly discovered that addition of the MQ solution at block 16 can precipitate a relatively large number of proteins. Thus, fluoroalcohol solutions can be the solution used for protein precipitation at the same time as biological sample lysis takes place at block 16.

Various SPE-matrixes are known. A hydrophobic matrix that separates lipids from metabolites based at least in part on the affinity of the lipids to the hydrophobic matrix is a preferred matrix in the present methods because it allows for robust separation of polar metabolites from the lipids. Suitable SPE matrix includes solid phase sorbents described in US Patent publication 2018/0080858. Commercially available SPE-columns and plates can be also used. One of the commercially available product families for capturing lipids and separating metabolites from the lipids is the CAP- TIVA™ EMR-lipid SPE columns and plates available from Agilent Technologies, Santa Clara, CA, USA. Other commercially available sorbents can be also used.

If proteins/peptides need to be analyzed, the protein precipitates from block 16 and/or block 22 can be collected at block 24. The protein precipitates can be washed off the surface of the EMR-lipid column or plate (or any other filter or membrane) and transferred to a new vessel for processing. The protein precipitates can also be re-dissolved on top of the EMR-lipid column or plate with a suitable buffer and either pipetted off the surface of the EMR-lipid column or plate (or any other filter or membrane) and transferred to a new vessel for processing or passed through the matrix that binds lipids for collection. This may be accomplished before or after the lipids are removed from the matrix which binds lipids. Alternatively, the protein precipitate can be collected by centrifugation of the sample before interaction with the EMR-lipid column or plate, wherein the supernatant from centrifugation is passed through the EMR-lipid column or plate and the protein pellet is prepared using standard proteomics sample preparation methods.

If the protein precipitate was captured on a filter or on the lipid-binding column, it does not need to be pelleted by centrifugation. In alternative, at block 24, protein precipitates from block 16 and/or from block 22 can be pelleted by centrifugation and re-dissolved in a solvent or processed using standard protein sample preparation. The re-dissolved proteins may be further separated into fractions if needed. A proteomics analysis can be conducted on the proteins collected at block 24 by using trifluoroethanol based protein preparation methods and LC/MS analysis. FASP, PASP, and S-trap proteomics preparations may be used. For example, a suitable protocol can be found in Chapman et al. 2013 ("Plant proteogenomics: From protein extraction to improved gene predictions" in Proteomics for Biomarker Discovery. V. 1002; pp 267-294)

Solvents that may be used to re-dissolve the protein precipitate and wash the EMR-lipid column or plate are trifluoroethanol or heptafluoroisopropanol. Other solvents or buffers suitable for dissolving proteins can be also used, e.g. 5-7% SDS or 6M urea in 50 mM TEAB.

After the protein precipitation at block 22, metabolites are separated from lipids at least partially by capturing at least some of the lipids on a solid-phase extraction (SPE) matrix at block 26. For this procedure and/or for the protein precipitation, the cell lysates may be diluted with water and/or a solvent suitable for protein precipitation.

In various embodiments, the proteins might be captured in several ways, including: 1) centrifugation after protein precipitation and/or after solution dilution and before removal of the lipids on the EMR-lipid material; and/or 2) addition of a solution to the top of the EMR-lipid material or filter covering the EMR-lipid material that allows a user to pipet the protein precipitate off the top of the EMR-lipid material; and/or 3) addition of a solution that dissolves the protein precipitate on top of the EMR-lipid material or filter covering the EMR-lipid material, allowing a user to either pipet off the dissolved protein solution or to push the dissolved protein solution through the EMR-lipid material, possibly with a filter, and collect the eluate.

At block 26, the metabolites and lipids flow through the EMR-lipid column or plate, and the column captures the lipids and provides a solution containing predominantly polar metabolites, which is used for a metabolite analysis. It should be noted under some purification conditions, some lipid compounds such as short-chain fatty acids and sterols can be found in the solution with metabolites, including polar metabolites.

Figure 9A:
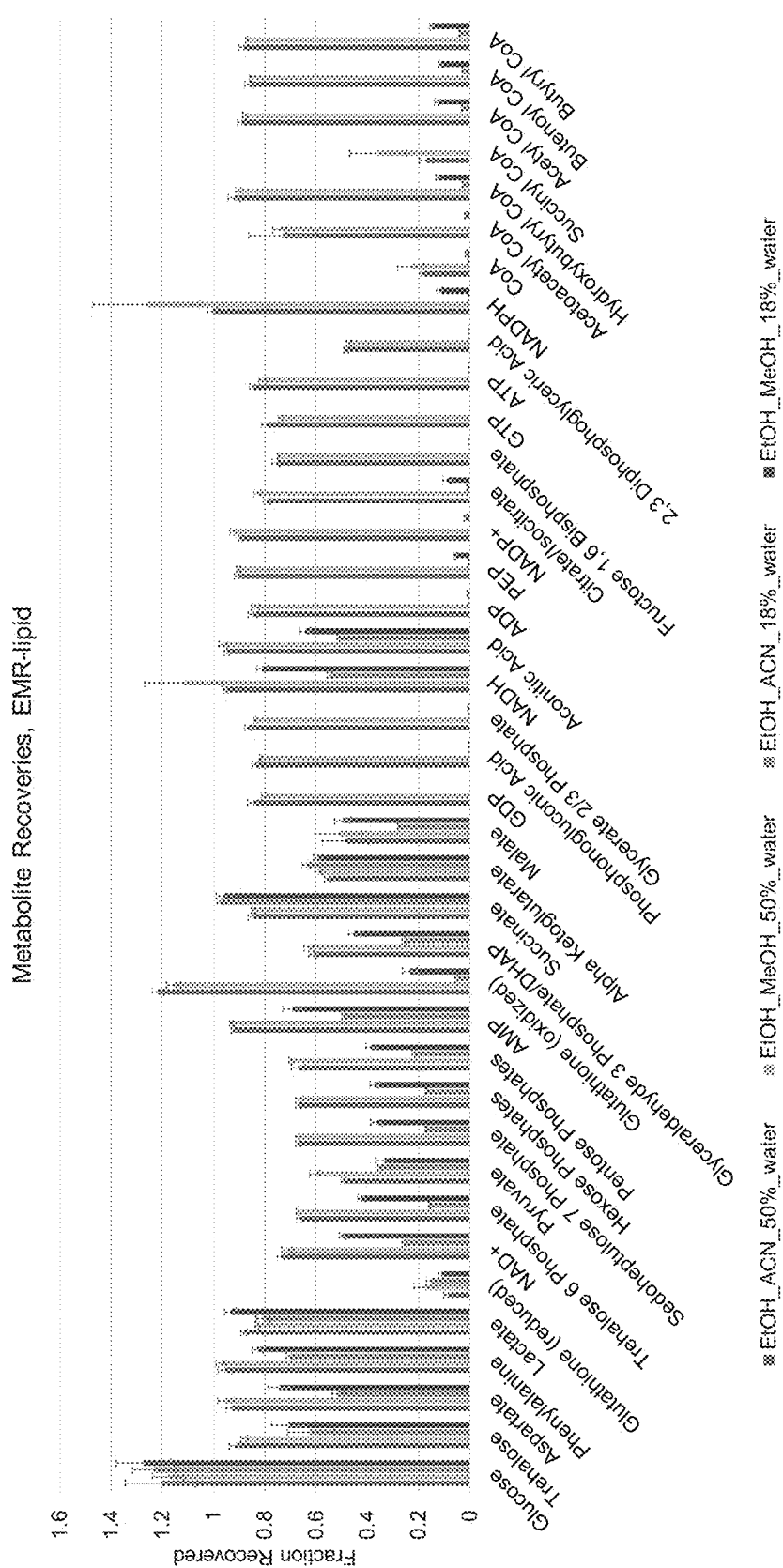
FIG. 9A reports metabolite recovery for metabolites passed through a CAPTIVA™ EMR-lipid SPE plate with various solvent compositions.
Figure 9B:
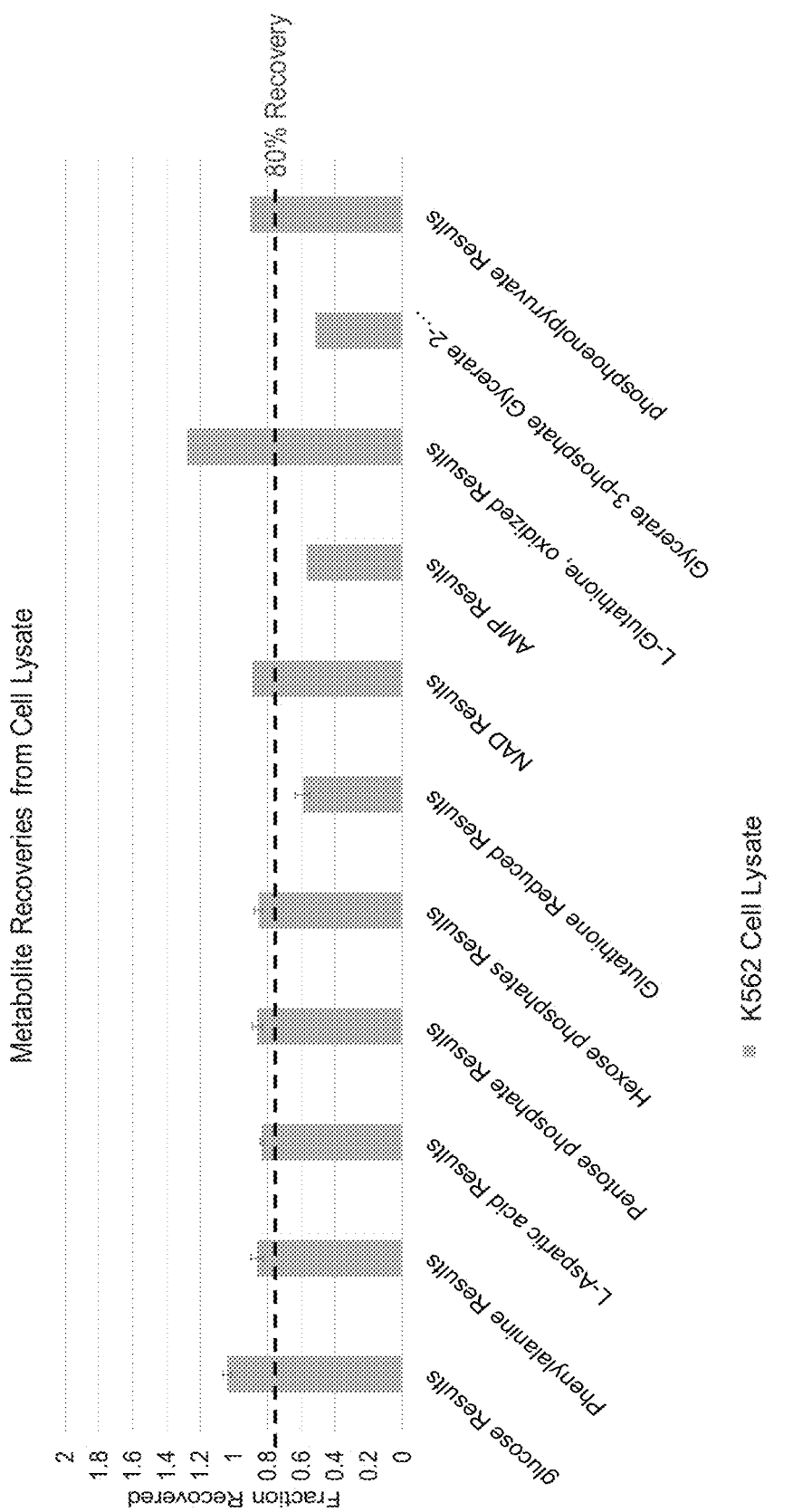
FIG. 9B reports metabolite recovery for metabolites from mammalian cells lysed, quenched and extracted with 50% TFE. Proteins were removed from the cell lysates by precipitation, and the cell lysates comprising quenched metabolites were then passed through a CAPTIVA™ EMR-lipid SPE plate.
Figure 10:
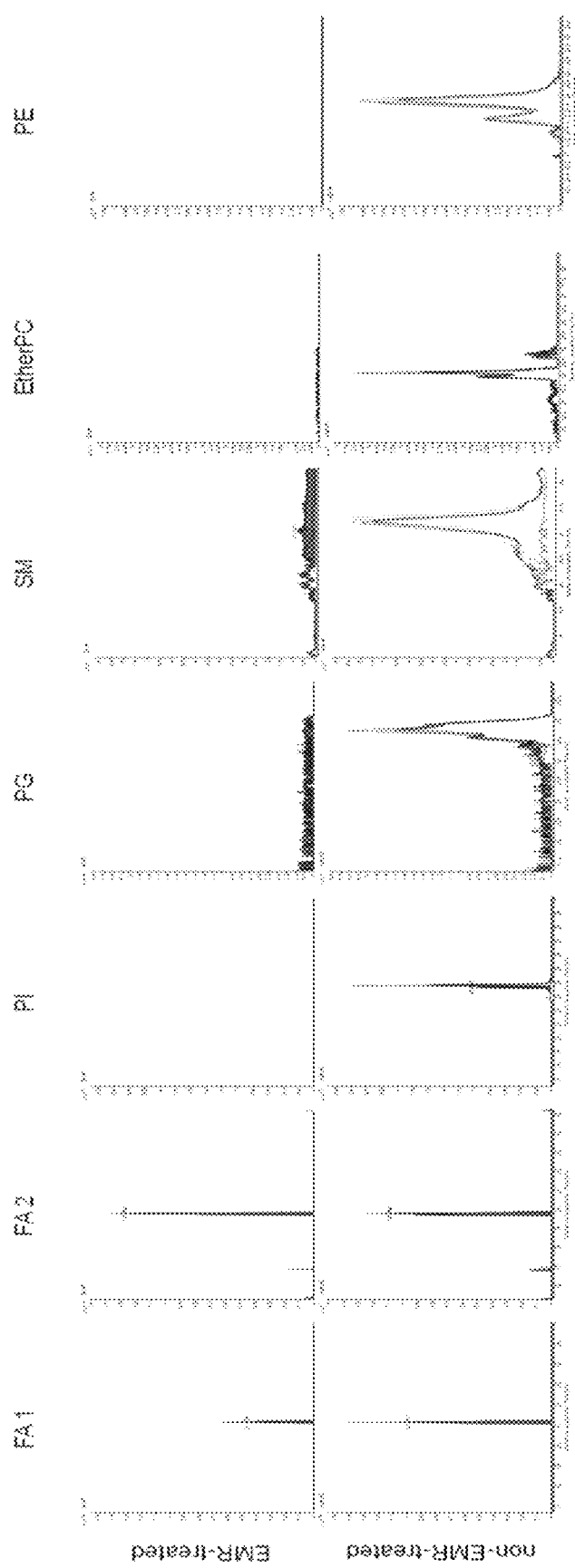
FIG. 10 reports the removal of lipids by the EMR-lipid SPE matrix from cell lysates that are dissolved/suspended in a solution that has been optimized for improved recovery of metabolites from the EMR-lipid SPE matrix.

Many solutions were tested to optimize metabolite recovery when using the EMR-lipid SPE material, and a solution with roughly 50 v/v % water and 50 v/v % an organic water-miscible solvent was found to provide good metabolite recovery, as shown in FIGS. 9A and 9B and as described in more detail in Example 5. The 50 v/v % water, 50 v/v % organic water-miscible solvent solutions maintain good lipid capture on the EMR-lipid material, as shown in FIG. 10 and as described in more detail in Example 6. After the initial sample is passed through the EMR-lipid SPE column, a wash buffer may be passed through the column to increase metabolite recovery. The wash solution is also optimally roughly 50% water and 50 v/v % an organic water-miscible solvent.

In further embodiments, a solvent comprising from 10 v/v % to 90 v/v % of an organic water-miscible solvent can also be used. Suitable organic water-miscible solvents include, but are not limited, to acetonitrile, ethanol, methanol, isopropanol, formic acid, acetic acid or any mixtures thereof. It has been found that if at least 10% water is present, the lipids are retained on the EMR-lipid sorbent.

At block 26, the lipids that are captured within the EMR-lipid column are subsequently recovered from the EMR-lipid cartridge or plate at block 28, so that the lipids can be also analyzed. This lipid recovery might happen either before or after the proteins are removed from the filter/EMR-lipid material or re-dissolved and passed through the filter and/or the EMR-lipid material.

At block 28, the lipids can be released from the EMR-lipid column using organic solvents to provide the lipid fraction of the cell lysate sample. Suitable solvents include a mixture of 1:1 chloroform:methanol and 2:1 methanol:dichloromethane. Other suitable solvents include non-polar, non-aqueous solvents or mixtures such as MTBE, butanol, methanol, ethanol, dichloromethane, chloroform, isopropanol or their mixtures. Since the organic solvents used for lipid recovery can leach compounds from plastic materials and/or melt plastic materials, the collection vessel may need to be glass or glass-lined for optimal results.

After the metabolites are collected in the flow through solution at block 26, they can be analyzed by liquid chromatography/mass spectrometry (LC/MS) at block 32. If needed, a solvent can be changed for the metabolite analysis at block 30 prior to the analysis at block 32. This also applies to the lipid fraction of the sample, and it could apply to the protein and nucleic acid fractions as well. The solvent change also provides an opportunity to make the metabolite sample more concentrated, so low-abundance metabolites are more easily detected by LC/MS.

LC/MS and other methods for analysis can also be used for lipids, proteins/peptides, and nucleic acids. In the diagram of FIG. 1, the LC/MS analysis is listed. However, the metabolites obtained in the present methods can be analyzed by any other methods typically used for analyzing metabolites and as discussed in more detail below.

The present unified workflow methods provide many technical advantages over other methods previously used for obtaining metabolites and/or proteins and/or lipids. The present methods collect and analyze, by mass spectrometry or other analysis methods, nucleic acids, proteins, lipids, and metabolites from single samples, wherein each cellular component is measured from the same group of cells, which is distinct from measuring each of these cellular components from different aliquots of cells that originate from the same biological sample. By using the same exact cells to prepare extracts of each cellular component, the correlative analyses can be accurately made between different cellular subtractions. For example, this sample preparation workflow can help with improving the understanding of how genetic changes lead to protein expression changes and how these impact lipid and metabolite levels. In addition, making multiple measurements on the same sample enables customers to use less of a total sample. This preserves rare or limited samples.

The methods provided in this disclosure eliminate the need for cold or hot metabolism quenching solutions, overnight cold temperature protein precipitation and also avoid the need to separate biphasic liquid-liquid extraction solutions, which is needed in other methods, such as the Weckwerth method.

Metabolites obtained by the methods according to this disclosure can be analyzed by many different methods, including analytical methods. These methods can help with detecting and monitoring the metabolic impact of newly developed therapeutics; measuring disease biomarkers; optimizing chemical production by measuring a metabolic flux; and understanding the impact of environment on organisms. Further applications may include detection of toxins, drugs and their metabolites in a human sample.

The analytical methods include, but are not limited to, analyzing metabolites by liquid chromatography and/or mass spectrometry systems. The analysis may include liquid chromatography (LC), including a high-performance liquid chromatography (HPLC), a micro- or nano-liquid chromatography or an ultra-high-pressure liquid chromatography (UHPLC). The analysis may also include liquid chromatography/mass spectrometry (LC/MS), ion mobility—mass spectrometry, gas chromatography/mass spectrometry (GC/MS), capillary electrophoresis (CE), capillary electrophoresis chromatography (CEC), and/or supercritical fluid chromatography-mass spectrometry (SFC/MS).

Mass spectrometer systems for use in the subject methods may be any convenient mass spectrometry system, which in general contains an ion source for ionizing a sample, a mass analyzer for separating ions, and a detector that detects the ions. In certain cases, the mass spectrometer may be a so-called "tandem" mass spectrometer that is capable of isolating precursor ions, fragmenting the precursor ions, and analyzing the fragmented precursor ions. Such systems are well known in the art (see, e.g., U.S. Pat. Nos. 7,534,996, 7,531,793, 7,507,953, 7,145,133, 7,229,834 and 6,924,478) and may be implemented in a variety of configurations. In certain embodiments, tandem mass spectrometry may be done using individual mass analyzers that are separated in space or, in certain cases, using a single mass spectrometer in which the different selection steps are separated in time. Tandem MS "in space" involves the physical separation of the instrument components (QQQ or QTOF) whereas a tandem MS "in time" involves the use of an ion trap or Fourier transform Ion Cyclotron Resonance Mass Spectometer (FT-ICR MS).

An example mass spectrometer system may contain an ion source containing an ionization device, a mass analyzer and a detector. As is conventional in the art, the ion source and the mass analyzer are separated by one or more intermediate vacuum chambers into which ions are transferred from the ion source via, e.g., a transfer capillary or the like. Also as is conventional in the art, the intermediate vacuum chamber may also contain a skimmer to enrich analyte ions (relative to solvent ions and gas) contained in the ion beam exiting the transfer capillary prior to its entry into the ion transfer optics (e.g., an ion guide, or the like) leading to a mass analyzer in high vacuum.

The ion source may rely on any type of ionization method, including but not limited to electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof (to provide a so-called "multi-mode" ionization source). In one embodiment, the precursor ions may be made by EI, ESI or MALDI, and a selected precursor ion may be fragmented by collision or using photons to produce product ions that are subsequently analyzed. Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof. In one embodiment, the mass analyzer may be a sector, transmission quadrupole, or time-of-flight mass analyzer.

The methods provided by this disclosure can be partially or fully automated on a liquid handling platform, such as the BRAVO Automated liquid handling platform (Agilent, Santa Clara, U.S.) and/or a BIOTEK microplate washer (Agilent, Santa Clara, U.S.).

Any of the methods in this disclosure may further comprise one or more of the following steps: 1) evaporating a solvent and/or metabolite-quenching solution in order to dry a sample and then re-dissolving the sample in a different solvent (change of solvent) and/or re-dissolving a sample in a smaller volume of the same or different solvent (sample concentration); 2) drying a sample; 3) concentrating a sample; 4) diluting a sample, e.g. in order to increase a loading volume and/or to change a loading buffer for lipids to a solid-phase extraction matrix (column); 5) washing a column and collecting and combining a wash with a flow-through in order to increase recovery of metabolites.

In some methods of this disclosure, at least some of the steps can be performed simultaneously.

Further aspects of this disclosure include a kit for obtaining a metabolite solution, the kit comprising the one or more metabolism-quenching solutions according to this disclosure. The kit may further include a manual delivering to a user a protocol for performing one or more workflow methods of this disclosure. The kit may further include one or more of the following: a well plate with a solid sorbent for capturing lipids, such as for example, as a 96-well plate, a 48-well plate, a 24-well plate, a 12-well plate, a 6-well plate, a 384-well plate and/or a 1536-well plate. The kit may further include one or more of the following: solutions for protein precipitation (e.g. ethanol:acetonitrile, preferably 1:1 ethanol:acetonitrile, ethanol:methanol, preferably 1:1 ethanol:methanol, and/or ethanol), solutions for washing the EMR-lipid material (e.g. water:ethanol:acetonitrile, preferably 2:1:1 water:ethanol:acetonitrile, and/or water:ethanol:methanol, preferably 2:1:1 water:ethanol:methanol), solutions for eluting lipids from the EMR-lipid material (e.g. chloroform:methanol, preferably 1:1 chloroform:methanol, and/or methanol:dichloromethane, preferably 2:1 methanol:dichloromethane). The kit may further include a well-plate, such as for example, as a 96-well plate, a 48-well plate, a 24-well plate, a 12-well plate, a 6-well plate, a 384-well plate and/or a 1536-well plate for filtering cells from media and/or for culturing and/or washing cells prior to addition of metabolism-quenching solution.

This disclosure also provides the following non-limiting examples and exemplary embodiments.

Example 1. Lysis and Quenching of K562 Leukemia Cells and HTB123 Suspension Breast Cancer Cells with 2,2,2-Trifluoroethan-1-ol (TFE)

Figure 2C:
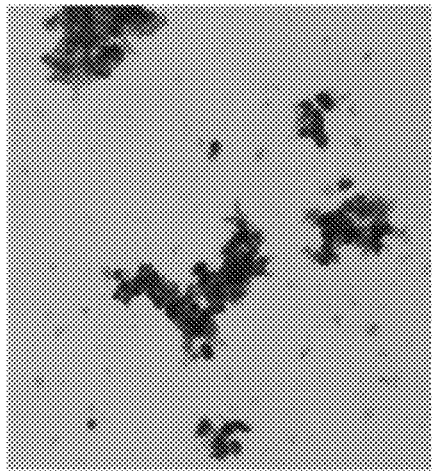
FIGS. 2A-2F are brightfield images of K562 cells (FIGS. 2A-2C) or HTB123 cells (FIGS. 2D-2F). The cells were treated as follows.

After treatment with PBS or a cell lysis solution, cell solutions were diluted 1:1 with trypan blue to stain cells with compromised cell membranes to determine whether cells had been lysed by the cell lysis solutions. Referring to FIGS. 2A-2C, these are brightfield images of K562 cells treated with PBS (FIG. 2A); 50% TFE (FIG. 2B), or 50% TFE+ 0.2% acetic acid (FIG. 2C) at room temperature.

In PBS, the majority of the cells are live and not stained by trypan blue. In 50% TFE, all cells stain with trypan blue, indicating cell lysis. In 50% TFE with 0.2% acetic acid, the cells again stain with trypan blue, indicating cell lysis. When acetic acid is present with TFE, cells appear to aggregate and there appears to be more small cell membrane debris than when the acetic acid is not present. Cell concentration: 500,000 cells/50 µL PBS or cell lysis solution.

Figure 2F:
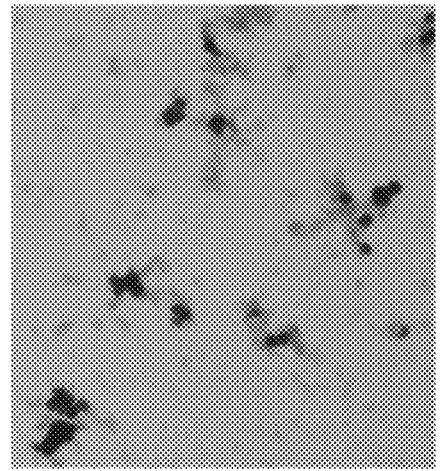
Figure 2B:
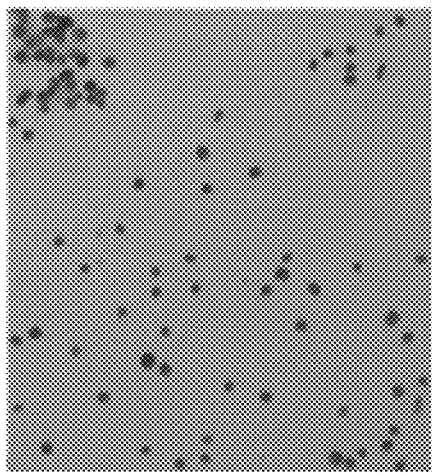
Figure 2E:
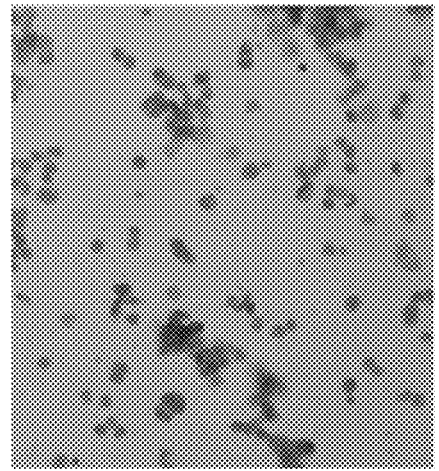
Figure 2A:
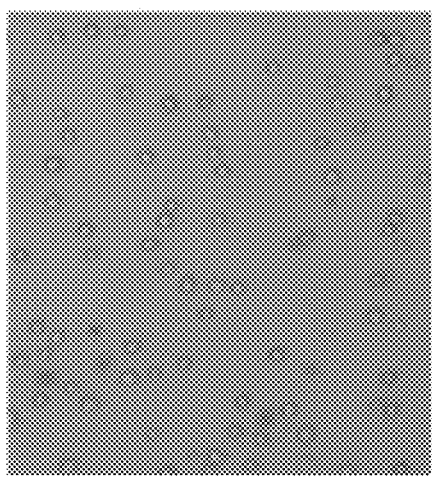
Figure 2D:
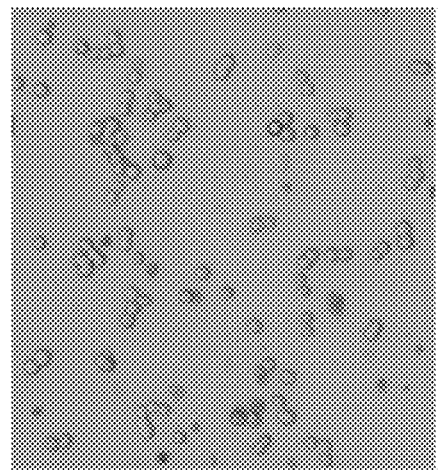

Referring to FIGS. 2D-2F, HTB123 cells were treated with PBS (FIG. 2D), 50% TFE (FIG. 2E), or 2:2:1 MeOH: ACN:water+0.1M formic acid (FIG. 2F).

In PBS, the majority of the cells are live and not stained by trypan blue. In 50% TFE, all cells stain with trypan blue, indicating cell lysis. In 2:2:1 MeOH:ACN:water+0.1M formic acid, the cells stain with trypan blue, indicating cell lysis. The trypan blue stain appears darker for the 2:2:1 MeOH:ACN:water+0.1M formic acid treatment. For the 2:2:1 MeOH:ACN:water+0.1M formic acid condition, cells appear to aggregate slightly and there appears to be more small cell membrane debris than for the TFE condition. Cell concentration: 500,000 cells/50 µL PBS or cell lysis solution.

Example 2. Comparative Analysis of Metabolism Quenching by TFE—ATP Measurements K562 cells in RPMI media with GlutaMAX and 10% FBS were transferred to a 50 mL falcon tube, which was kept in a CO2 incubator until use. Cells were pelleted at 250×g for 5 min, media was removed, and cells were diluted with PBS at 1 million cells/mL. 500,000 K562 cells were pipetted into individual Eppendorf tubes, cells were re-pelleted at 250×g for 5 min at 4° C., the supernatant was removed, and cells were re-suspended in 50 µL PBS, 50% TFE, or 50% TFE+ 0.2% HOAc, or 2:2:1 MeOH:ACN:water+0.1% formic acid. The cell samples were then incubated at room temperature or −20° C. for approximately 20 minutes. To assess the amount of ATP extracted from the cells, a portion of each sample was added to a 96-well plate, diluted with PBS and the ATP content was measured using an ATP assay (CellTiter Glo, One Solution). ATP content was calculated using ATP standard curves made with 50% TFE, 50% TFE+0.2% HOAc, PBS, or 2:2:1 MeOH:ACN:water+0.1% formic acid in an amount equivalent to that in the measured portion of the samples.

Figure 3:
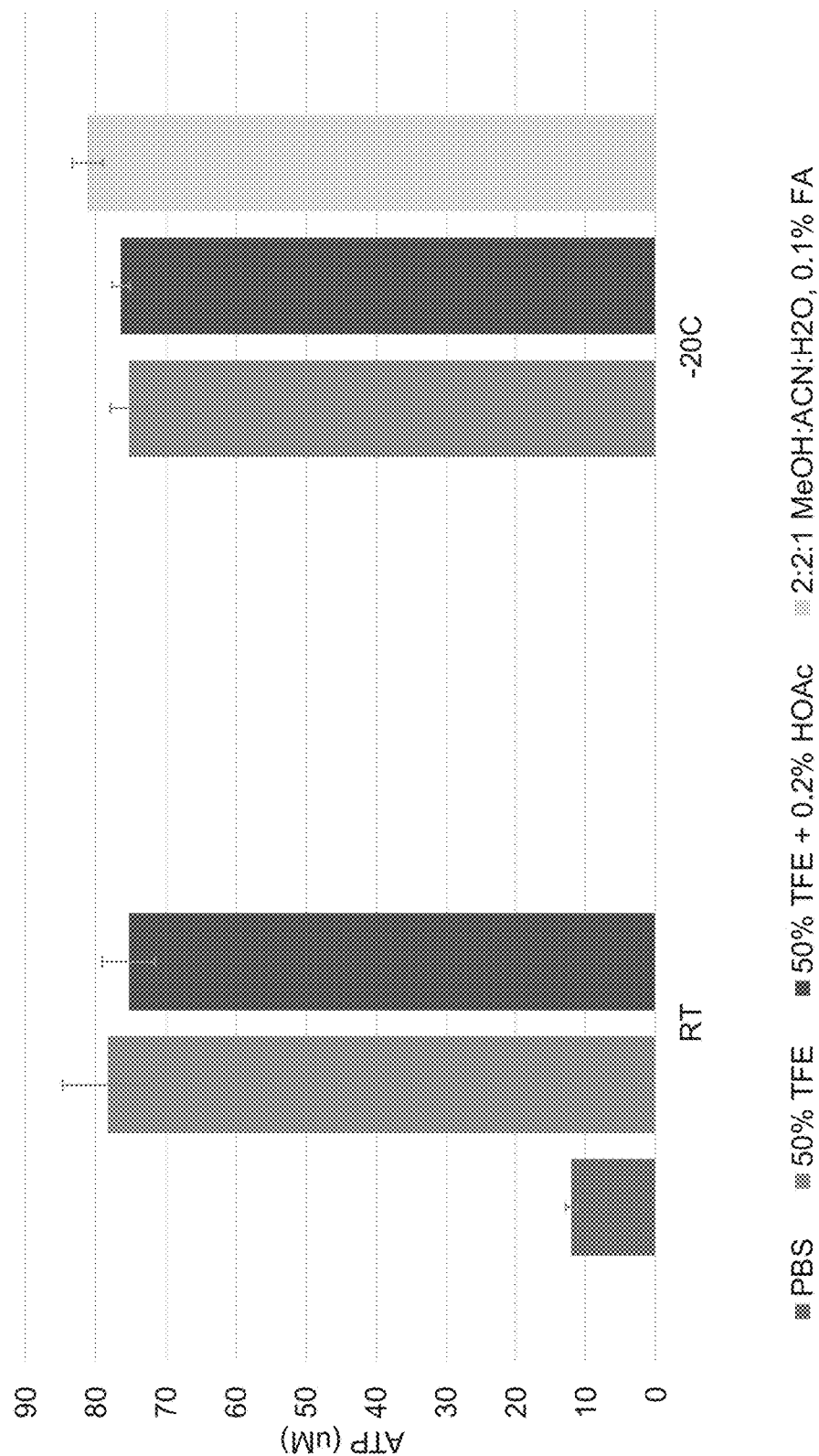
FIG. 3 reports ATP levels in cells lysed at room temperature versus −20° C.

FIG. 3 reports ATP levels in cells lysed at room temperature versus −20° C. and shows that an amount of ATP extracted from cells is equivalent for room temperature (RT) and −20° C. solutions.

K562 cells in RPMI media with GlutaMAX and 10% FBS were transferred to a 50 mL falcon tube and pelleted at 250×g for 5 min at 20° C. The cell media was removed, cells were diluted with PBS at 1 million cells/mL, and 4 million cells (4 mL) were transferred to four 5 mL Eppendorf tubes. The cells were re-pelleted at 250×g for 5 min at 4 C, the supernatant was removed, and cells were re-suspended in 400 µL PBS or cell lysis buffer (cell concentration=500,000 cells/50 µL). Lysis buffer was 50% TFE. The cells suspended in PBS were sonicated using a sonication probe for 1 minute, pulsing the sonicator on and off. The cells were briefly cooled in ice before and after sonication to maintain the temperature near room temperature. The cells with added lysis buffer were vortexed for 5-10 seconds. Samples were divided into 25 µL aliquots and the aliquots (in triplicate) were flash frozen at −40° C. and stored at −80° C. after incubation at room temperature for 5, 60, 120, or 240 minutes. To assess the quenching of metabolism, samples were thawed on ice and a portion of each sample was added to a 96-well plate, diluted with PBS and the ATP content was measured using an ATP assay (CellTiter Glo, One Solution). ATP calibration curves were made containing either PBS or the lysis buffer for calculation of the absolute ATP content. Assays were completed in triplicate.

Figure 4:
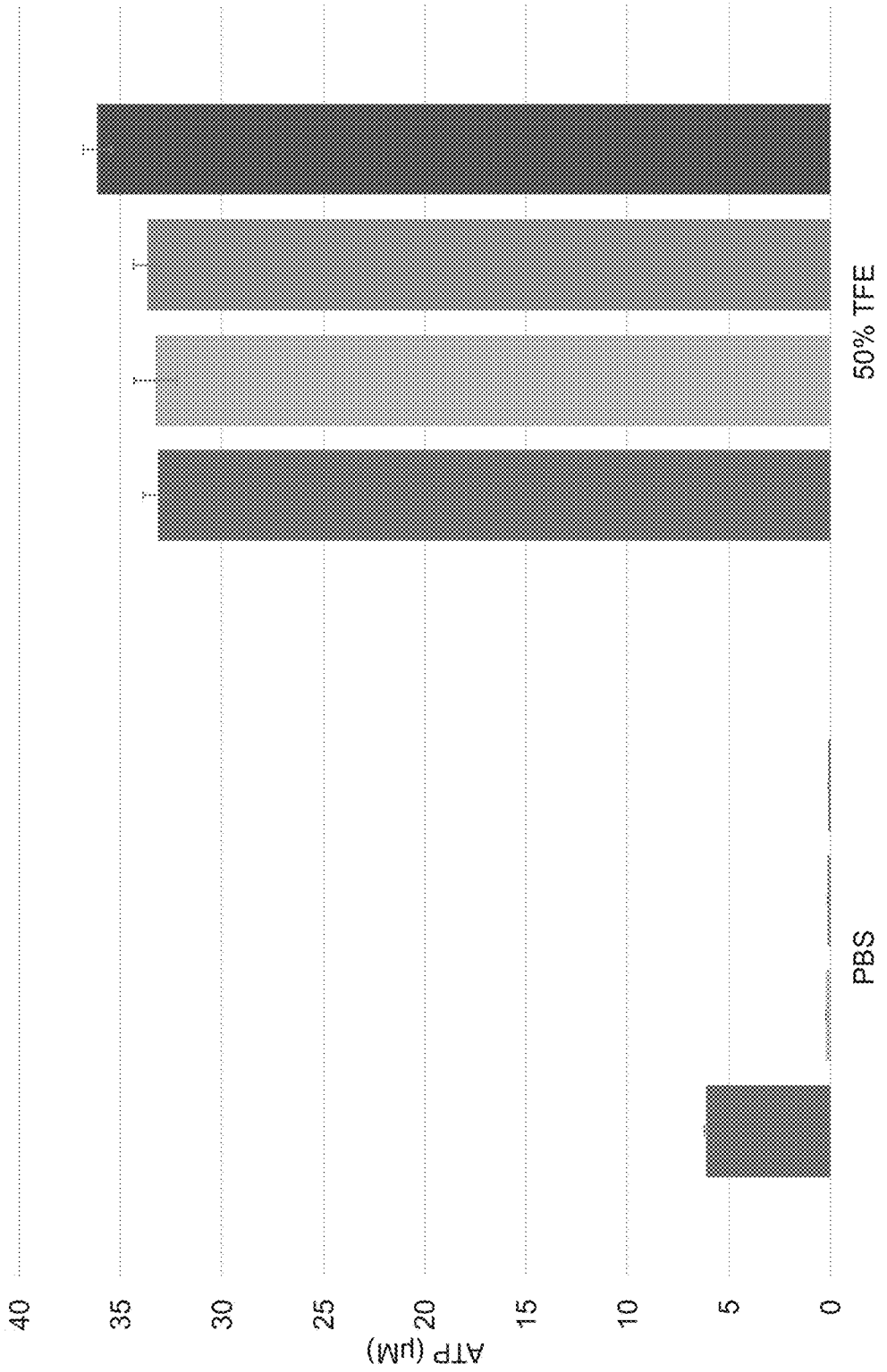
FIG. 4 reports ATP levels in cells lysed and quenched at room temperature with a solution comprising 50% TFE versus in cells sonicated in PBS and in which metabolism was not quenched.

FIG. 4 reports ATP levels for samples that were incubated at room temperature for 5, 60, 120, or 240 minutes and shows that TFE continues to quench ATP metabolism in samples incubated for 240 minutes, while almost no ATP can be detected in PBS control samples.

An additional analytical analysis was conducted to elucidate whether metabolism remains quenched in lysates after dilution of the lysis/quenching solution comprising TFE.

For the samples prepared as discussed in connection to FIG. 4, a 40 µL portion of each cell sample was diluted with 360 µL PBS to make dilute samples. Samples were then divided into 25 µL aliquots and the aliquots (in triplicate) were flash frozen at −40° C. and stored at −80° C. after incubation at room temperature for 5, 60, 120, or 240 minutes. To assess the quenching of metabolism, samples were thawed on ice and a portion of each sample was added to a 96-well plate, diluted with PBS and the ATP content was measured using an ATP assay (CellTiter Glo, One Solution). ATP calibration curves were made containing either PBS or a TFE solution for calculation of the absolute ATP content. Assays were completed in triplicate.

Figure 5:
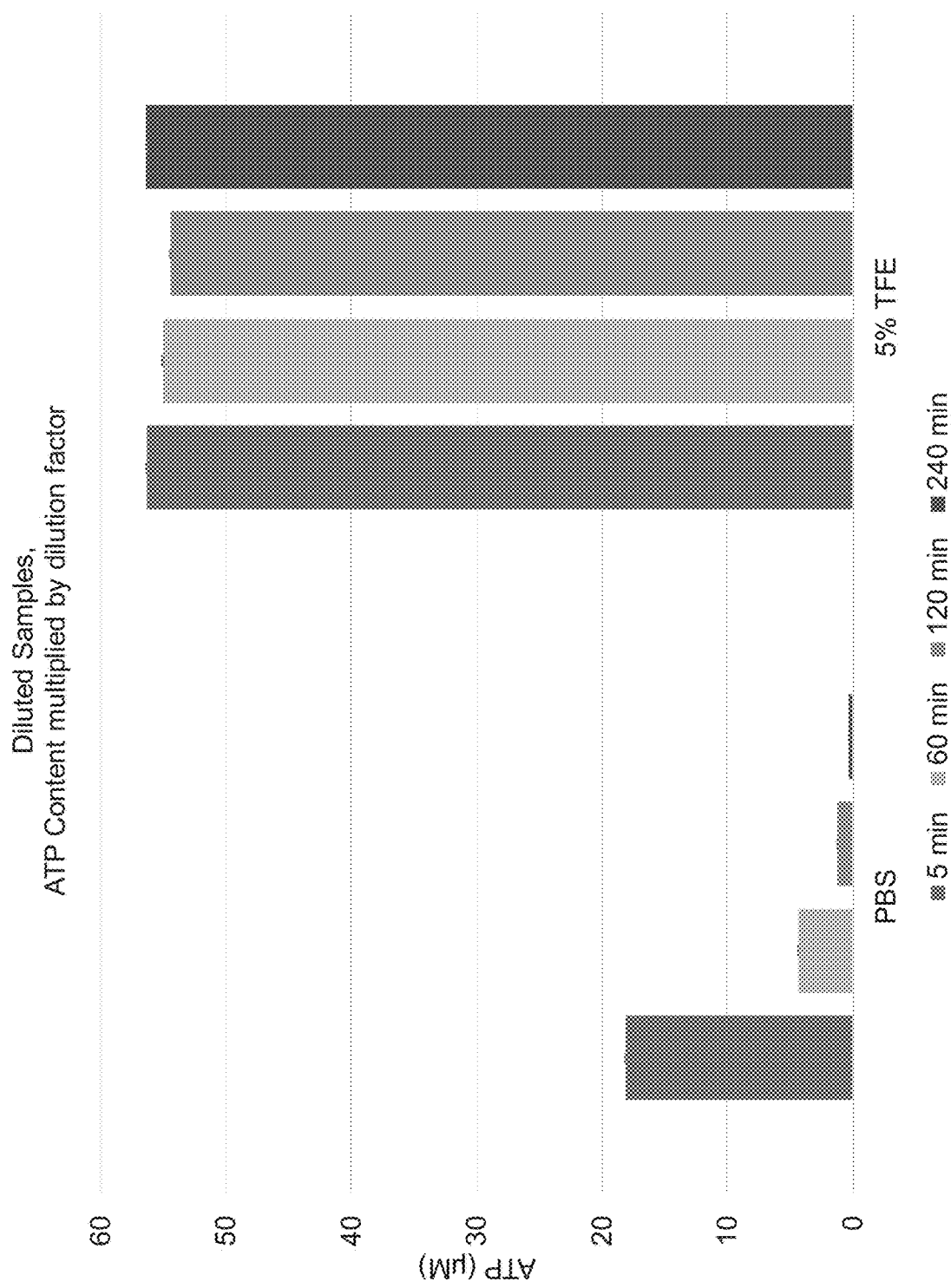
FIG. 5 reports ATP levels in a 10× diluted sample of FIG. 4 from lysates quenched with a solution comprising TFE versus in cells sonicated in PBS and in which metabolism was not quenched. For the diluted sample, cells were initially lysed and metabolism was quenched using 50% TFE. After this, the TFE was diluted ten-fold to 5% and ATP levels were measured from samples that were kept at room temperature for 5, 60, 120, or 240 minutes.

FIG. 5 reports that the ATP levels remain stable after 10× dilution of the lysis/quenching solution comprising TFE in comparison to a concentrated sample as shown in FIG. 4.

Example 3. Isotope Tracing Analysis

K562 cells in RPMI media with GlutaMAX and 10% FBS were transferred to a 50 mL falcon tube and pelleted at 250×g for 5 min at 20° C. The cell media was removed, the cells were diluted with PBS at 1 million cells/mL, and 1 million cells (1 mL) was transferred to six 1.5 mL Eppendorf tubes. The cells were re-pelleted at 250×g for 5 min at ambient temperature, the supernatant was removed, and cells were re-suspended in 100 µL Milli-Q water or cell lysis buffer, each containing 500 ppm $^{13}C_5$ glutamine. Samples in which cells were resuspended in Milli-Q water were sonicated with a probe sonicator to lyse the cells.

For samples without cells, 100 µL Milli-Q water or cell lysis buffer was added to empty 1.5 ml tubes; these samples were processed using the same methods outlined below for the cell-containing samples. Samples incubated for 5 min at −20° C. or room temperature were centrifuged at 20,000×g for 5 min at 4° C. The supernatant (75 µl) from each sample was transferred to new 1.5 mL tubes.

For the samples with formic acid (221), the supernatant was transferred to 1.5 ml tubes containing 6.525 µl 15% $NH_4HCO_3$ to neutralize the acid. For the samples with formic acid (221) that were incubated for 60 min at room temperature, 8.7 µl 15% $NH_4HCO_3$ was added to the samples to neutralize the acid 18-20 min after lysis buffer addition. Samples incubated for 60 min at −20° C. or room temperature were centrifuged at 20,000×g for 5 min at 4° C. The supernatant (75 µl for samples without formic acid and 81.5 µl for samples with formic acid and 15% $NH_4HCO_3$) from each sample was transferred to new 1.5 mL tubes. All samples were dried in a SpeedVac and resuspended first with 10 µl acetonitrile, then 77.5 µl Milli-Q water and 12.5 µl 1.68M ammonium acetate were added. Samples were analyzed by LC/MS using reverse phase ion pairing and an Agilent 6520 QTOF. Results for technical replicates are shown in FIGS. 6A, 6B, 6C, 6D, and 6E. Results for biological replicates are shown in FIG. 7.

Figure 6A:
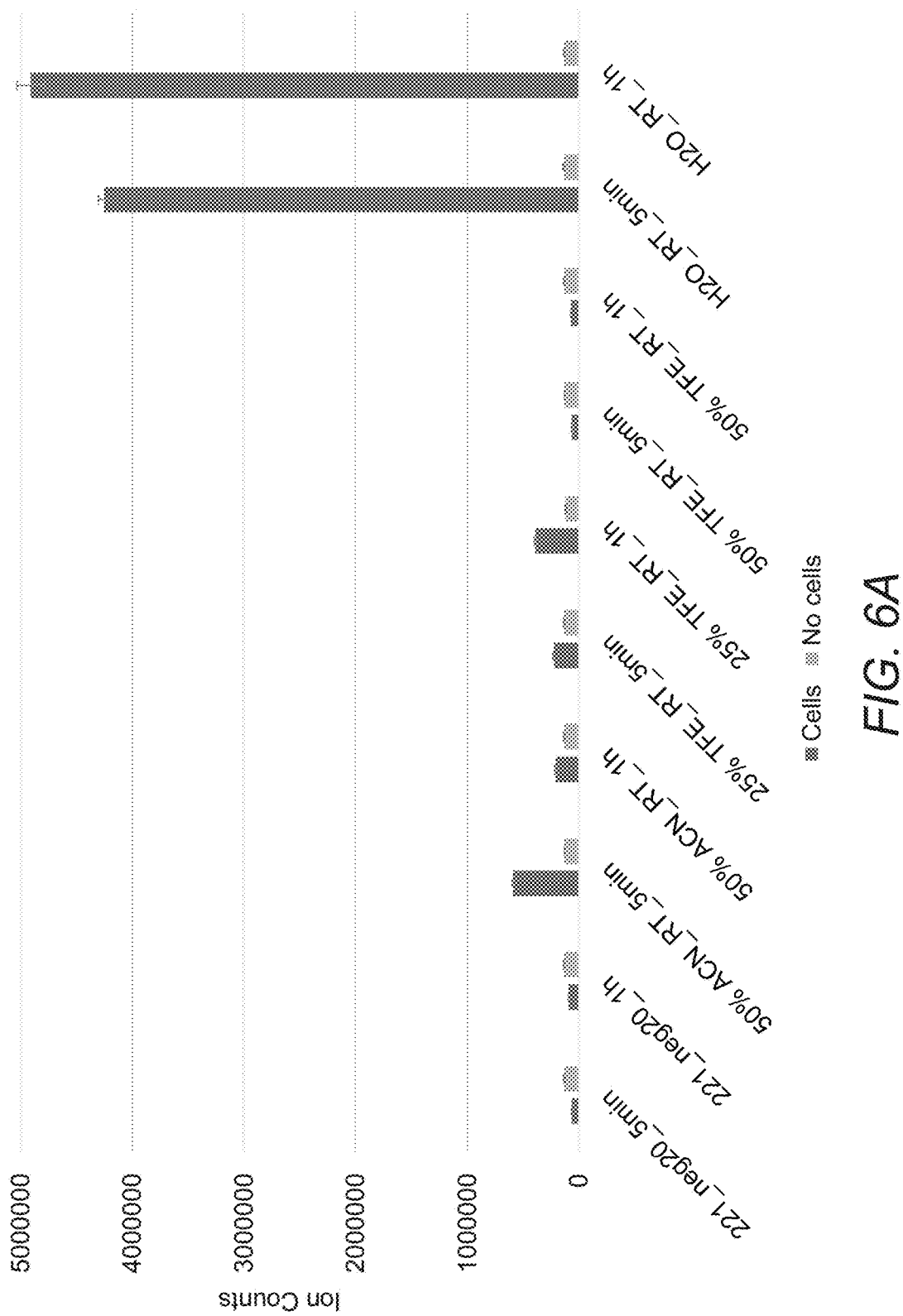
FIG. 6A depicts the ion abundances detected for $^{13}C_5$ glutamate (made from $^{13}C_5$ glutamine) in cell-containing and cell-free samples treated with either milliQ water (metabolism not quenched) or various lysis buffers at room temperature or −20° C.
Figure 6B:
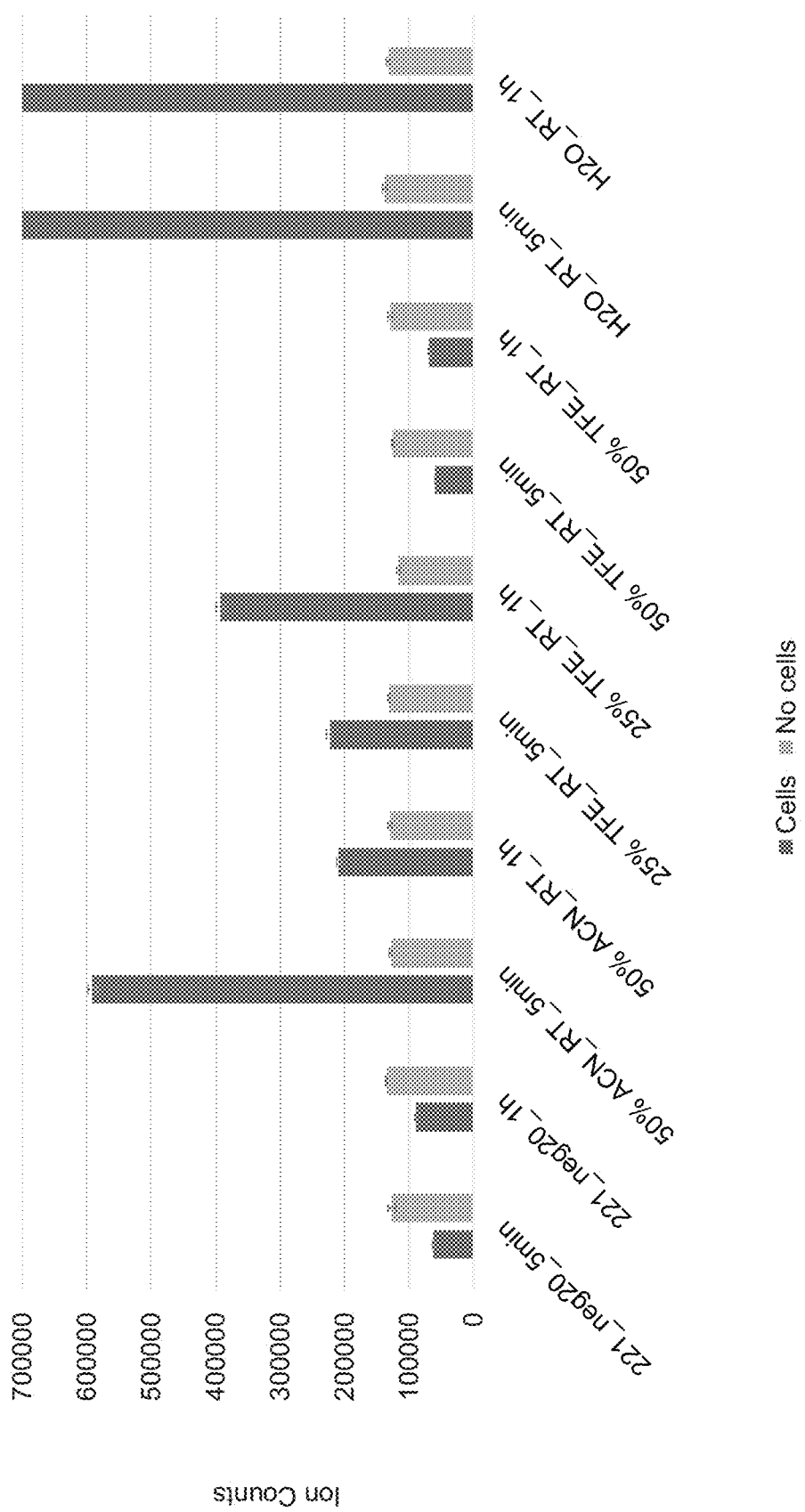
FIG. 6B is a zoomed view into the data of FIG. 6A to show the $^{13}C_5$ glutamate abundances for samples containing lysis buffers.
Figure 7:
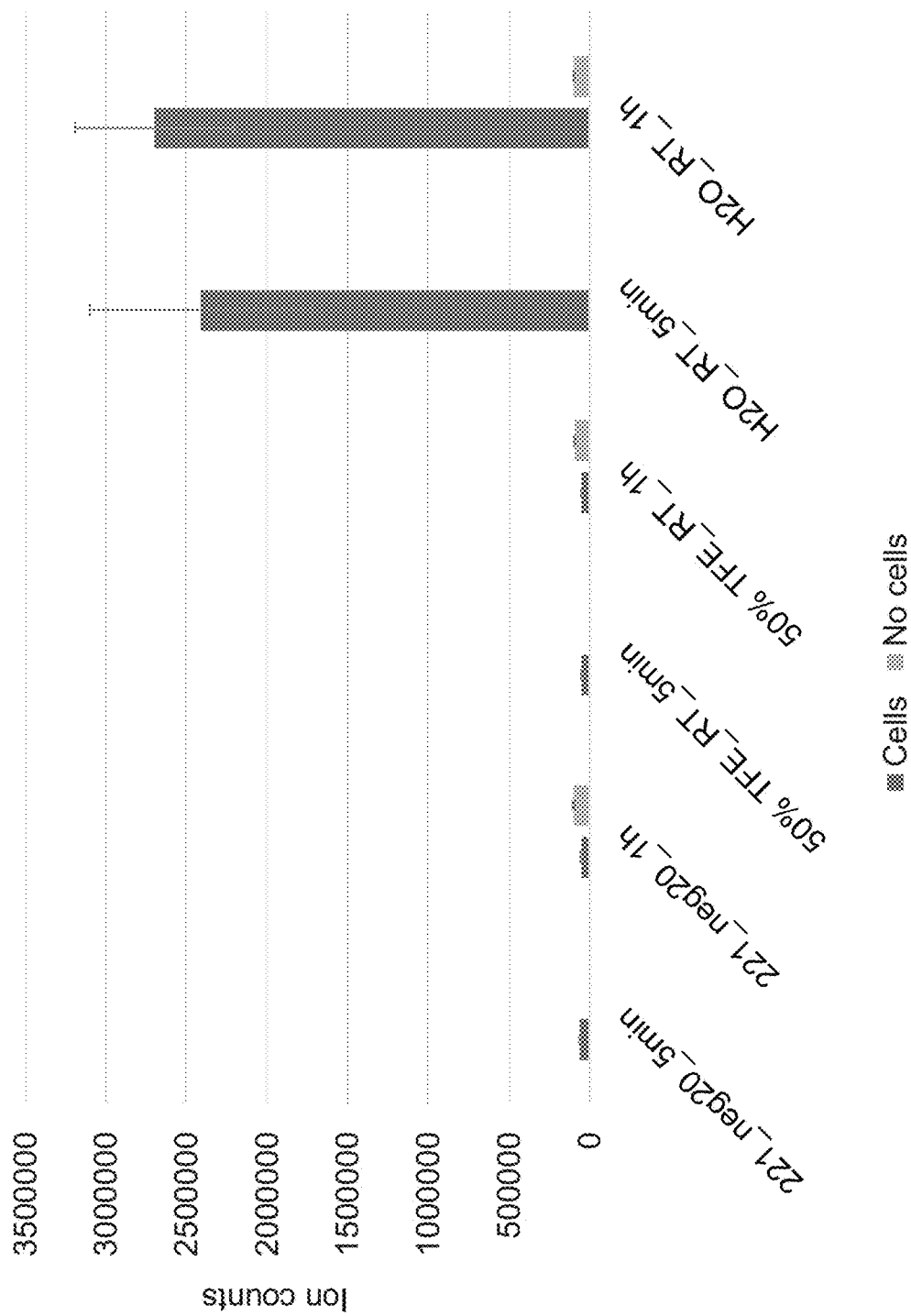
FIG. 7 depicts additional data for the ion abundances detected for $^{13}C_5$ glutamate (made from $^{13}C_5$ glutamine) in cell-containing and cell-free samples.

As shown in FIGS. 6A and 6B, a metabolic flux analysis confirms that room temperature 50% TFE quenches metabolism. FIG. 6A depicts the ion abundances detected for $^{13}C_5$ glutamate (made from $^{13}C_5$ glutamine) in cell-containing and cell-free samples treated with either Milli-Q water (metabolism not quenched) or various lysis buffers at room temperature or −20° C.

FIG. 6B shows the same data, zoomed in to show the $^{13}C_5$ glutamate abundances for samples containing lysis buffers. Room temperature 50% TFE and −20° C. 221 (2:2:1 MeOH:ACN:$H_2O$ with 0.1M FA) have $^{13}C_5$ glutamate abundances that are below the background $^{13}C_5$ glutamate abundances detected in the cell-free samples. All other lysis conditions have some detectable conversion of $^{13}C_5$ glutamine to $^{13}C_5$ glutamate, indicating metabolism is not quenched to the same extent in these samples. Of the conditions tested, room temperature 50% TFE provides the highest level of metabolism-quenching using this analysis method. In FIGS. 6A and 6B, sample name abbreviations are as follows: 221 (2:2:1 MeOH:ACN:$H_2O$ with 0.1M FA); neg20 (−20° C.); 50% ACN (solution of 50% acetonitrile in Milli-Q water); 50% TFE (solution of 50% 2,2,2-trifluoroethanol in Milli-Q water); 25% TFE (solution of 50% 2,2,2-trifluoroethanol in Milli-Q water); H2O (Milli-Q water); 5 min (5 minutes); 1 h (1 hour); RT (room temperature).

Figure 6C:
FIGS. 6C-6E depict an isotope tracing analysis of metabolites in the TCA cycle. Graphical illustrations of the level of $^{13}C_4$ Succinate (FIG. 6C), $^{13}C_4$ Malate (FIG. 6D), and $^{13}C_4$ Aspartate (FIG. 6E) detected in cell-containing and cell-free samples after treatment of cells with 500 ppm $^{13}C_5$ Glutamine in milliQ water or various cell lysis buffers.
Figure 6D:
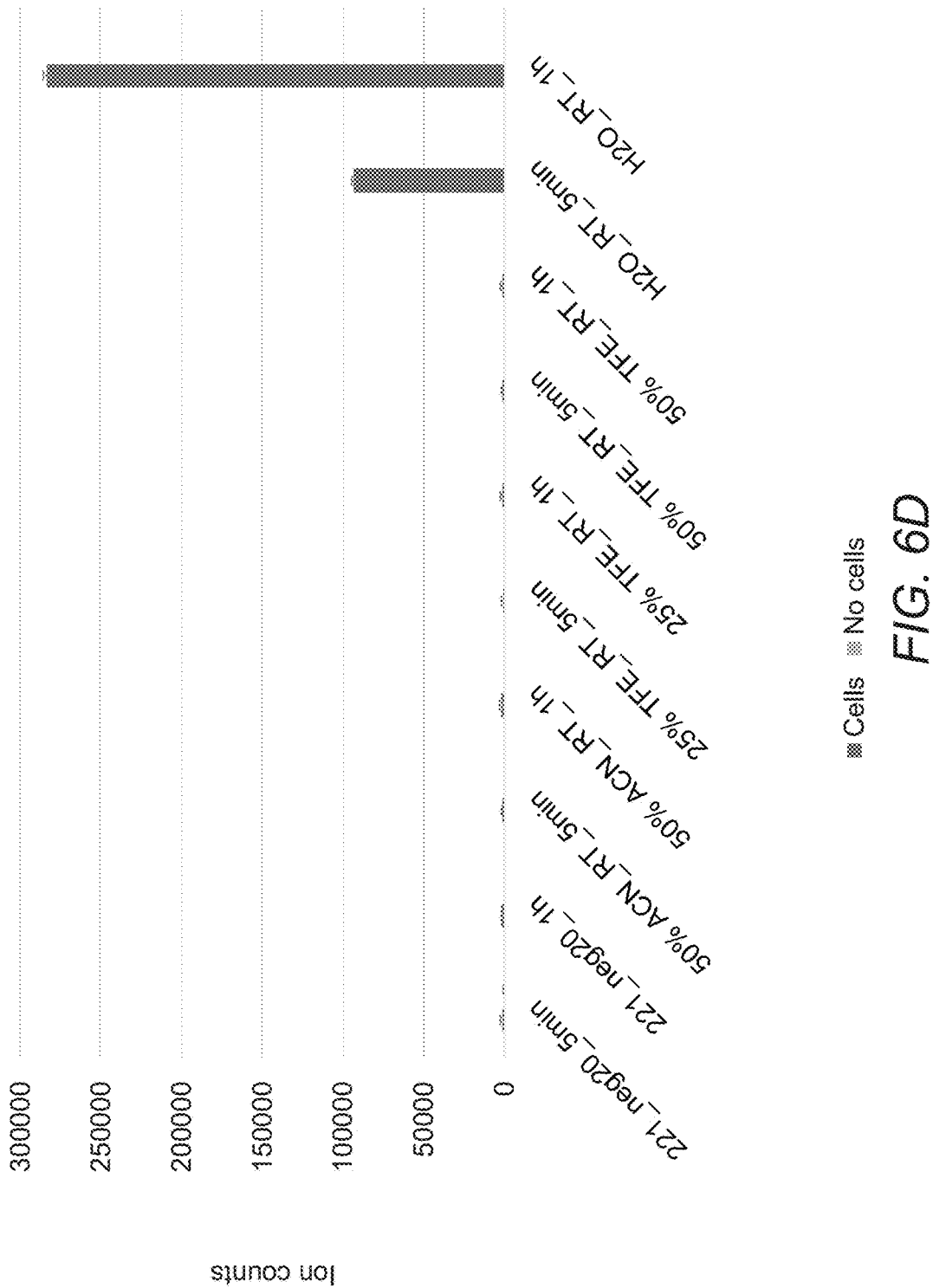
Figure 6E:
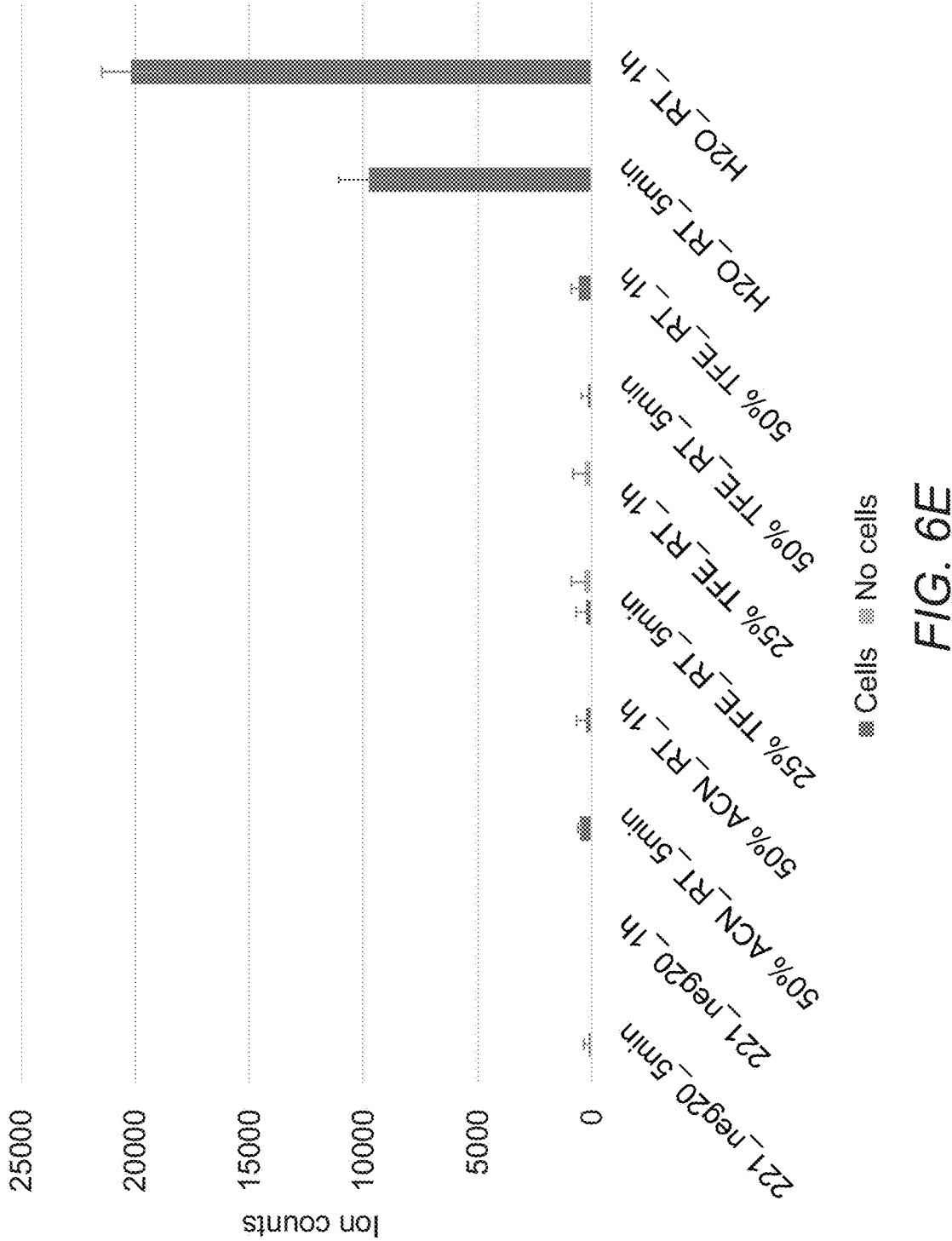

An isotope tracing analysis of metabolites in the TCA cycle was further conducted as described below. FIG. 6C reports the level of $^{13}C_4$ Succinate, FIG. 6D reports the level of $^{13}C_4$ Malate, and FIG. 6E reports the level of $^{13}C_4$ Aspartate as detected in cell-containing and cell-free samples after treatment of cells with 500 ppm $^{13}C_5$ Glutamine in Milli-Q water or various cell lysis buffers. Cells treated with water and lysed via sonication have detectable levels of $^{13}C_4$ Succinate, $^{13}C_4$ Malate, and $^{13}C_4$ Aspartate, which are fromed through metabolism of $^{13}C_5$ Glutamine. These detectable levles of $^{13}C_4$ Succinate, $^{13}C_4$ Malate, and $^{13}C_4$ Aspartate indicate metabolism has not been quenched in these samples. The $^{13}C_4$ Succinate, $^{13}C_4$ Malate, and $^{13}C_4$ Aspartate are not detected in any other samples. For samples that showed conversion of $^{13}C_5$ glutamine to $^{13}C_5$ glutamate in FIGS. 6A and 6B, the $^{13}C_4$ Succinate, $^{13}C_4$ Malate, and $^{13}C_4$ Aspartate may be undetctable because metabolism is partially quenched in these samples. In connection with FIGS. 6C-6E, sample name abbreviations are as follows: 221 (2:2:1 MeOH:ACN:$H_2O$ with 0.1M FA); neg20 (−20° C.); 50% ACN (solution of 50% acetonitrile in Milli-Q water); 50% TFE (solution of 50% 2,2,2-trifluoroethanol in Milli-Q water); 25% TFE (solution of 50% 2,2,2-trifluoroethanol in Milli-Q water); H2O (Milli-Q water); 5 min (5 minutes); 1 h (1 hour); RT (room temperature).

Referring to FIG. 7, biological replicate samples were made using the methods described for FIGS. 6A-6E. FIG. 7 shows ion abundances detected for $^{13}C_5$ glutamate in cell-containing and cell-free samples treated with Milli-Q water plus sonication (metabolism not quenched), room temperature 50% TFE, or −20° C. 221 (2:2:1 MeOH:ACN:H2O with 0.1M FA). $^{13}C_5$ Glutamate is formed from $^{13}C_5$ glutamine when enzymatic processes are not quenched (Milli-Q water samples). No $^{13}C_5$ glutamate is formed above background levels found in cell-free control samples for either room temperature 50% TFE or −20° C. 221. These results confirm the results from FIGS. 6A and 6B with biological replicates. In connection with FIG. 7, sample name abbreviations are as follows: 221 (2:2:1 MeOH:ACN:$H_2O$ with 0.1M FA); neg20 (−20° C.); 50% TFE (solution of 50% 2,2,2-trifluoroethanol in Milli-Q water); H2O (Milli-Q water); 5 min (5 minutes); 1 h (1 hour); RT (room temperature).

Example 4. Cell Lysate Precipitation of Cells Lysed and Quenched with a Fluoroalcohol Solution Comprising TFE This example compares solvent precipitation conditions for cell lysates made with room temperature 50% TFE in water. After K562 cells were lysed in 50% TFE, samples were diluted 2:1 or 4:1 with various precipitation solvents prior to centrifugation, removal of supernatants, drying of the precipitate pellet, and weighing of the dried pellets.

Precipitation conditions tested included 2:1 dilution with 100% EtOH or 1:1 EtOH:ACN, 2:1 dilution with 100% EtOH or 1:1 EtOH:ACN followed by addition of an equivalent amount of water (for a total 4:1 dilution), and 4:1 dilution with 2:1:1 water:EtOH:ACN or 1:1 water:EtOH.

Figure 8A:
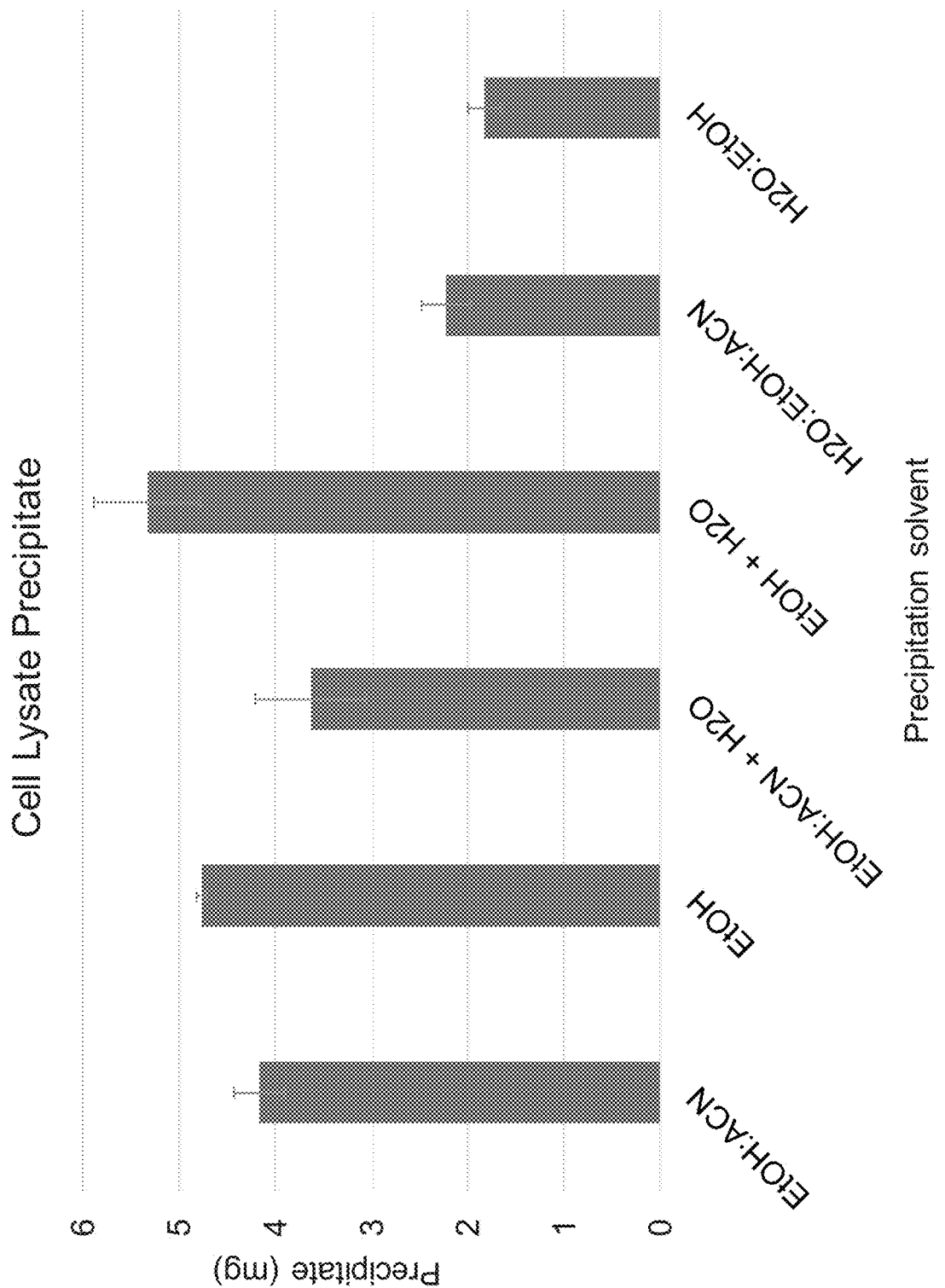
FIG. 8A reports precipitation with different solvents from cell lysates obtained by lysing and quenching cells with a solution comprising 50% TFE. For the EtOH:ACN+H$_2$O and EtOH+H$_2$O samples, the organic solvents were added to the samples prior to water addition. For the H$_2$O:EtOH:ACN and H$_2$O:EtOH samples, water was added with the organic solvents.

Referring to FIG. 8A, graphical representation of the dried pellet weight data is shown, indicating that the largest precipitate quantity is formed when the organic precipitation solvents (100% EtOH or 1:1 EtOH:ACN) are used in the absence of water. However, water can be added after initial precipitation by organic solvents without loss of precipitate. Thus, adding water to samples precipitated with organic solvent, wherein the final water content is approximately 50% v/v, does not cause loss of precipitate material. Water addition is necessary for improved metabolite recovery from EMR-lipid SPE column. Less precipitate is formed when water is added with the organic solvent. This difference is statistically significant.

Additional studies were conducted in order to compare a cell lysate precipitate volume obtained using different precipitation solvents. K562 cells (600,000 per sample) were isolated from their growth media using a 96-well plate with a glass fiber filter membrane. After media was removed via vacuum filtration, the cells were washed with PBS (200 µl per well) and lysed with 50% TFE (100 µl per well). After passing the cell lysate through the filter membrane and collecting it in a 96-well plate, an additional 25 µl 50% TFE was added to release any metabolites caught in the hold-up volume (~20 µl) of the filter plate. For the precipitation test, 2 wells of cell lysate were combined to make samples containing cell lysates from approximately 1.2 million cells EtOH:ACN (1:1) and EtOH:MeOH (1:1) precipitation solvents in various volumes (350, 385, 400, and 420 µl per combined sample) were added to the samples to compare amount of material precipitated. After adding the precipitation solvents, the samples were mixed with a vortex mixer, and they sat at room temperature for 10 min. Water was added in an equivalent volume as the precipitation solvent for each sample and the samples were mixed again using a vortex mixer. The samples were transferred to packed cell volume tube and centrifuged for 8 min (3+5 min, rotating tubes 180° in between) at 22° C., 2000×g. The volume of precipitate in each packed cell volume tube was measured using an adaptor designed for use with the packed cell volume tubes.

Figure 8B:
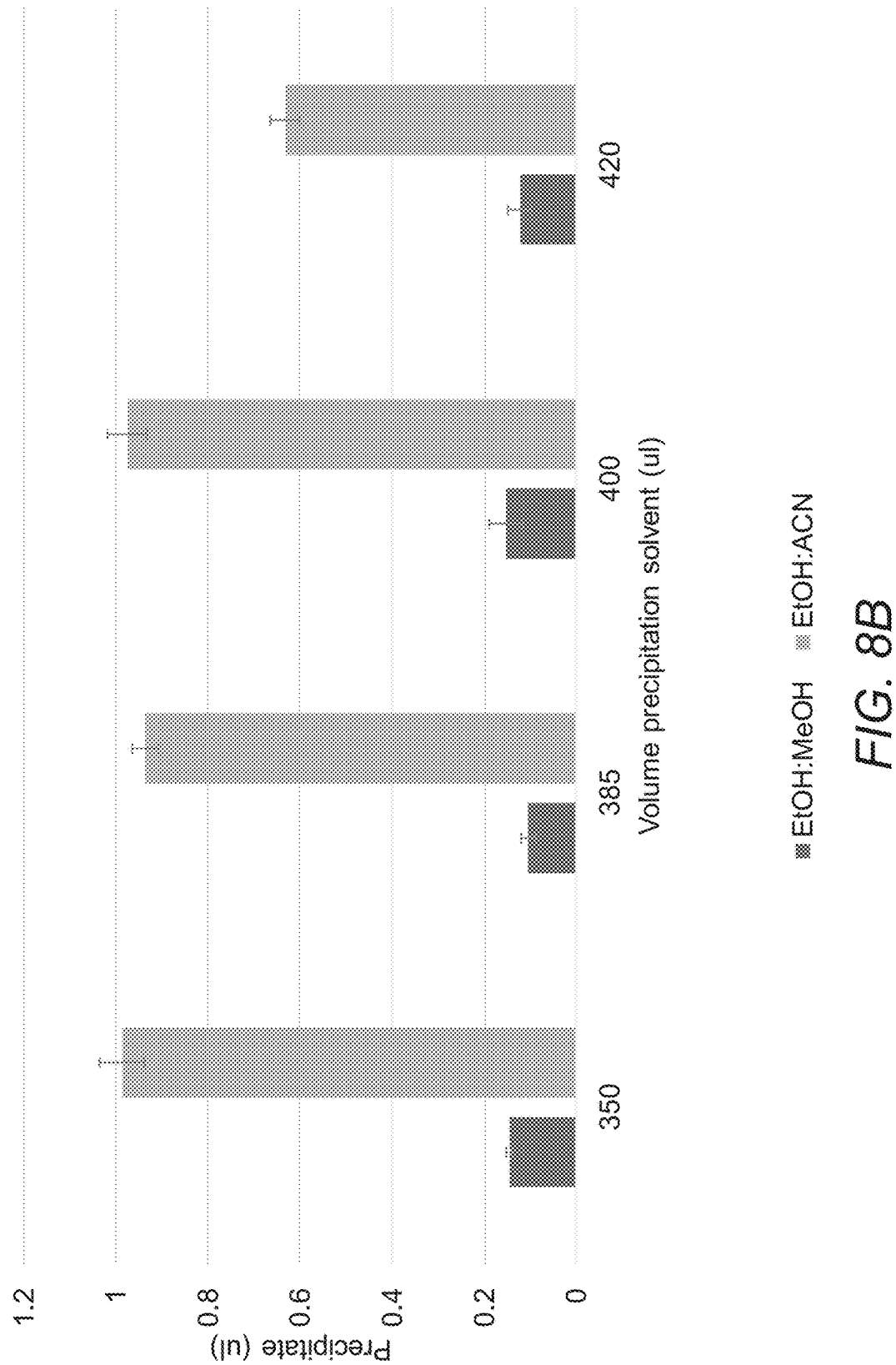
FIG. 8B reports additional precipitation data showing that precipitation with EtOH:MeOH produces a different amount of cell lysate precipitate in comparison to precipitation with EtOH:ACN.

Precipitation data from this analysis is reported in FIG. 8B which shows that EtOH:MeOH and EtOH:ACN make different amounts of cell lysate precipitates, which may impact the amount of protein and/or lipid recovered from the sample.

Example 5. Metabolite Recoveries for Metabolites Passed Through a CAPTIVA™ EMR-Lipid SPE Plate A standard mixture of metabolites was dissolved in 50% TFE (v/v) with each metabolite at 5 ppm and 100 μl aliquots were transferred to Eppendorf tubes. EtOH:ACN (1:1, 175 μl) or EtOH:MeOH (1:1, 175 μl) were added to each sample, the samples were mixed with a vortex mixer, and incubated at room temperature for about 15 minutes. After the incubation period, water (175 μl) was added to half of the samples to bring the water content to 50%. Samples were mixed again with a vortex mixer and then centrifuged at 20,000×g for 10 min (as a control) or they were added to the EMR-lipid plate and passed through the plate under positive pressure. Centrifuged samples had supernatants transferred to new Eppendorf test-tubes via pipet. 200 μl EMR-lipid elution buffer (2:1:1 water:ACN:EtOH, 1:1 ACN:EtOH, 2:1:1 water:MeOH:EtOH, or 1:1 MeOH:EtOH) was added to each sample.

This volume was added for consistency with the volumes used for the EMR-lipid plate samples (see below). EMR-lipid treated samples were pushed through the EMR-lipid plate using positive pressure. After samples eluted from the plate, 200 μl of wash buffer (2:1:1 water:ACN:EtOH, 1:1 ACN:EtOH, 2:1:1 water:MeOH:EtOH, or 1:1 MeOH:EtOH) was added to each well of the plate that had had a sample passed through it. The wash buffer was eluted from the plate using positive pressure and collected into the same collection plate as the samples. Samples were transferred to new Eppendorf tubes for drying and storage. Samples were dried using a nitrogen gas manifold, wherein the Eppendorf tubes were heated in a heat block warmed to 30° C. Samples were stored at −20° C. prior to being re-dissolved in 3:1 water: MeOH (MeOH added prior to water) and analyzed by LC/MS. Agilent MassHunter Quantitative analysis was used to extract and quantify known metabolite peaks from the LC/MS data. The metabolite peak areas for samples that passed through the CAPTIVA™ EMR-lipid plate were divided by the respective metabolite peak areas for the centrifuged control samples to determine the fraction of each metabolite that was recovered. The results of this analysis are shown in FIG. 9A.

FIG. 9B reports metabolite recoveries for cell lysates passed through a CAPTIVA™ EMR-lipid SPE plate. In this analysis, recovery of metabolites from mammalian cells lysed, quenched and extracted with 50% TFE was tested by adding 1:1 EtOH:ACN (200 μl) to a cell lysate comprising approximately 1 million mammalian cells lysed in 50% TFE (100 μl), mixing the sample to precipitate proteins, and adding Milli-Q water (200 μl) to the sample prior to passing the sample through an EMR-lipid material for lipid removal. To obtain the fraction recovered for each metabolite, a separate set of cell lysate samples was centrifuged at 20,000 g for 10 min to pellet the cell debris and the supernatants were collected. All samples were dried under nitrogen (g) at 30° C. and re-dissolved in 3:1 water:MeOH (MeOH added prior to water) with addition of an internal standard. Samples were analyzed by LC/MS and Agilent MassHunter Quantitative analysis was used to extract and quantify known metabolite peaks from the LC/MS data. The metabolite peak areas extracted for the EMR-lipid treated samples were divided by the respective metabolite peak areas for the centrifuged samples to calculate the fraction recovered for each metabolite.

Example 6. A Comparative Analysis of Lipids Removed by the EMR-Lipid SPE Matrix when Using Solutions Optimized for Non-Lipid Metabolite Recovery Lipid removal using the EMR-lipid SPE material remains high when using solvents optimized for metabolite recovery. Referring to FIG. 10, it reports extracted parent mass ions for several lipids that are commonly removed from plasma samples using the EMR-lipid SPE material.

Samples analyzed include cell lysates prepared using 50% TFE for cell lysis and metabolism-quenching, followed by addition of 200 μl 1:1 EtOH:ACN, followed by addition of 200 μl water. Samples at this stage were either passed through the EMR-lipid SPE material to remove lipids (Upper Panel in FIG. 10) or were centrifuged at 20,000×g to remove all protein precipitate (Lower Panel in FIG. 10).

A solution of 2:1:1 water:EtOH:ACN was used to either wash the EMR-lipid SPE material (EMR-lipid treated samples) or added to the supernatant of the centrifuged samples for consistency. All samples were dried and reconstituted first in 25 μl MeOH prior to addition of 75 μl water. Samples were analyzed by LC/MS using a reverse phase ion pairing chromatography separation and a 6520 QTOF. Parent ions for lipids of various lipid classes were extracted. PL, PG, SM, ether PC, and PE lipids were not found in the EMR-treated cell lysate but were present in the non-EMR-treated cell lysate, indicating that there was good removal of many lipid classes with the solvent conditions optimized for non-lipid metabolite recovery, see Example 5. The two fatty acid parent ions analyzed showed partial removal or no removal of these parent ions by the EMR-lipid material using the solvent conditions optimized for non-lipid metabolite recovery.

Example 7. Collecting DNA on the Glass Fiber Filter

Referring to FIGS. 11A-11D, samples were prepared by using a 1 μm glass fiber filter plate to remove media from 1 million K562 cells/well of a 96 well plate. For cases with lysed cells, a solution of 50% TFE was added to the filter plate and the resulting cell lysate was pulled through the filter plate to a collection plate after 10 minutes.

Figure 11A:
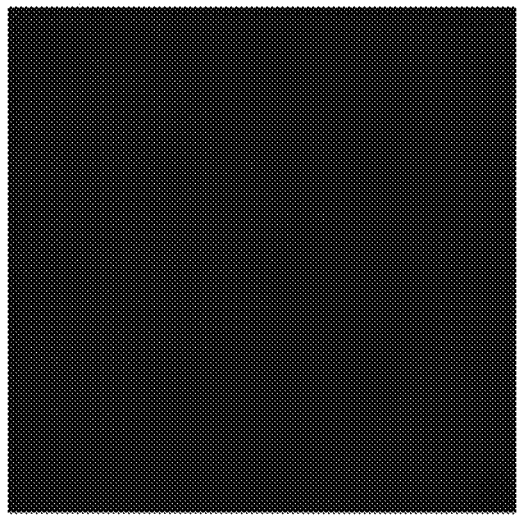
FIG. 11A depicts a filter with no cells (control)
Figure 11B:
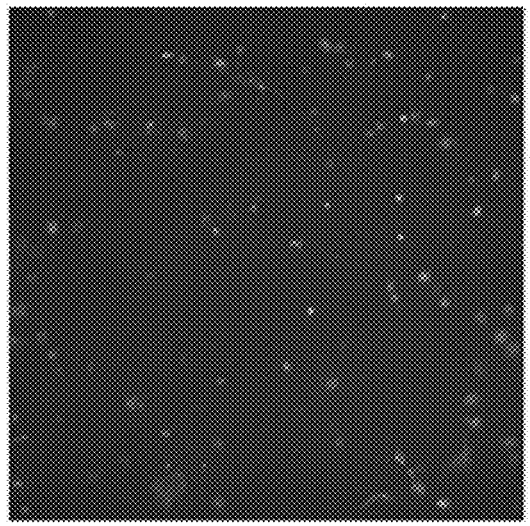
FIG. 11B depicts a filter with cells stained with DNA-binding fluorophore that have not been lysed.
Figure 11C:
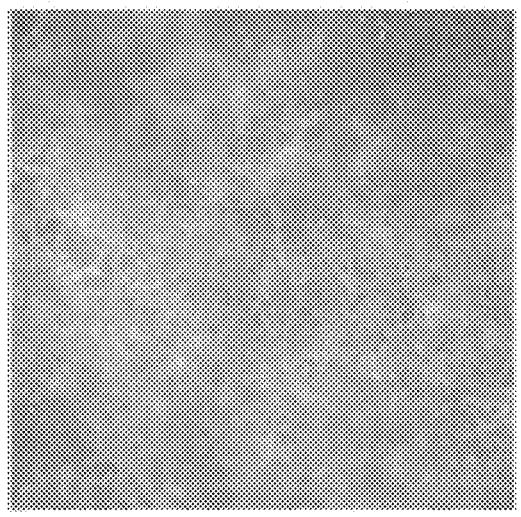
FIG. 11C depicts a filter after passage of cell lysate with DNA-binding fluorophore.
Figure 11D:
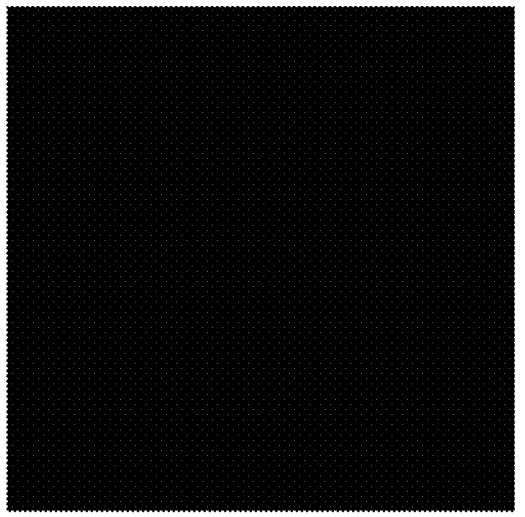
FIG. 11D depicts a filter after passage of unstained cell lysate.

The cell lysates were filtered through a glass fiber filter (borosilicate glass without binder, not coated). The filters were then stained with Ethidium Homodimer 1. As shown in FIGS. 11A-11D, DNA was captured on the glass fiber filter from the cell lysates. FIG. 11A is a control with no cells or TFE present. FIG. 11B shows intact, non-lysed cells; no TFE. FIG. 11C shows cells lysed with TFE with the cell lysate being pulled through the filter under vacuum and FIG. 11D shows a filter with unstained cells lysed with TFE with the cell lysate being pulled through the filter under vacuum.

Example 8. Analysis of Lipids Eluted from the EMR-Lipid SPE Matrix

To compare the CAPTIVA™ EMR-Lipid procedure for lipid extraction to conventional liquid-liquid extraction procedures, the following procedure was followed. For each sample preparation method evaluated, 100 μl of NIST Standard Reference Material (SRM) 1950 Metabolites in Frozen Human Plasma was used as a starting sample.

For the CAPTIVA™ EMR-Lipid procedure, starting with 100 μl of plasma, 900 μl of an Acetonitrile 1% Methanol solution was added to crash the proteins. This mixture was vortexed briefly and then ultrasonicated for 10 minutes. The entire mixture, including precipitate was transferred to a 1 ml EMR-Lipidomics Cartridge and flushed through under pressure. The cartridges were washed twice with 1 ml of a 90% Acetonitrile/Water solution. The cartridges were then eluted twice with 1 ml of 50% Chloroform/Methanol. The collected eluate was dried under a flow of Nitrogen and resuspended in 100 μl of 1:1 butanol:methanol. This sample was ready for LC/MS analysis or can be stored at −20° C. for subsequent analysis.

For the conventional published lipid extraction procedures, four separate procedures were evaluated. Three of these consisted of liquid-liquid extraction procedures: Folch (31), Bligh-Dyer (32), and Maytash (33). A fourth procedure BUME (34) was a single-phase extraction procedure.

The procedure for the liquid-liquid extraction procedures was identical in all cases except for the solvents as shown in table 1.

TABLE 1

Solvents for LLE

|  | Folch | Bligh-Dyer | Matyash |
|---|---|---|---|
| Org:MeOH:Water | 8:4:3 | 2:2:1.8 | 10:3:2.5 |
| Sample | 0.1 | 0.1 | 0.1 |
| Methanol (mL) | 0.5334 | 0.6896 | 0.387 |
| Organic Solvent (mL) | 1.066 | 0.6896 | 1.2904 |
| Water (mL)* | 0.4 | 0.6206 | 0.3226 |
| Organic: | Chloroform | Chloroform | MTBE |

Starting with 100 μl of plasma, ice-cold organic:methanol (2:1, v/v) in the amounts shown in Table 1 were added directly to the sample. The suspension was vortexed occasionally to bring about physical mixing and the sample was incubated on ice for 30 min. Water was added in the amount shown in Table 1 to separate the aqueous and organic layers. The suspension was incubated on ice for an additional 10 min. The samples were centrifuged at 2000 rpm for 5 min at 4° C. The lower organic layer was transferred to a new tube. The aqueous layer was re-extracted with 1 mL of 2:1, v/v organic/methanol. The organic layers were combined and dried with $N_2$ Drying at 30° C. and resuspended in 100 μl of 1:1 butanol:methanol. This sample was ready for LC/MS analysis or can be stored at −20° C. for subsequent analysis.

For the BUME Method, starting with 100 μl of plasma, 900 μl of 1:1 Butanol:Methanol 5 mM Ammonium Formate is added and vortexed. This mixture was sonicated for 60 minutes. The mixture was then centrifuged for 60 minutes at 16,000 G. The supernatant was transferred to a new vial and dried under a flow of Nitrogen and resuspended in 100 μl of 1:1 butanol:methanol. This sample was ready for LC/MS analysis or can be stored at −20° C. for subsequent analysis.

Figure 12:
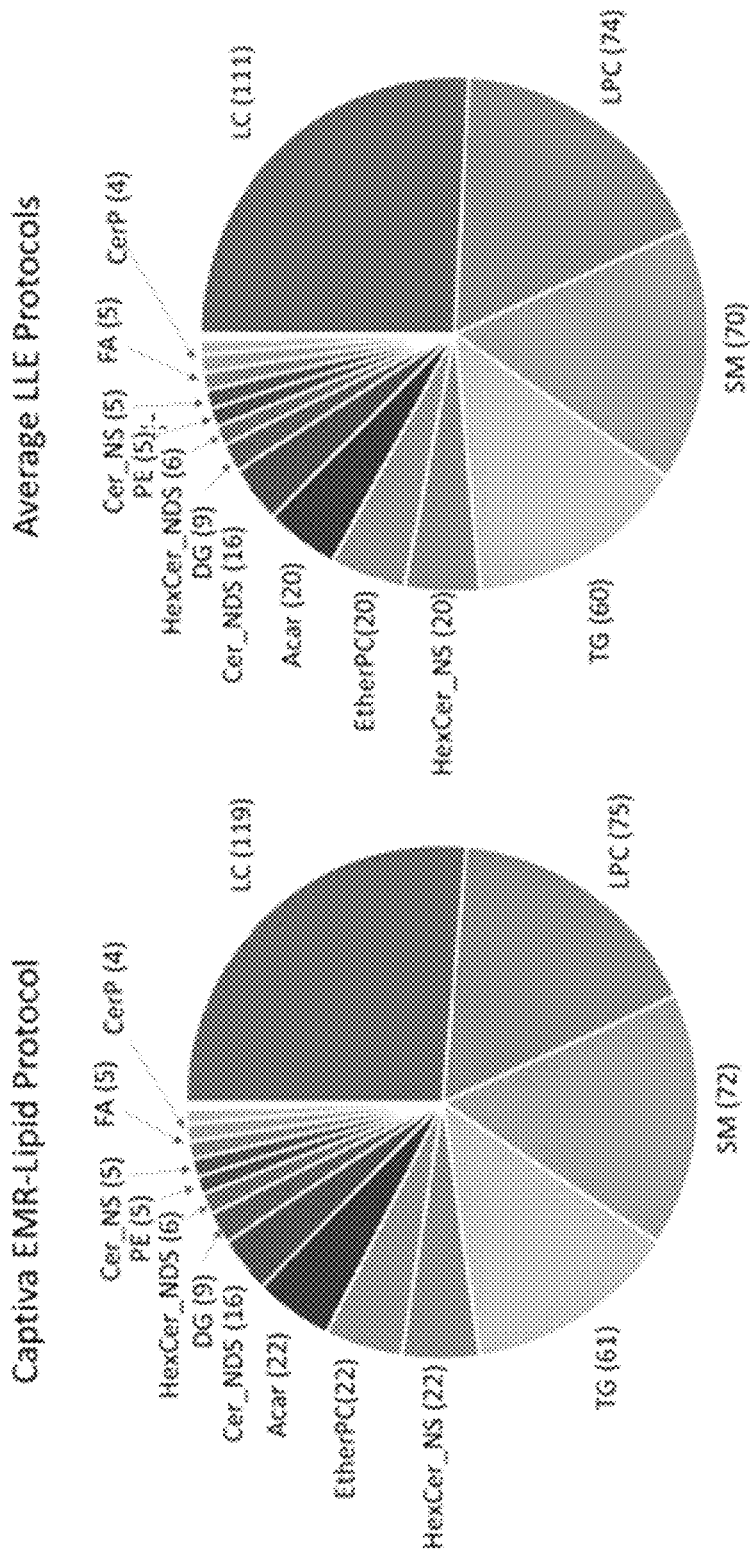
FIG. 12 reports an analysis of plasma lipids eluted from the EMR-lipid SPE matrix.

Each of resulting 5 samples was analyzed by LC-MS according to the method described in (35). The results in FIG. 12 show a summary comparing the CAPTIVA™ EMR-Lipid method with an average of the 4 conventional methods evaluated. The area of each pie slice represents the summed mass spectral peak area of the all of the detected lipids in the described lipid class. In FIG. 12, the abbreviation for the slices represent lipid classes as shown in Table 2. In FIG. 12, the number shown in parentheses is the total number of individual identified lipids in each class.

TABLE 2

Detected Lipid Classes

| Abbreviation | Lipid Group |
|---|---|
| ACar | AcylCarnitine |
| CE | Cholesteryl Ester |
| Cer_NDS | Ceramide non-hydroxyfatty acid-dihydrosphingosine |
| Cer_NS | Ceramide non-hydroxyfatty acid-sphingosine |
| CerP | Ceramide 1-phosphates |
| DG | Diacylglycerol |
| EtherPC | Ether-linked phosphatidylcholine |
| FA | Free fatty acid |
| HexCer_NS | Hexosylceramide non-hydroxyfatty acid-sphingosine |
| LPC | Lysophophatidylcholine |
| LPE | Lysophosphatidylethanolamine |
| PC | Phosphatidylcholine |
| PE | Phosphatidylethanolamine |
| SM | Sphingomyelin |
| TG | Triacylglycerol |

Example 9. Reverse Phase or HILIC Separation of Samples in a Solution Comprising TFE Experiments have demonstrated that samples dissolved in specific volumes and percentages of TFE can be introduced directly onto reversed phase or HILIC separations without degradation of resolution. FIG. 13A shows chromatograms of a metabolomics standard following injection of up to 40 μl of the metabolomics standard in 90% TFE without loss of resolution, except due to column overloading. FIG. 13B shows chromatograms of a reverse phase standard mixture following injection of up to 40 μl of the reverse phase standard mixture in 50% TFE without loss of resolution for smaller injection volumes.

Example 10. Metabolite and Lipid Workflow for Cells in Suspension

The following metabolite and lipid workflow was used for cells in suspension.
1) Lyse and quench cells with fluoroalcohol solution: Add 100 μl 1:1 TFE:water to a pellet of 1 million K562 cells in 1.5 ml Eppendorf tube. Vortex sample and flick bottom of Eppendorf tube with a finger to suspend cell pellet in the 50% TFE solution
2) Precipitate proteins (note: some proteins are precipitated in step 1): Add 200 μl 1:1 EtOH:MeOH, vortex and/or pipette solution up and down to mix, let sit for 5-15 min at room temperature.
3) Adjust solution composition: Add 200 μl water, vortex and/or pipette solution up and down to mix, let sit for 5-15 min at room temperature.
4) Remove lipids: Transfer samples to CAPTIVA™ EMR-lipid plate. Pass samples through plate using positive pressure or vacuum, achieving a drip rate of approximately 1 drop every 3-5 seconds. Increase positive pressure or vacuum pressure to empty the plate of as much liquid as possible.
5) Wash plate: Add 200 μl 2:1:1 Water:EtOH:MeOH (i.e. wash) to each used well of the CAPTIVA™ EMR-lipid plate. Pass wash buffer through CAPTIVA™ EMR-lipid plate using positive pressure or vacuum, achieving a drip rate of approximately 1 drop every 3-5 seconds.

Collect wash into same wells as original sample flow-through. Increase positive pressure or vacuum pressure to empty the plate of as much liquid as possible.
6) Dry polar metabolite samples: Dry samples in collection plate (i.e. polar metabolites) under nitrogen gas or under vacuum (i.e. SpeedVac). Gentle heating may be used to help dry the samples.
   i. Store dried polar metabolites at −20° C. or −80° C., until ready for analysis
7) Resolubilize the dried polar metabolite samples for analysis: resolubilize polar metabolite samples in 100 μl 3:1 $H_2O$:MeOH (add MeOH first, sonicate, then add water, sonicate and briefly/gently centrifuge (100×g, 20 s))
8) Release lipids from CAPTIVA™ EMR-lipid plate: Elute lipids from EMR plate with 1:2 dichloromethane: MeOH, collect samples in glass-coated 96 well plate
   i. Some possible volumes: 2×1 ml elutions, 2×900 μl elutions, 2×950 μl elutions, 4×1 ml elutions, 4×900 μl elutions, 4×950 μl elutions
   ii. Elute lipids with one portion of elution buffer at a time. Optionally evaporate or partially evaporate eluate between elutions.
   iii. Pass elution buffer through plate using positive pressure or vacuum, achieving a drip rate of approximately 1 drop every 3-5 seconds. After all portions of the elution buffer have been passed through the CAPTIVA™ EMR-lipid plate, increase positive pressure or vacuum pressure to empty the plate of as much liquid as possible.
9) Dry lipid samples: Dry lipid-containing samples under nitrogen gas or under vacuum (i.e. SpeedVac). Gentle heating may be used to help dry the samples.
10) Resolubilize lipid samples for analysis: resolubilize lipid samples in 100 μl of 1:1 BuOH:MeOH.

Example 11. Metabolite and Lipid Workflow for Adherent Cells

The following metabolite and lipid workflow was used for adherent cells.
1) Lyse and quench cells with fluoroalcohol solution: Add 1:1 TFE:water to a well or culture dish containing approximately 1 million adherent cells (culture media or wash buffer is already removed), using a volume that either covers the bottom of the well/culture dish or using a smaller volume and pipetting the volume repeatedly over the cells. Alternatively, add 800 μl 62.5% TFE to a well of a 6-well culture dish containing approximately 1 million adherent cells with approximately 200 μl wash buffer still present with the cells. Optional: scrape the bottom of the well/culture dish to pull up cells that remain attached.
2) Collect and dry cell lysate: transfer cell lysate from step 1 to an Eppendorf tube or similar. Dry cell lysate under nitrogen gas or under vacuum (i.e. SpeedVac). Gentle heating may be used to help dry the samples.
3) Resuspend cell lysate in fluoroalcohol solution: add 100 μl fluoroalcohol solution to dried cell lysate and mix to resuspend cell lysate.
4) Precipitate proteins (note: some proteins are precipitated in step 1): Add 200 μl 1:1 EtOH:MeOH, vortex and/or pipette solution up and down to mix, let sit for 5-15 min at room temperature
5) Adjust solution composition: Add 200 μl water, vortex and/or pipette solution up and down to mix, let sit for 5-15 min at room temperature
6) Remove lipids: Transfer samples to CAPTIVA™ EMR-lipid plate. Pass samples through plate using positive pressure or vacuum, achieving a drip rate of approximately 1 drop every 3-5 seconds. Increase positive pressure or vacuum pressure to empty the plate of as much liquid as possible.
7) Wash plate: Add 200 μl 2:1:1 Water:EtOH:MeOH (i.e. wash) to each used well of the CAPTIVA™ EMR-lipid plate. Pass wash buffer through CAPTIVA™ EMR-lipid plate using positive pressure or vacuum, achieving a drip rate of approximately 1 drop every 3-5 seconds. Collect wash into same wells as original sample flow-through. Increase positive pressure or vacuum pressure to empty the plate of as much liquid as possible.
8) Dry polar metabolite samples: Dry samples in collection plate (i.e. polar metabolites) under nitrogen gas or under vacuum (i.e. SpeedVac). Gentle heating may be used to help dry the samples.
   i. Store dried polar metabolites at −20° C. or −80° C., until ready for analysis
9) Resolubilize the dried polar metabolite samples for analysis: Resolubilize polar metabolite samples in 100 μl 3:1 $H_2O$:MeOH (add MeOH first, sonicate, then add water, sonicate and briefly/gently centrifuge (100×g, 20 s))
10) Release lipids from CAPTIVA™ EMR-lipid plate: Elute lipids from EMR plate with 1:2 dichloromethane: MeOH, collect samples in glass-coated 96 well plate
    i. Some possible volumes: 2×1 ml elutions, 2×900 μl elutions, 2×950 μl elutions, 4×1 ml elutions, 4×900 μl elutions, 4×950 μl elutions
    ii. Elute lipids with one portion of elution buffer at a time. Optionally evaporate or partially evaporate eluate between elutions.
    iii. Pass elution buffer through plate using positive pressure or vacuum, achieving a drip rate of approximately 1 drop every 3-5 seconds. After all portions of the elution buffer have been passed through the Captive EMR-lipid plate, increase positive pressure or vacuum pressure to empty the plate of as much liquid as possible.
11) Dry lipid samples: Dry lipid-containing samples under nitrogen gas or under vacuum (i.e. SpeedVac). Gentle heating may be used to help dry the samples.
12) Resolubilize lipid samples for analysis: Resolubilize lipid samples in 100 μl of 1:1 BuOH:MeOH Example 12. Metabolite Content Studies for Flow Through and Wash Eluates from CAPTIVA™ EMR-Lipid Plate In this analysis, cell pellets containing ~1 million K562 cells were lysed and metabolism was quenched by addition of 100 μl room temperature 50% TFE in water. Samples were vortexed and flicked to suspend the cell pellet and samples were incubated at room temperature (RT) for 5 min. 1:1 EtOH:MeOH (LCMS grade, 200 μl) was added to each sample, samples were mixed by pipet and incubated for 10-15 min at RT. Water (Milli-Q, 200 μl) was added to each sample, samples were mixed by pipet and incubated for 10-15 min at RT. Samples were passed through a CAPTIVA™ EMR-lipid plate under positive pressure and the eluate (flow-through) was collected, dried and re-dissolved in 100 μl 3:1 water:methanol. The CAPTIVA™ EMR-lipid plate was washed with 200 μl 2:1:1 water:MeOH:EtOH (Milli-Q and LCMS grade), flowing the volume through the plate under positive pressure. The eluate (wash) was collected, dried and re-dissolved in 100 μl 3:1 water:methanol. Samples were analyzed by LC/MS. For most analyzed metabolites, the wash contains a detectable level of the metabolite that would not be recovered without the wash of the CAPTIVA™ EMR-lipid plate.

Figure 14A:
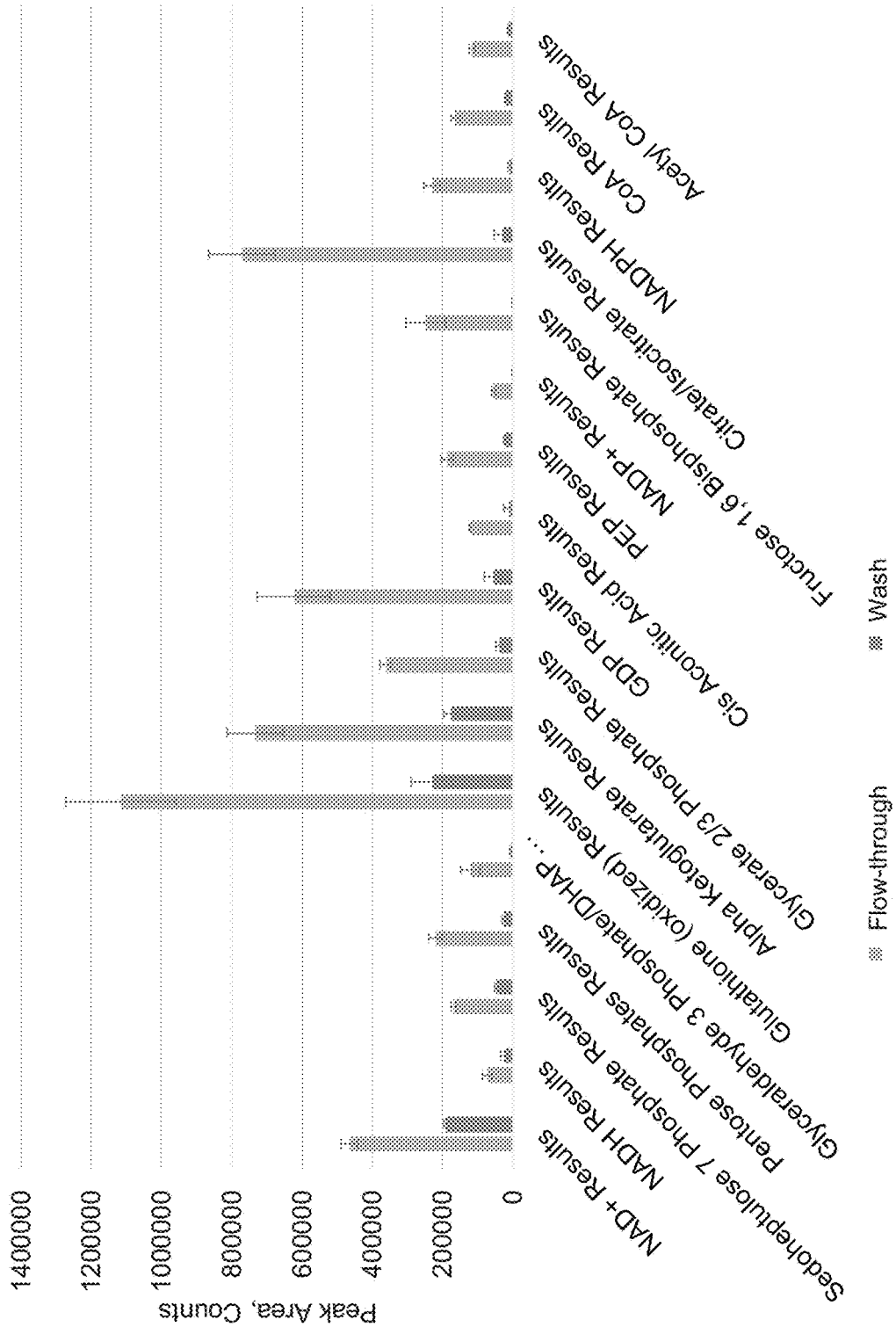
FIG. 14A reports metabolite ion abundances for lower abundance metabolites in flow through and wash eluates from CAPTIVA EMR-lipid plate.

FIG. 14A reports a metabolite content for lower abundance metabolites in flow through and wash eluates from CAPTIVA™ EMR-lipid plate.

Figure 14B:
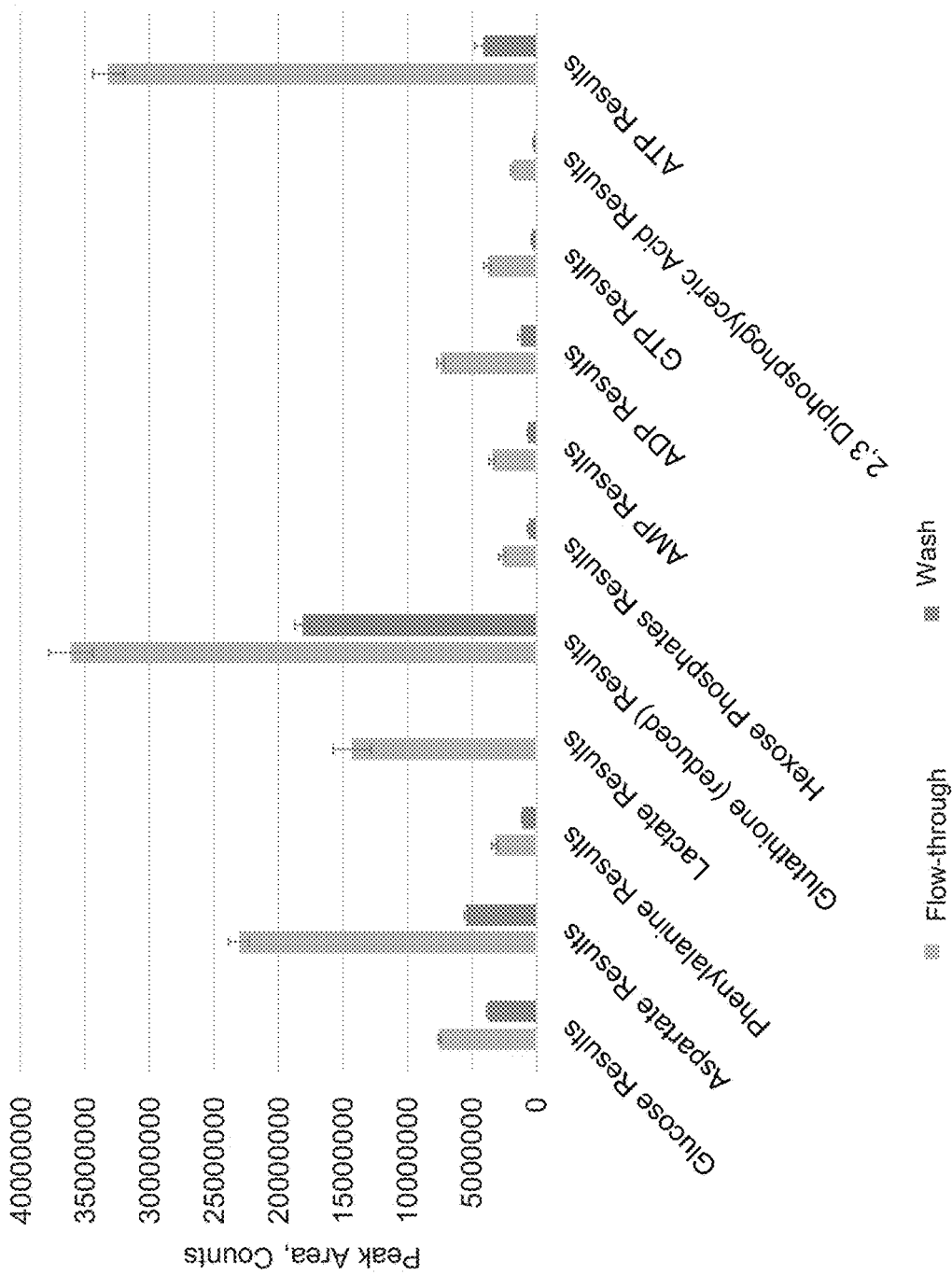
FIG. 14B reports metabolite ion abundances for higher abundance metabolites in flow through and wash eluates from CAPTIVA EMR-lipid plate.

FIG. 14B reports a metabolite content for higher abundance metabolites in flow through and wash eluates from CAPTIVA™ EMR-lipid plate.

Example 13. Peptide Analysis at Different Workflow Steps

Figure 15:
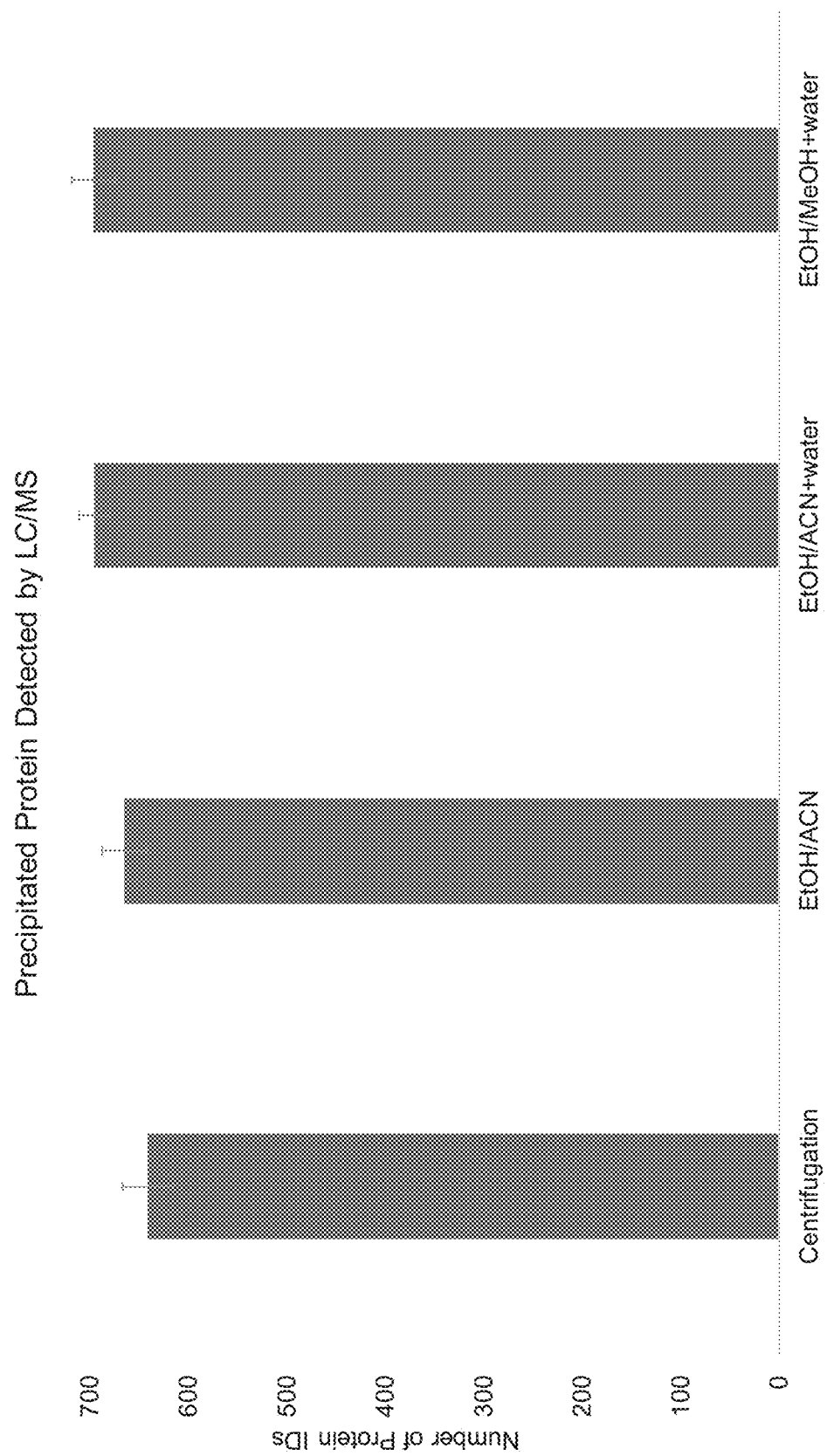
FIG. 15 reports a peptide analysis at different workflow steps.

In this analysis, peptides from protein precipitates collected after different steps in the workflow were analyzed by LC/MS. These results are reported in FIG. 15 which shows that protein precipitates collected after different steps in the workflow provide similar number of protein identifications. In FIG. 15, "Centrifugation" indicates proteins identified from pellet collected via centrifugation after addition of 50% TFE in water to K562 cells for cell lysis and metabolism quenching; "EtOH/ACN" indicates proteins identified from pellet collected via centrifugation after addition of EtOH/ACN to cell lysate made by adding 50% TFE in water to K562 cells; "EtOH/ACN+water" and "EtOH/MeOH+water" indicate proteins identified from a pellet collected via centrifugation after addition of EtOH/ACN or EtOH/MeOH, and then water, to cell lysate made by adding 50% TFE in water to K562 cells. As can be seen in FIG. 15, the number of total protein identifications are similar for protein precipitate collected at these different steps in the workflow.

Figure 16:
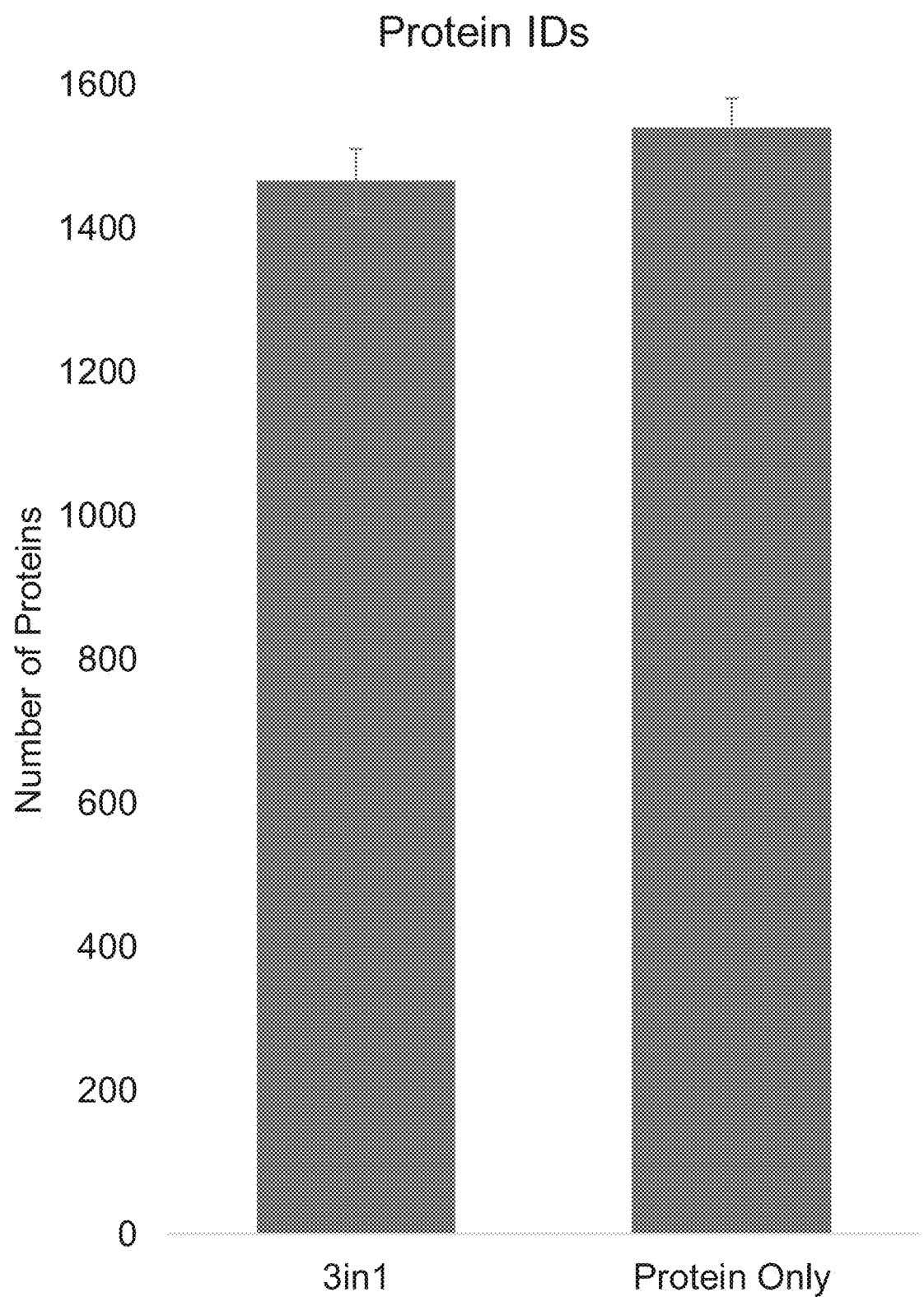
FIG. 16 reports protein identifications from 3 in 1 (protein, metabolite and lipid) workflow compared to traditional protein-only workflow.

Example 14. Protein Identifications from 3 in 1 (Protein, Metabolite and Lipid) Workflow Samples Compared to Traditional Protein-Only Workflow Samples For both workflows, the protein sample was prepared using the S-TRAP protein preparation method. For the 3 in 1 workflow, the protein precipitate used in the S-TRAP workflow was collected by centrifugation and removal of the supernatant after cell lysis and metabolism quenching with 50% TFE in water, and after protein precipitation with organic solvents and dilution of the resulting solution with water. The supernatant was carried on for metabolite and lipid collection. As shown in FIG. 16, the number of proteins identified from the 3 in 1 workflow is ~5% lower than the number of proteins identified from the protein only workflow.

Example 15. Lipid Identifications from 3 in 1 (Protein, Metabolite and Lipid) Workflow Samples as Compared to Traditional Lipid Extraction Workflow Samples For the 3 in 1 workflow, K562 cells were lysed and metabolism was quenched with 50% TFE in water. Subsequently, organic solvents were added for protein precipitation, water was added, the protein precipitate was recovered by centrifugation, and the supernatant comprising metabolites and lipids was passed through a CAPTIVA™ EMR-lipid plate, the eluate containing the polar metabolites. The CAPTIVA™ EMR-lipid plate was washed with a 50% water solution containing organic solvents, and the wash was combined with the eluate containing the polar metabolites. The lipids were eluted from the CAPTIVA™ EMR-lipid plate. The method used for comparison was a MTBE/Matyash method for the extraction of lipids. Overall, the 3 in 1 and MTBE methods provide lipid fractions with similar lipid signatures when analyzed by positive mode LC/MS, as is shown in the lipid hierarchical cluster map of FIG. 17. Lipids were identified using Agilent Lipid Annotator software and mapped using Mass Profiler Professional.

Figure 17:
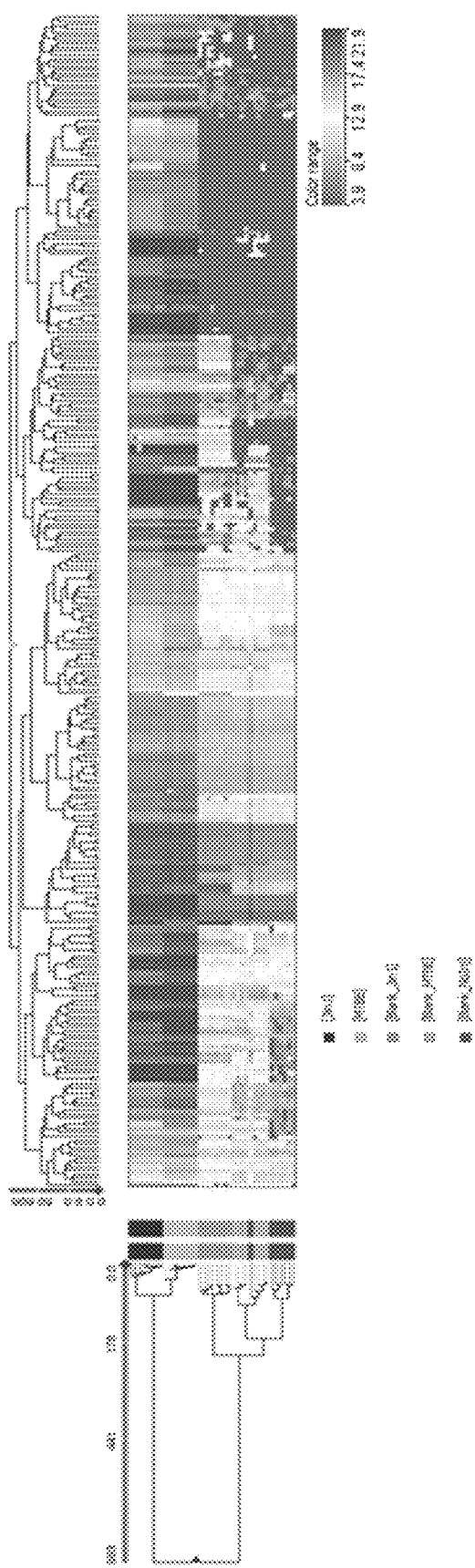
FIG. 17 reports lipid ion abundances for identified lipids from 3 in 1 (protein, metabolite and lipid) workflow compared to traditional lipid extraction workflow.
Figure 18A:
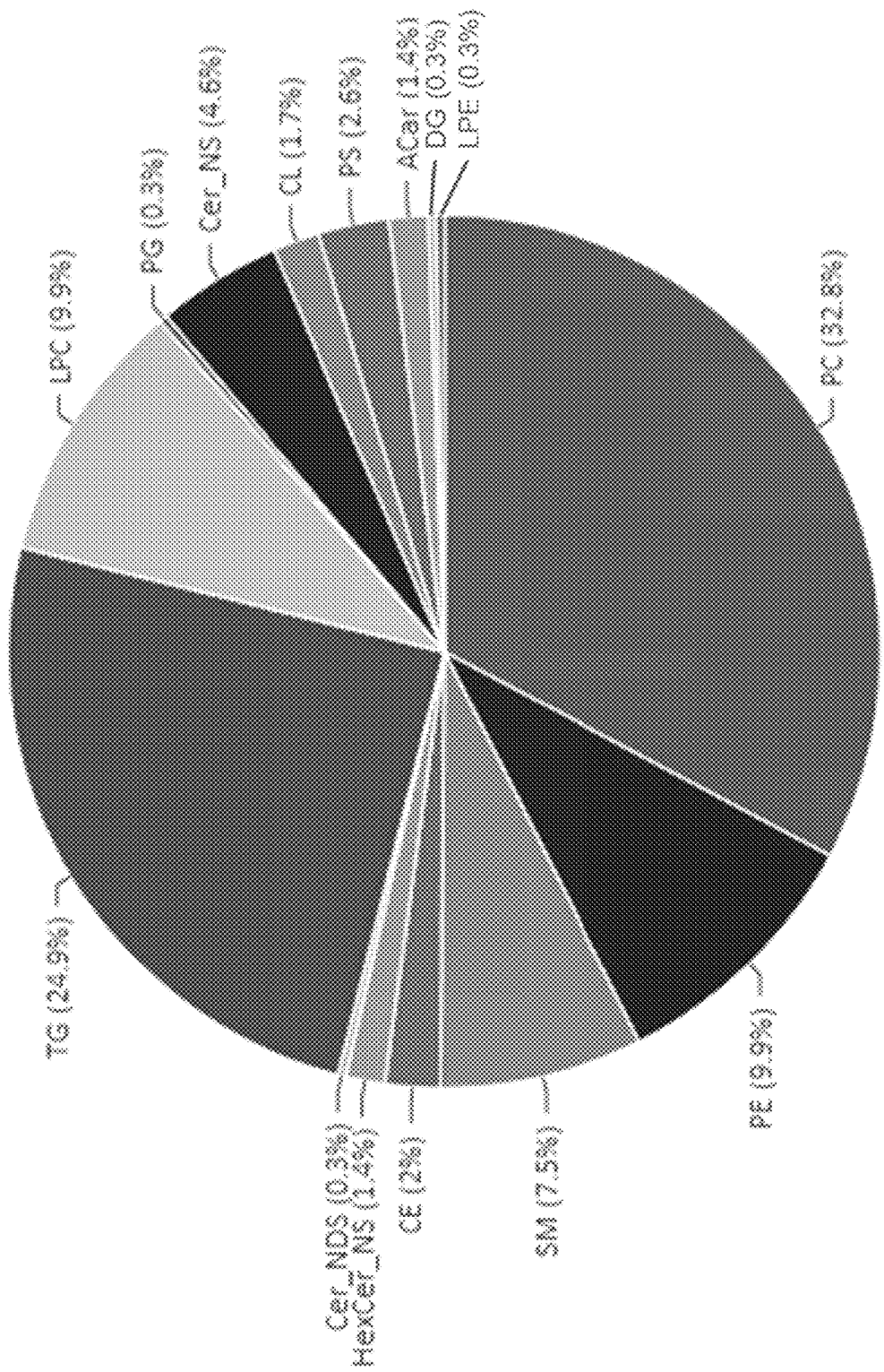
FIG. 18A depicts a pie-chart reporting relative representation of lipid classes in lipid samples from 3 in 1 (protein, metabolite and lipid) workflow.
Figure 18B:
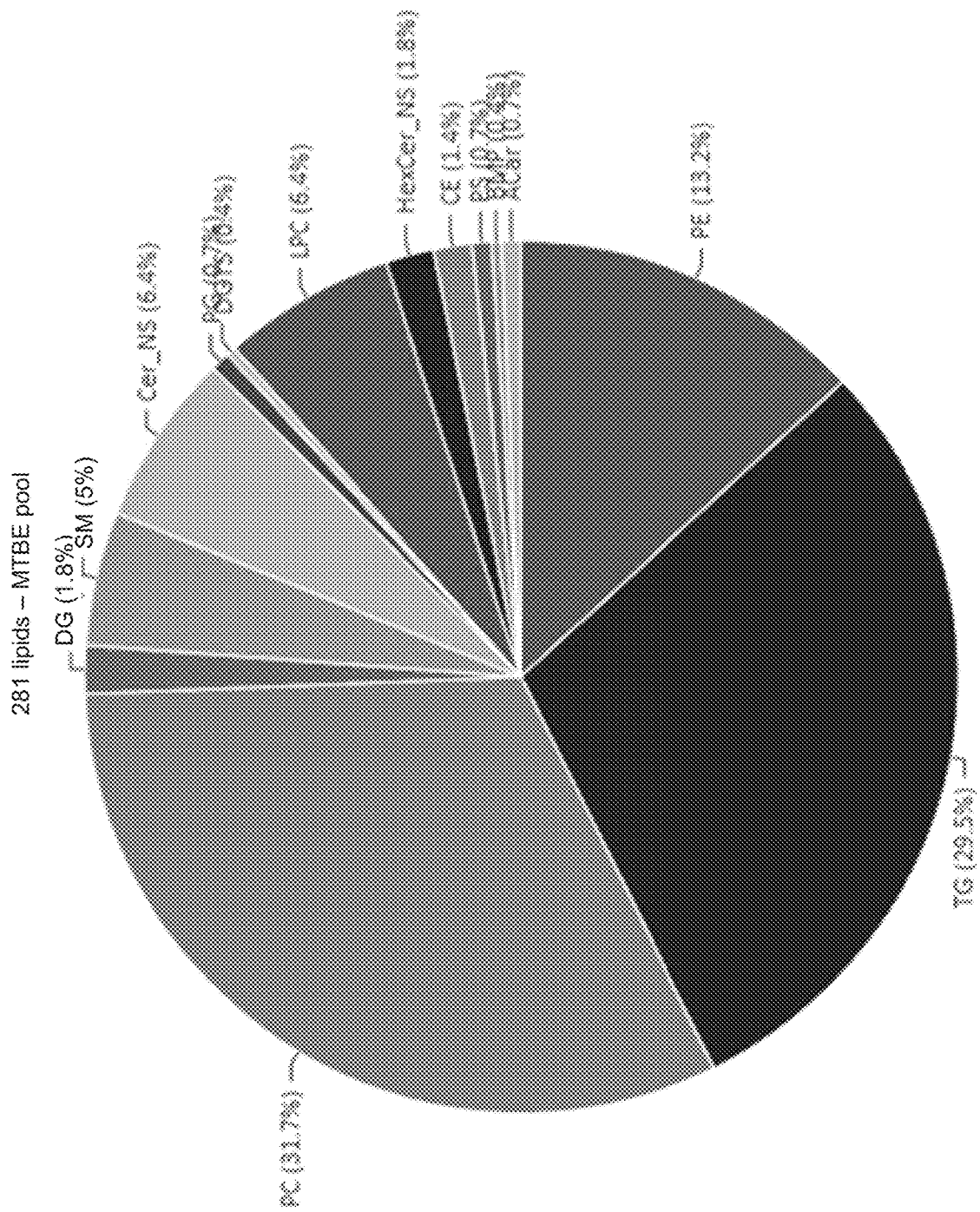
FIG. 18B depicts a pie-chart reporting relative representation of lipid classes in lipid samples from a traditional lipid extraction workflow.

The data shown in FIG. 17 is also shown in FIG. 18A, which depicts a pie-chart of lipid identifications from 3 in 1 (protein, metabolite and lipid) workflow and reports 345 lipid compounds identified in the 3in1 pool and FIG. 18B which depicts a pie-chart of lipid identifications from the traditional MTBE workflow and reports 281 lipid compounds identified in the MTBE pool. Abbreviations for detected lipid classes as listed in table 2.

Example 17. Metabolite Identifications from 3-in-1 (Protein, Metabolite and Lipid) Workflow Samples as Compared to Traditional Metabolite Extraction Workflow Samples For the 3-in-1 workflow, K562 cells were lysed and metabolism was quenched with 50% TFE in water. Subsequently, organic solvents were added for protein precipitation, water was added, the protein precipitate was recovered by centrifugation, and the supernatant comprising metabolites and lipids was passed through a CAPTIVA™ EMR-lipid plate, the eluate containing the polar metabolites. The CAPTIVA™ EMR-lipid plate was washed with a 50% water solution containing organic solvents, and the wash was combined with the eluate containing the polar metabolites, the polar metabolite fractions were dried and resuspended in 3:1 water:methanol. The traditional metabolite extraction method followed a workflow developed by Rabinowicz et al., referred to as the traditional 221 method (Lu et al. (2017). "Metabolite measurement: pitfalls to avoid and practices to follow." Annu Rev. Biochem. 86: 277-304).

Figure 19A:
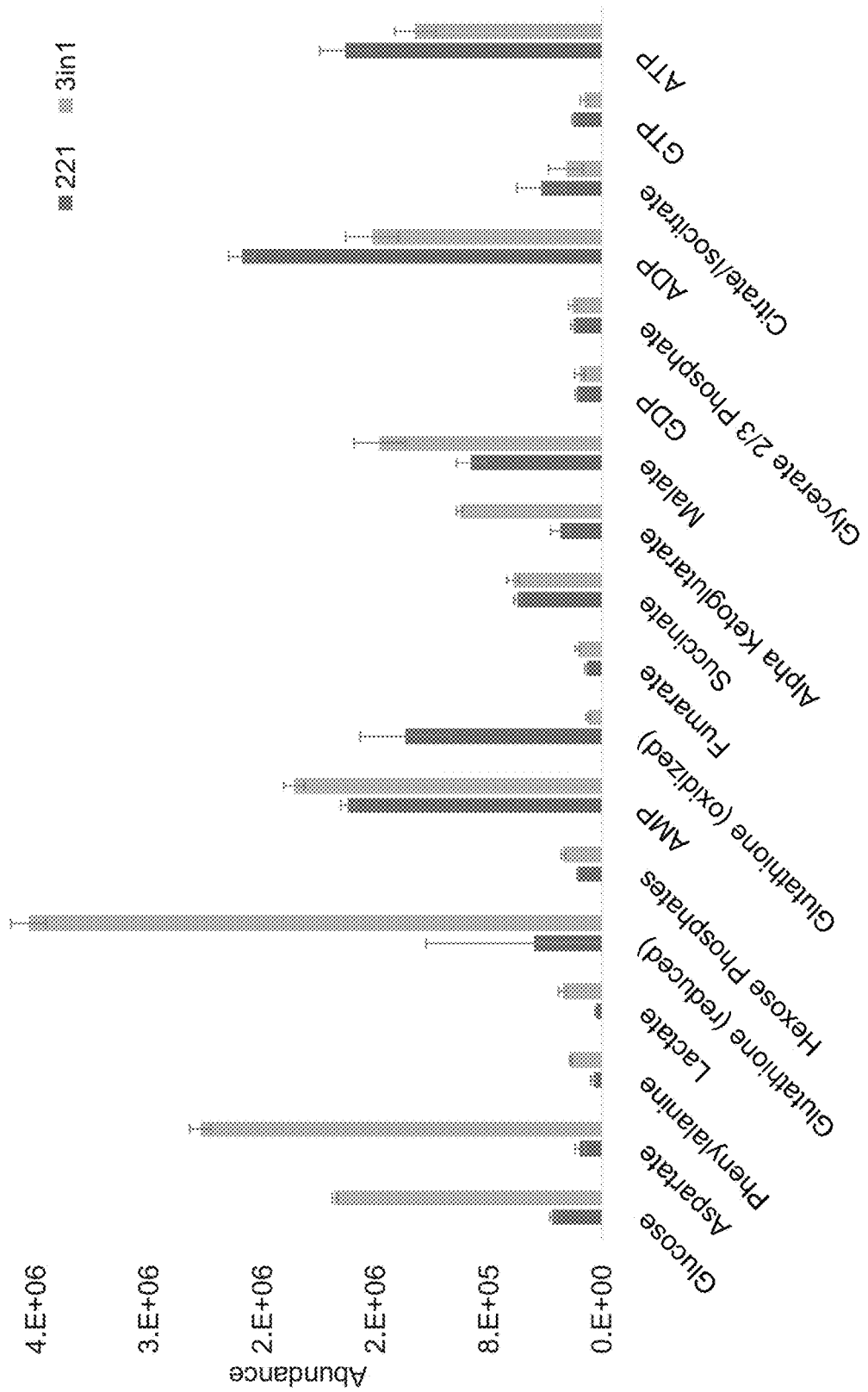
FIG. 19A reports metabolite ion abundances from a selected group of metabolites obtained by the 3 in 1 (protein, metabolite and lipid) workflow as compared to those obtained by the traditional 221 method.
Figure 19B:
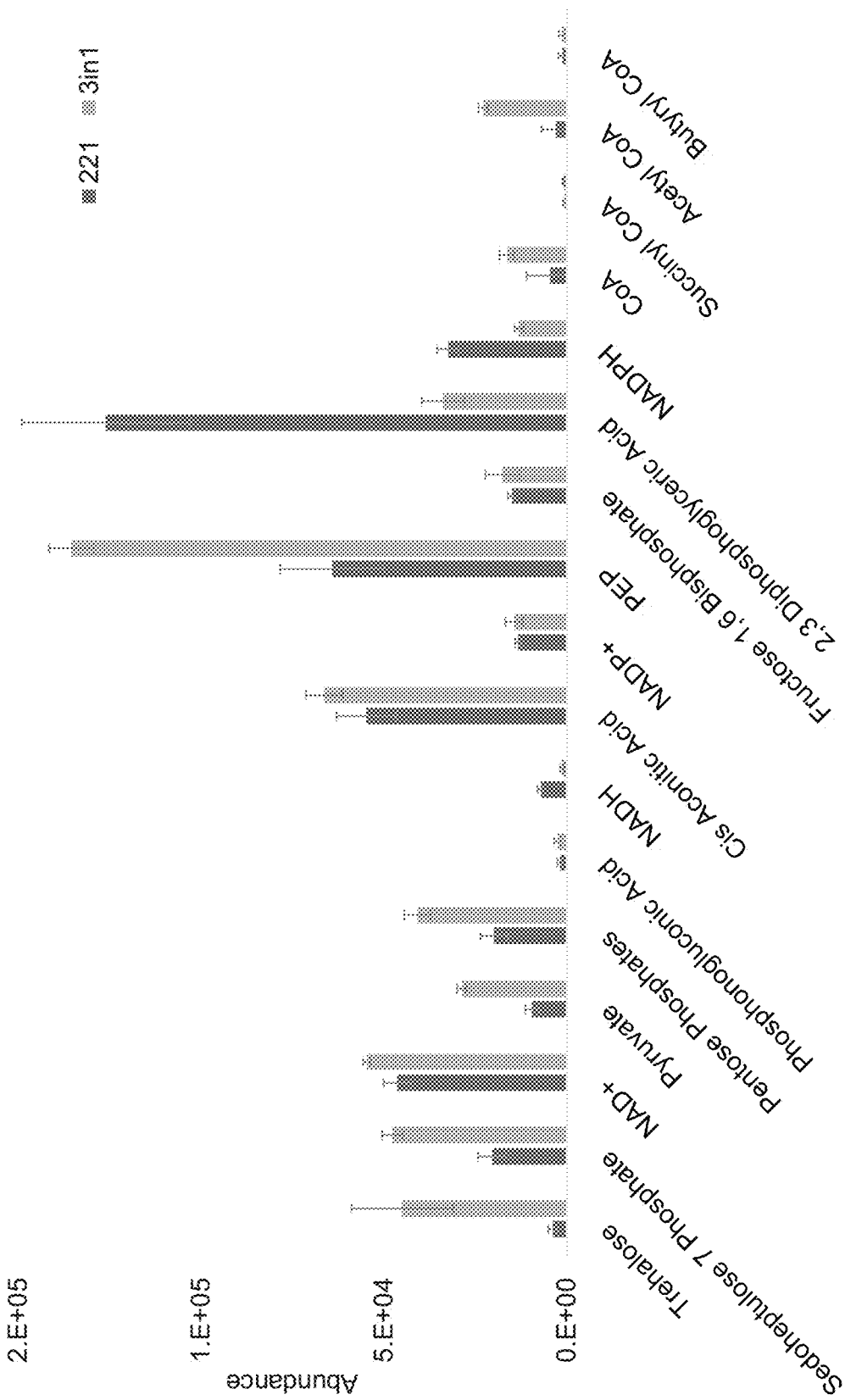
FIG. 19B reports additional metabolite ion abundances from a selected group of metabolites obtained by the 3 in 1 (protein, metabolite and lipid) workflow as compared to those obtained by the traditional 221 method.

FIG. 19A reports metabolite ion abundances from a selected group of metabolites produced by the 3 in 1 (protein, metabolite and lipid) workflow as compared to those produced by the traditional 221 method. FIG. 19B reports additional metabolite ion abundances from a selected group of metabolites produced by the 3 in 1 (protein, metabolite and lipid) workflow as compared to those produced by the traditional 221 method.

As can be seen in FIGS. 19A and 19B, some metabolites show differences in abundances between the two methods, but all metabolites measured in this targeted metabolite analysis were present in samples made using both workflows.

EXEMPLARY EMBODIMENTS

Non-limiting examples of embodiments of certain aspects of this disclosure are provided below.

Embodiment 1

A method for extracting metabolites from a biological sample, the method comprising:
  contacting at room temperature the biological sample with a metabolism-quenching solution comprising a fluoroalcohol,
  inhibiting one or more metabolic reactions in the biological sample with the fluoroalcohol;

extracting a mixture from the biological sample with the metabolism-quenching solution comprising the fluoroalcohol, the mixture comprising metabolites, lipids and proteins;
separating the metabolites from the mixture; and
collecting the metabolites.

Embodiment 2

The method of embodiment 1, wherein the biological sample comprises cells, and the cells are lysed by the fluoroalcohol.

Embodiment 3

The method of embodiment 1 or 2, wherein the mixture further comprises nucleic acids.

Embodiment 4

The method of any of the preceding embodiments, wherein the biological sample comprises one or more of the following: cells, a tissue sample, blood, plasma, serum, mucus, lymphatic fluid, synovial fluid, cerebrospinal fluid, saliva, bronchiolar lavage, gastric lavage, amniotic fluid, urine, vaginal fluid, semen or feces.

Embodiment 5

The method of any one of the preceding embodiments, wherein the room temperature is a temperature in the range from 10° C. to 30° C.

Embodiment 6

The method of any one of the preceding embodiments, wherein the room temperature is a temperature in the range from 19° C. to 23° C.

Embodiment 7

The method of any one of the preceding embodiments, wherein the extraction and separation are performed at room temperature.

Embodiment 8

The method of any one of the preceding embodiments, wherein the metabolism-quenching solution further comprises one or more of the following: water, a water-miscible solvent, a detergent, an acid, a base, a salt, or any combination thereof.

Embodiment 9

The method of any one of the preceding embodiments, wherein the metabolism-quenching solution comprises one or more of the following: acetonitrile, ethanol, methanol, isopropanol, acetic acid, formic acid, medronic acid, phosphate buffered saline, and/or ammonium bicarbonate.

Embodiment 10

The method of any one of the preceding embodiments, wherein the method further comprises one or more of the following: filtration, centrifugation, protein precipitation, size-exclusion and/or affinity chromatography, solvent evaporation, sample concentration (i.e. partial solvent evaporation or sample drying/solvent evaporation followed by sample reconstitution), sample drying, sample dilution, alteration of solvent composition, washing of a filter and/or column.

Embodiment 11

The method of any one of the preceding embodiments, wherein the method comprises filtering the mixture through a PVDF (polyvinylidene), nylon, PTFE (polytetrafluoroethylene), PC (polycarbonate), PP (polypropylene), PES (polyether sulfone), PVC (polyvinyl chloride), CA (cellulose acetate), CMF (coated cellulose acetate), HDPE (high density polyethylene), regenerated cellulose or glass fiber filter, or a stacked combination of filter types.

Embodiment 12

The method of any one of the preceding embodiments, wherein the method comprises contacting the mixture with an organic solvent and precipitating protein/peptide material from the mixture. Addition of 50% TFE (an organic-water solution) to cells precipitates a relatively large number of proteins. In some embodiments, the fluoroalcohol solutions can be the solution used for protein precipitation.

Embodiment 13

The method of any one of the preceding embodiments, wherein the fluoroalcohol is one or more of the following: 2,2,2-trifluoroethanol, 2,2-difluoroethanol, 2-fluoroethanol, hexafluoro-2-propanol, nonafluoro-tert-butyl alcohol, 1,1,2,2-pentafluoroethanol, and/or 2,2,3,3,3-pentafluoro-1-propanol.

Embodiment 14

The method of any one of the preceding embodiments, wherein the metabolism-quenching solution comprises 10-100% of the fluoroalcohol by volume.

Embodiment 15

The method of any one of the preceding embodiments, wherein the metabolism-quenching solution comprises from 45 v/v % to 55 v/v % of 2,2,2-trifluoroethanol.

Embodiment 16

The method of any one of the preceding embodiments, wherein separating the metabolites comprises one or more of the following:
(a) filtering the mixture comprising the metabolites and collecting the flow through comprising the metabolites, the proteins and the lipids;
(b) collecting the protein precipitate from the mixture directly or from the flow through of (a), or precipitating proteins from the mixture directly or from the flow through of (a), thereby obtaining a solution comprising the metabolites and the lipids;
(c) passing the solution of (b) through a solid-phase extraction matrix which binds the lipids; and
(d) collecting the metabolites in a flow through solution.

Embodiment 17

The method of embodiment 16, wherein the method further comprises collecting protein precipitates, optionally, further preparing the collected proteins for analysis for example by peptide digestion workflows, and/or eluting and collecting lipids.

Embodiment 18

A method for extracting metabolites and one or more of proteins, lipids or nucleic acids from a biological sample, the method comprising one or more of the following:
(a) contacting at room temperature the biological sample with a metabolism-quenching solution which comprises a fluoroalcohol and thereby obtaining a mixture comprising metabolites, proteins, lipids and nucleic acids;
(b) filtering the mixture of (a) through a filter and collecting the flow through comprising the metabolites, the proteins and the lipids;
(c) precipitating proteins from the flow through of (b), if they are not already precipitated to the desired level, and thereby obtaining a solution comprising the metabolites and the lipids;
(d) collecting the protein precipitates;
(e) passing the solution comprising the metabolites and the lipids from (c) through a solid-phase extraction matrix which binds lipids;
(f) collecting the metabolites in a flow through solution; and
(g) eluting the lipids from the solid-phase extraction matrix.

Embodiment 19

The method of embodiment 18, wherein (b) comprises filtering the mixture through a glass fiber filter and eluting the nucleic acids from the filter.

Embodiment 20

The method of any one of embodiments 18-19, wherein the proteins are precipitated with an organic solvent, optionally diluting the protein/organic solvent mixture with water, and collecting the precipitate on a filter or by centrifugation. The proteins and nucleic acids can be also collected on the same filter, e.g. protein precipitate on top and nucleic acids bound to the filter. For collecting proteins, various filters can be used, including, but not limited to, a PVDF (polyvinylidene), nylon, PTFE (polytetrafluoroethylene), PC (polycarbonate), PP (polypropylene), PES (polyether sulfone), PVC (polyvinyl chloride), CA (cellulose acetate), CMF (coated cellulose acetate), HDPE (high density polyethylene), regenerated cellulose or glass fiber filter or a stacked combination of filter types.

Embodiment 21

The method of embodiment 20, wherein the protein precipitate is prepared for analysis using typical protein sample preparation methods, such as FASP, PASP, and S-TRAP.

Embodiment 22

The method of embodiment 20, wherein the protein precipitate is re-dissolved in solutions containing trifluoroethanol or heptafluoroisopropanol.

Embodiment 23

The method of any one of embodiments 18-22, wherein prior to loading onto the solid-phase extraction matrix, the solution comprising the metabolites and the lipids is diluted with water and/or a water-miscible solvent, wherein the water-miscible solvent comprises one or more of the following: acetonitrile, ethanol, methanol, isopropanol, formic acid, acetic acid and any mixtures thereof.

Embodiment 24

The method of any one of embodiments 18-23, wherein the solid phase extraction material is washed with a water-containing solvent mixture to increase metabolite elution from the solid phase extraction material. In this embodiment of the method, the EMR-lipid material is washed to increase the recovery of metabolites before the lipids are eluted from the EMR-lipid material. The preferred wash solutions include 2:1:1 water:ethanol:ACN and 2:1:1 water:ethanol:methanol.

Embodiment 25

The method of any one of embodiments 18-24, wherein the lipids are eluted from the solid-phase extraction matrix with non-polar, non-aqueous solvents or mixtures comprising one or more of MTBE, butanol, methanol, ethanol, dichloromethane, chloroform, or isopropanol.

Embodiment 26

The method of any one of embodiments 18-25, wherein the biological sample comprises one or more of the following: cells, a tissue sample, blood, plasma, serum, mucus, lymphatic fluid, synovial fluid, cerebrospinal fluid, saliva, bronchiolar lavage, gastric lavage, amniotic fluid, urine, vaginal fluid, semen or feces.

Embodiment 27

The method of any one of embodiments 18-26, wherein (b) comprises filtering the mixture through a PVDF (polyvinylidene), nylon, PTFE (polytetrafluoroethylene), PC (polycarbonate), PP (polypropylene), PES (polyether sulfone), PVC (polyvinyl chloride), CA (cellulose acetate), CMF (coated cellulose acetate), HDPE (high density polyethylene), regenerated cellulose or glass fiber filter or a stacked combination of filter types.

Embodiment 28

The method of any one of embodiments 18-27, wherein the metabolism-quenching solution comprises 10 v/v % to 100 v/v % of fluoroalcohol, and the fluoroalcohol is one or more of the following: 2,2,2-trifluoroethanol, 2,2-difluoroethanol, 2-fluoroethanol, hexafluoro-2-propanol, nonafluoro-tert-butyl alcohol, 1,1,2,2,2-pentafluoroethanol, or 2,2,3,3,3-pentafluoro-1-propanol.

Embodiment 29

The method of any one of embodiments 18-28, wherein the metabolism-quenching solution comprises from 45 v/v % to 55 v/v % of 2,2,2-trifluoroethanol.

Embodiment 30

The method of any one of embodiments 18-29, wherein the room temperature is a temperature in the range from 10° C. to 30° C.

Embodiment 31

The method of any one of embodiments 18-30, wherein the room temperature is a temperature in the range from 19° C. to 23° C.

Embodiment 32

The method of any one of embodiments 18-31, wherein all method steps are performed at room temperature.

Embodiment 33

The method of any one of embodiments 18-32, wherein the metabolism-quenching solution further comprises one or more of the following: water, a water-miscible solvent, a detergent, an acid, a base, a salt, or any combination thereof.

Embodiment 34

The method of any one of embodiments 18-33, wherein the metabolism-quenching solution further comprises one or more of the following: acetonitrile, ethanol, methanol, isopropanol, acetic acid, formic acid, medronic acid, phosphate buffered saline, and/or ammonium bicarbonate.

Embodiment 35

A method for extracting metabolites and lipids from a biological sample comprising cells, the method comprising:
- (a) lysing and quenching the cells with a metabolism-quenching solution which comprises or consists of a fluoroalcohol and thereby obtaining a mixture comprising metabolites, proteins and lipids;
- (b) optionally precipitating the proteins from the mixture, and thereby obtaining a solution comprising the metabolites and the lipids and a protein precipitate;
- (c) optionally diluting the solution with water and/or a water-miscible solvent, wherein the water-miscible solvent comprises one or more of the following: acetonitrile, ethanol, methanol, isopropanol, formic acid, acetic acid or any mixtures thereof;
- (d) passing the solution comprising the metabolites and the lipids from (c) through a solid-phase extraction matrix which binds lipids;
- (e) collecting the metabolites in a flow-through solution;
- (f) washing the solid-phase extraction matrix and combining the wash with the flow through solution of step (e); and
- (g) eluting the lipids from the solid-phase extraction matrix.

Embodiment 36

The method of embodiment 35, wherein the method further comprises one or more of the following additional steps:
- (h) drying the cell lysate obtained in step (a) and resuspending the dried cell lysate in a metabolism-quenching solution which comprises or consists of a fluoroalcohol and thereby obtaining a mixture comprising metabolites, proteins and lipids;
- (j) drying the lipids eluted from the solid-phase extraction matrix;
- (k) drying the metabolites collected in steps (e) and/or (f);
- (l) resolubilizing the dried lipids and/or the dried metabolites; and/or
- (m) separating the protein precipitate from the solution of step (a), from the solution of step (b) and/or from the diluted solution of step (c) via centrifugation and/or by filtration.

Embodiment 37

The method of embodiment 36, wherein the method comprises step (m) and wherein the proteins collected by centrifugation and/or filtration are prepared for an analysis by FASP, PASP, or S-TRAP.

Embodiment 38

The method of any one of embodiments 35-37, wherein cells are adherent cells or suspension cells. When the cells are suspension cells, they may be in a pellet (not in suspension) when they are treated with the MQ solution.

Embodiment 39

The method of any one of embodiments 35-38, wherein the method comprises precipitating proteins with the metabolism-quenching solution, removing the precipitated proteins by filtration and/or centrifugation, optionally diluting the metabolite/lipid mixture with a water, water-organic solution, or organic solution before lipid removal via solid-phase extraction matrix which binds lipids.

Embodiment 40

The method of embodiment 39, wherein the protein precipitate is prepared for analysis using typical protein sample preparation methods, such as FASP, PASP, and S-TRAP.

Embodiment 41

The method of any one of embodiments 35-40, wherein the method comprises re-dissolving a protein precipitate in a solution containing trifluoroethanol or heptafluoroisopropanol.

Embodiment 42

The method of any one of embodiments 35-41, wherein the solid phase extraction material is washed with a wash solution which is 2:1:1 water:ethanol:ACN or 2:1:1 water:ethanol:methanol.

Embodiment 43

The method of any one of embodiments 35-42, wherein the lipids are eluted from the solid-phase extraction matrix with non-polar, non-aqueous solvents or mixtures comprising one or more of MTBE, butanol, methanol, ethanol, dichloromethane, chloroform, or isopropanol.

Embodiment 44

The method of any one of embodiments 35-43, wherein the metabolism-quenching solution comprises 10 v/v % to 100 v/v % of fluoroalcohol, and the fluoroalcohol is one or more of the following: 2,2,2-trifluoroethanol, 2,2-difluoroethanol, 2-fluoroethanol, hexafluoro-2-propanol and nonafluoro-tert-butyl alcohol, 1,1,2,2,2-pentafluoroethanol, or 2,2,3,3,3-pentafluoro-1-propanol.

Embodiment 45

The method of any one of embodiments 35-43, wherein the metabolism-quenching solution comprises from 45 v/v % to 55 v/v % of 2,2,2-trifluoroethanol.

Embodiment 46

The method of any one of embodiments 35-45, wherein at least one method step is performed at room temperature.

Embodiment 47

The method of any one of embodiments 35-46, wherein the metabolism-quenching solution further comprises one or more of the following: water, a water-miscible solvent, a detergent, an acid, a base, a salt, or any combination thereof.

Embodiment 48

The method of any one of embodiments 35-47, wherein the metabolism-quenching solution further comprises one or more of the following: acetonitrile, ethanol, methanol, isopropanol, acetic acid, formic acid, medronic acid, phosphate buffered saline, and/or ammonium bicarbonate.

Embodiment 49

A kit comprising a metabolism-quenching solution, wherein the metabolism-quenching solution comprises, consists essentially of, or consists of a fluoroalcohol, and wherein the kit further comprises and one or more of the following:
    a well plate with a solid sorbent for capturing lipids in one or more formats: a 96-well plate, a 48-well plate, a 24-well plate, a 12-well plate, a 6-well plate, a 384-well plate and/or a 1536-well plate; and/or
    a carrier with the solid sorbent for capturing lipids.

Embodiment 50

The kit of embodiment 49, wherein the kit further comprises: a well plate for culturing, filtering and/or washing cells in one or more formats: a 96-well plate, a 48-well plate, a 24-well plate, a 12-well plate, a 6-well plate, a 384-well plate and/or a 1536-well plate; wherein the well plate for culturing cells is the same as the well plate for filtering cells or the well plate for culturing cells is different from the well plate for filtering cells.

Embodiment 51

The kit of embodiment 49, 50 or 51, wherein the kit further comprises a solution for protein precipitation and/or a sorbent-wash buffer, and one or more of elution buffers.

Embodiment 52

The kit of any one of embodiments 49-51, wherein the metabolism-quenching solution comprises 10-100% of fluoroalcohol by volume, and the fluoroalcohol is one or more of the following: 2,2,2-trifluoroethanol, 2,2-difluoroethanol, 2-fluoroethanol, hexafluoro-2-propanol and nonafluoro-tert-butyl alcohol, 1,1,2,2,2-pentafluoroethanol, or 2,2,3,3,3-pentafluoro-1-propanol.

Embodiment 53

The kit of any one of embodiments 49-52, wherein the kit further comprises a PVDF (polyvinylidene), nylon, PTFE (polytetrafluoroethylene), PC (polycarbonate), PP (polypropylene), PES (polyether sulfone), PVC (polyvinyl chloride), CA (cellulose acetate), CMF (coated cellulose acetate), HDPE (high density polyethylene), regenerated cellulose and/or glass fiber filter, and/or a stacked combination of filter types.

Embodiment 54

The kit of any one of embodiments 49-53, wherein the kit further includes a lipid-elution buffer which comprises one or more of MTBE, butanol, methanol, ethanol, dichloromethane, chloroform, or isopropanol.

Embodiment 55

The method or kit of any one of the preceding embodiments, wherein the fluoroalcohol is 2,2,2-trifluoroethanol.

REFERENCES

1 Weckwerth, W. et al. Process for the integrated extraction, identification and quantification of metabolites, proteins and RNA to reveal their co-regulation in biochemical networks. Proteomics, 4, 78-83, DOI 10.1002/pmic.200200500 (2004).
2 Nakayasu, E. S. et al. MPLEx: a Robust and Universal Protocol for Single-Sample Integrative Proteomic, Metabolomic. and Lipidomic Analyses. mSystems 1, doi:10.1128/mSystems.00043-16 (2016).
3 Burnum-Johnson, K. E. et al. MPLEx: a method for simultaneous pathogen inactivation and extraction of samples for multi-omics profiling. Analyst 142, 442-448, doi:10.1039/c6an02486f (2017).
4 Nicora, C. O. et al. The MPLEx Protocol for Multi-omic Analyses of Soil Samples. J Vis Exp, doi:10.3791/57343 (2018).
5 Valledor, L. et al. A universal protocol for the combined isolation of metabolites, DNA, long RNAs, small RNAs, and proteins from plants and microorganisms. Plant J. 79, 173-80, doi: 10.1111/tpj.12546 (2014).
6 Roume, H. et al. A biomolecular isolation framework for eco-systems biology. ISME 7, 110-21, doi: 10.1038/ismej.2012.72 (2013).
7 Sapcariu, S. C. et al. Simultaneous extraction of proteins and metabolites from cells in culture. MethodsX, 1. 74-80, doi: 10.1016/j.mex.2014.07.002 (2014).
8 Chen, S. et al. Simultaneous extraction of metabolome and lipidome with methyl tert-butyl ether from a single small tissue sample for ultra-high performance liquid chromatography/mass spectrometry. J Chromatogr A 1298, 9-16, doi:10.1016/j.chroma.2013.05.019 (2013).
9 Tambellini, N. P., Zaremberg, V, Turner, R. J. & Weljie, A. M. Evaluation of extraction protocols for simultaneous polar and non-polar yeast metabolite analysis using multivariate projection methods. Metabolites 3, 592-605, doi:10.3390/metabo3030592 (2013).
10 Lee, D. Y Kind, T., Yoon, Y. R., Fiehn,0. & Liu, K. H. Comparative evaluation of extraction methods for simultaneous mass-spectrometric analysis of complex lipids and primary metabolites from human blood plasma. AnalBioanal Chem 406, 7275-7286, doi:10.1007/s00216-014-8124-x (2014).
11 Patterson, R. E., Ducrocq, A. J., McDougall, D. J., Garrett, T J.& Yost, R. A. Comparison of blood plasma sample preparation methods for combined LC-MS lipidomics and metabolomics. J Chromatogr B Analyt Technol Biomed Life Sci 1002, 260-266, doi:10.1016/j.jchromb.2015.08.018 (2015).
12 Pannkuk, E. L. et al. A Lipidomic and Metabolomic Serum Signature from Nonhuman Primates Exposed to Ionizing Radiation. Metabolomics Official journal of the Metabolomic Society 12, doi:10.1007/s11306-016-1010-0 (2016).
13 Juppner, J. et al. Dynamics of lipids and metabolites during the cell cycle of *Chlamydomonas reinhardtii*. Plant J 92, 331-343, doi:10.1111/tpj.13642 (2017).
14 Astarita, G., Stocchero, M. & Paglia, G. Unbiased Lipidomics and Metabolomics of Human Brain Samples. Methods Mol Biol 1750, 255-269, doi:10.1007/978-1-4939-7704-8_17 (2018).
15 Sostare, J. et al. Comparison of modified Matyash method to conventional solvent systems for polarmetabolite and lipid extractions. Analytica chimica acta 1037, 301-315, doi:10.1016/j.aca.2018.03.019 (2018).
16 Ulmer, C. Z, Jones, C. M., Yost, R. A., Garrett, T. J. & Bowden, J. A. Optimization of Folch, Bligh-Dyer, and Matyash sample-to-extraction solvent ratios for human plasma-based lipidomics studies. Analytica chimica acta 1037, 351-357, doi:10.1016{j.aca.2018.08.004 (2018).
17 Li, Y et al. A novel approach to the simultaneous extraction and non-targeted analysis of the small molecules metabolome and lipidome using 96-well solid phase extraction plates with column-switching technology. J Chromatogr A 1409, 277-281, doi:10.1016/j.chroma 0.2015.07.048 (2015).
18 Salem, M. A., Juppner, J., Bajdzienko, K. & Giavalisco, P. Protocol: a fast, comprehensive and reproducible one-step extraction method for the rapid preparation of polar and semi-polar metabolites, lipids, proteins, starch and cell wall polymers from a single sample. Plant Methods 12, 45, doi:10.1186/s13007-016-0146-2 (2016).
19 Salem, M., Bernach, M., Bajdzienko, K. & Giavalisco, P. A Simple Fractionated Extraction Method for the Comprehensive Analysis of Metabolites, Lipids, and Proteins from a Single Sample. J Vis Exp, doi:10.3791/55802 (2017).
20 Bylda, C. et al. Recent advances in sample preparation techniques to overcome difficulties encountered during quantitative analysis of small molecules from biofluids using LC-MS/MS. Analyst, 139, 2265-76, DOI: 10.1039/C4AN00094C (2014).
21 Lu, W. et al. Metabolite Measurement: Pitfalls to Avoid and Practices to Follow. Annu. Rev. Biochem. 86, 277-304, 2017
22 Kapoore, R. V. et al. Influence of washing and quenching in profiling the metabolome of adherent mammalian cells: a case study with the metastatic breast cancer cell line MDA-MB-231. Analyst, 142, 2038, 2017.
23 Martano, G. et al. Fast sampling method for mammalian cell metabolic analyses using liquid chromatography-mass spectrometry. Nature Protocols, 10, 2015.
24 Sellick, C. A. et al. Effective quenching processes for physiologically valid metabolite profiling of suspension cultured mammalian cells. Anal. Chem. 81, 174-183, 2009.
25 Dietmair S. et al. Towards quantitative metabolomics of mammalian cells: development of a metabolite extraction protocol. Anal. Biochem. 404, 155-164, 2010.
26 Kronthaler, J. et al. Optimizing high-throughput metabolomic biomarker screening: a study of quenching solutions to freeze intracellular metabolism in CHO cells. OMICS: A Journal of Integrative Biology, 16, 90-97, 2012.
27 Bordag, N. et al. Fast filtration of bacterial or mammalian suspension cell cultures for optimal metabolomics results. PLOS ONE, 11, e0159389, 2016.
28 Leon, Z. et al. Mammalian cell metabolomics: experimental design and sample preparation. Electrophoresis, 34, 2762-2775, 2013.
29 Lorenz, M. et al. Reducing time and increasing sensitivity in sample preparation for adherent mammalian cell metabolomics. Anal. Chem. 83, 3406-3414, 2011.
30 Nitin Agrawal, Ryan Kelly, Xuefei Sun, Keqi Tang, and Richard D. Smith. Towards a Microfluidic nanoESl-MS Platform for Sample Preparation and Analysis of Single Cells. 2010 ASMS poster. https://panomics.pnnl.gov/poster/ASMS2010/Agrawal_PNNL_ASMS2010.pdf
31 Folch, J., et al., J Biol Chem 226, 497-509 (1957).
32 Bligh, E. G. & Dyer, W. J. Can J Biochem Physiol 37, 911-917, doi:10.1139/o59-099 (1959).
33 Matyash, V., et al., J Lipid Res 49, 1137-1146, doi:10.1194/j1r.D700041-JLR200 (2008).
34 Alshehry, Z. H. et al., Metabolites 5, 389-403, doi:10.3390/metabo5020389 (2015).
35 Koelmel, J. et al Agilent Application Note #5994-0775EN, 2019

What is claimed is:

1. A method for extracting metabolites from a biological sample, the method comprising:
   contacting at room temperature the biological sample with a metabolism-quenching solution comprising a fluoroalcohol,
   inhibiting one or more metabolic reactions in the biological sample with the fluoroalcohol;
   extracting a mixture from the biological sample with the metabolism-quenching solution comprising the fluoroalcohol, the mixture comprising metabolites, lipids and proteins;
   separating the metabolites from the mixture; and
   collecting the metabolites.

2. The method of claim 1, wherein one or more steps in the method is automated on a liquid-handling platform.

3. The method of claim 1, wherein the metabolism-quenching solution comprises 10-100% of the fluoroalcohol by volume.

4. The method of claim 1, wherein the fluoroalcohol is one or more of the following: 2,2,2-trifluoroethanol, 2,2-difluoroethanol, 2-fluoroethanol, hexafluoro-2-propanol, nonafluoro-tert-butyl alcohol, 1,1,2,2,2-pentafluoroethanol, and/or 2,2,3,3,3-pentafluoro-1-propanol.

5. The method of claim 1, wherein the metabolism-quenching solution comprises from 45 v/v % to 55 v/v % of 2,2,2-trifluoroethanol.

6. The method of claim 1, wherein the biological sample comprises cells, and the cells are lysed by the fluoroalcohol.

7. The method of claim 1, wherein the metabolism-quenching solution comprises 2,2,2-trifluoroethanol.

8. The method of claim 1, wherein the separation of metabolites from the mixture comprises:
   a) passing the mixture through a solid-phase extraction matrix which binds the lipids; and
   b) collecting the metabolites in a flow through solution.

9. The method of claim 8, wherein the method further comprises one or more of the following: c) washing the solid-phase extraction matrix with a wash solution which contains a water-containing solvent mixture and combining the wash solution with the flow through solution; and/or d) eluting and collecting lipids; and/or e) drying the collected metabolites and/or drying the eluted lipids.

10. The method of claim 9, wherein the wash solution contains one or more of the following: 2:1:1 water:ethanol:acetonitrile or 2:1:1 water:ethanol:methanol.

11. The method of claim 1, wherein the method further comprises contacting the mixture with an organic solvent and precipitating protein/peptide material from the mixture.

12. The method of claim 1, wherein the method further comprises collecting proteins precipitated with the metabolism-quenching solution and preparing the collected proteins for analysis.

13. The method of claim 1, wherein the method further comprises one or more of the following: filtering the mixture, precipitating proteins from the mixture, centrifuging the mixture, passing the mixture through a solid-phase extraction matrix which binds lipids and collecting metabolites, concentrating the mixture, drying the mixture, diluting the mixture, changing a solvent for the mixture, washing the matrix and combining the wash solution with the flow through solution, or any combination thereof.

14. The method of claim 1, wherein the method comprises filtering the mixture through a PVDF (polyvinylidene), nylon, PTFE (polytetrafluoroethylene), PC (polycarbonate), PP (polypropylene), PES (polyether sulfone), PVC (polyvinyl chloride), CA (cellulose acetate), CMF (coated cellulose acetate), HDPE (high density polyethylene), regenerated cellulose or glass fiber filter, or a stacked combination of filter types.

15. The method of claim 14, wherein the mixture further comprises nucleic acids, and wherein the method further comprises collecting the nucleic acids on the filter.

16. The method of claim 1, wherein the biological sample comprises cells, the method comprising:
   lysing and quenching the cells with a first metabolism-quenching solution which comprises from 10 v/v % to 100 v/v % of a fluoroalcohol, and thereby obtaining a mixture comprising metabolites, proteins and lipids; and
   precipitating the proteins from the mixture with an organic solvent, and thereby obtaining a solution comprising the metabolites and the lipids and a protein precipitate.

17. The method of claim 16, wherein the method further comprises one or more of the following additional steps:
   drying the mixture and re-dissolving the mixture in a second metabolism-quenching solution which comprises from 10 v/v % to 100 v/v % of a fluoroalcohol, wherein the first metabolism-quenching solution may be the same or different from the second metabolism-quenching solution;
   drying lipids eluted from a solid-phase extraction matrix and/or drying metabolites collected in a flow through solution, wherein, prior to the solid-phase extraction, a dilution step is optionally performed with water and/or a water-miscible solvent, wherein the water-miscible solvent comprises one or more of the following: acetonitrile, ethanol, methanol, isopropanol, formic acid, acetic acid or any mixtures thereof;
   resolubilizing the dried lipids and/or the dried metabolites; and/or
   separating the protein precipitate via centrifugation and/or by filtration.

18. The method of claim 16, wherein the method is further characterized by one or more of the following features: 1) the protein precipitate is collected; 2) the lipids are eluted from a solid-phase extraction matrix with non-polar, non-aqueous solvents or mixtures comprising one or more of MTBE (methyl tertiary-butyl ether), butanol, methanol, ethanol, dichloromethane, chloroform, or isopropanol; 3) the metabolism-quenching solution further comprises one or more of the following: water, a water-miscible solvent, a detergent, an acid, a base, a salt, or any combination thereof; and/or 4) the metabolism-quenching solution further comprises one or more of the following: acetonitrile, ethanol, methanol, isopropanol, acetic acid, formic acid, medronic acid, phosphate buffered saline, and/or ammonium bicarbonate.

19. The method of claim 1, wherein the room temperature is a temperature in the range from 15° C. to 30° C.

20. The method of claim 1, wherein extracting the mixture occurs without separating distinct liquid phases.

21. A method for extracting metabolites from a biological sample, the method comprising:
   contacting at room temperature the biological sample with a metabolism-quenching solution comprising a fluoroalcohol,
   inhibiting one or more metabolic reactions in the biological sample with the fluoroalcohol;
   extracting a mixture, from the biological sample with the metabolism-quenching solution comprising the fluoroalcohol, the mixture comprising metabolites, lipids and proteins;
   contacting the mixture with an organic solvent and precipitating protein material from the mixture;
   separating the metabolites from the mixture; and
   collecting the metabolites.

22. A method for extracting metabolites from a biological sample, the method comprising:
   contacting at room temperature the biological sample with a metabolism-quenching solution comprising a fluoroalcohol,
   inhibiting one or more metabolic reactions in the biological sample with the fluoroalcohol;
   extracting a mixture, from the biological sample with the metabolism-quenching solution comprising the fluoroalcohol, the mixture comprising metabolites, lipids and proteins;
   separating precipitated proteins from the mixture comprising metabolites, lipids and proteins;
   separating the metabolites from the remaining mixture; and
   collecting the metabolites.

* * * * *